US006953657B2

(12) United States Patent
Bertin

(10) Patent No.: US 6,953,657 B2
(45) Date of Patent: Oct. 11, 2005

(54) MOLECULES OF THE CARD-RELATED PROTEIN FAMILY AND USES THEREOF

(75) Inventor: John Bertin, Watertown, MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 204 days.

(21) Appl. No.: 09/996,617

(22) Filed: Nov. 27, 2001

(65) Prior Publication Data

US 2002/0128198 A1 Sep. 12, 2002

Related U.S. Application Data

(63) Continuation-in-part of application No. 09/936,071, filed on Aug. 15, 2001, which is a continuation-in-part of application No. 09/428,252, filed on Oct. 27, 1999, now abandoned, and a continuation-in-part of application No. 09/340,620, filed on Jun. 28, 1999, now Pat. No. 6,482,933.

(51) Int. Cl.[7] .......................... C12Q 1/68; G01N 33/53
(52) U.S. Cl. .............................. 435/4; 435/6; 435/7.1
(58) Field of Search ................................ 435/4, 6, 7.1

(56) References Cited

U.S. PATENT DOCUMENTS

| 6,033,855 | A | 3/2000 | Bertin |
| 2002/0128219 | A1 | 9/2002 | Bertin et al. |
| 2002/0142979 | A1 | 10/2002 | Bertin |
| 2002/0192643 | A1 | 12/2002 | Reed |

FOREIGN PATENT DOCUMENTS

| WO | WO 98/55507 | 12/1998 |
| WO | WO 01/16170 A2 * | 3/2001 |
| WO | WO 01/30813 | 5/2001 |

OTHER PUBLICATIONS

Ahmad et al.; "CRADD, a Novel Human Apoptotic Adaptor Molecule for Caspase–2, and FasL/ Tumor Necrosis Factor Receptor–interacting Protein RIP[1]," Cancer Res.., vol. 57:615–619 (1997).
Baker et al., "Transducers of life and death: TNF receptor superfamily and associated proteins" Oncogene 12:1–9, 1996.
Carter et al.; "Selective Activation of NF–κB by Nerve Growth Factor Through the Neurotrophin Receptor p75," Science, vol. 272:542–545 (1996).
Chinnaiyan et al., "The cell–death machine" Current Biology 6:555–562, 1996.
Duan et al.; "RAIDD is a new "death" adaptor molecule." NATURE, vol. 385:86–89 (1997).
Epstein, "Nuclear FactorκB—A Pivotal Transcription Factor in Chronic Inflammatory Diseases," New England J. of Medicine, vol. 336:1066–1071(1997).
Friedlander et al.; "ICE, neuronal apoptosis and neurodegeneration," Cell Death and Differentiation, vol. 5:823–831 (1998).
Hofman et al.; "The CARD domain: a new apoptotic signaling motif," TIBS Reference Edition, vol. 22:155 (1997).
Hu et al.; "Bcl–X$_L$ interacts with Apaf–1 and inhibits Apaf–1–dependent caspase–9 activation," Proc. Natl. Acad. Sci., vol. 95:4386–4391 (1998).

Humke et al., "Iceberg: A Novel Inhibitor of Interleukin–1β Generation," Cell, 103:99–111 (Sep. 29, 2000).
Inohara et al.; "RICK, a Novel Protein Kinase Containing a Caspase Recruitment Domain, Interacts with CLARP and Regulates CD95–mediated Apoptosis," J. Biol. Chem., vol. 273:12296–12300 (1998).
Li et al,; "Cytochrome c and dATP–Dependent Formation of Apaf–1/Caspase–9 Complex Initiates an Apoptotic Protease Cascasde," CELL, vol. 91:479–489 (1997).
McCarthy et al., "RIP2 is a novel NF–κB–activating and cell death–inducting kinase" J. of Biol. Chem. 273(27):16968–16975 1998.
Miller et al.; "Life and death decisions: a biological role for the p75 neurotrophin receptor," Cell Death Differentiation, vol. 5:343–345 (1998).
Miura et al.; "Induction of Apoptosis in Fibroblasts by IL–1β–Converting Enzyme, a Mammalian Homolog of the C. elegans Cell Death Gene ced–3," CELL, vol. 75:653–660, Nov. (1993).
Nagase et al.; "Prediction of the Coding Sequences of Unidentified Human Genes, XIII. The Complete Sequence of 100 new cDNA Clones from Brain Which Code for Large Proteins in vitro," DNA Research vol. 6: 63–70 (1999).
Navab et al.; "Pathogenesis of Atherosclerosis," Amer. J. of Cardiology, vol. 76:18C–23C (1995).
Razmarsa et al. (2002) "CARD–8 Protein, a New CARD Family Member That Regulates Caspase–1 Activation and Apoptosis", J. of Biol. Chem. 277(16):13952–13958.
Reed, J., "Cytochrome c: Can't live with it–Can't live without it" Cell 91:559–562, 1997.
Slee et al.; "Ordering the Cytochrome c–initiated Caspase Cascade: Hierarchical Activation of Caspases–2,, –3, –7, –8, and –10 in a Caspase 9–dependent Manner," J. Cell Biol., vol. 144:281–292 (1999).
Song et al.; "Boo, a novel negative regulator of cell death, interacts with Apaf–1," The Embo Journal, vol. 18:167–178 (1999).
Srinivasula et al., "Autoactivation of Procaspase–9 by Apaf–1–Mediated Oligomerization," Mol. Cell, vol. 1:949–957 (1998).
Wallach, D., "Cell death induction by TNF: a matter of self control" TIBS 22:107–109, 1997.
Wang et al.; "NF–κB Antiapoptosis: Induction of TRAF1 and TRAF2 and c–IAP1 and c–IAP2 to Suppress Caspase–8 Activation," Science, vol. 281:1680–1683 (1998).
Yan et al., "mE10, a novel caspase recruitment domain–containing proapoptotic molecule" J. of Bio. Chem. 274(15):10287–10292, 1999.
Gen Bank Accession No. AB023143 Apr. 4, 1999.
GenBank Accession No. AB023172, Nagase et al., (Jun. 16, 1999).
GenBank Accession No. AL117470, Koehrer et al., (Feb. 18, 2000).
Gen Bank Accession No. HSM800983 Sep. 15, 1999.

* cited by examiner

Primary Examiner—Sean McGarry
(74) Attorney, Agent, or Firm—Millennium Pharmaceuticals, Inc.

(57) ABSTRACT

Novel CARD–7 and CARD–8 polypeptides, proteins, and nucleic acid molecules are disclosed. Diagnostic, screening and therapeutic methods utilizing compositions of the invention are also provided.

13 Claims, 12 Drawing Sheets

```
GCCCCAGGGCCTGGAGAGGTCTGAAGAAACCTGGGAGCCAGCAGCCCGGGGCTCCACTCTGGGTTCTGAAAGCCCATTC   79

CCTGCTCTGCGGCTCCTCCCACCCCACCTCTTCTCAGCCTTGCAGCTCAAGGGTTGATCTCAGGAGTCCAGGACCCAGG  158

AGAGGGAAGAATCTGAGGAACACAGAACAGTGAGCGTTGCCCACACCCCATCTCCCGTCACCACATCTCCCCTCACCCT  237

CACCCTCCCTGCCTGGCCCTGGACCCCATCCCAGGACCTCCCTATCAGCTGACTTCTTCCAGTGTCTTGCAGGCCCCTC  316

TGGGCTCCTCCCTCCCCTGGCTTTTCCTACCACTCCCCCTCTATCGGCGTCTATCTGTAGGTGCCCTGGGATTTATAAA  395

ACTGGGTTCCGAATGCTGAATAAGAGACGGTAAGAGCCAAGGCAAAGGACAGCACTGTTCTCTGCCTGCCTGATACCCT  474

M   A   G   G   A   W   G      7
CACCACCTGGGAACATCCCCCAGACACCCTCTTAACTCCGGGACAGAG ATG GCT GGC GGA GCC TGG GGC         543

R   L   A   C   Y   L   E   F   L   K   K   E   E   L   K   E   F   Q   L   L     27
CGC CTG GCC TGT TAC TTG GAG TTC CTG AAG AAG GAG GAG CTG AAG GAG TTC CAG CTT CTG    603

L   A   N   K   A   H   S   R   S   S   S   G   E   T   P   A   Q   P   E   K     47
CTC GCC AAT AAA GCG CAC TCC AGG AGC TCT TCG GGT GAG ACA CCC GCT CAG CCA GAG AAG    663

T   S   G   M   E   V   A   S   Y   L   V   A   Q   Y   G   E   Q   R   A   W     67
ACG AGT GGC ATG GAG GTG GCC TCG TAC CTG GTG GCT CAG TAT GGG GAG CAG CGG GCC TGG    723

D   L   A   L   H   T   W   E   Q   M   G   L   R   S   L   C   A   Q   A   Q     87
GAC CTA GCC CTC CAT ACC TGG GAG CAG ATG GGG CTG AGG TCA CTG TGC GCC CAA GCC CAG    783

E   G   A   G   H   S   P   S   F   P   Y   S   P   S   E   P   H   L   G   S    107
GAA GGG GCA GGC CAC TCT CCC TCA TTC CCC TAC AGC CCA AGT GAA CCC CAC CTG GGG TCT    843

P   S   Q   P   T   S   T   A   V   L   M   P   W   I   H   E   L   P   A   G    127
CCC AGC CAA CCC ACC TCC ACC GCA GTG CTA ATG CCC TGG ATC CAT GAA TTG CCG GCG GGG    903

C   T   Q   G   S   E   R   R   V   L   R   Q   L   P   D   T   S   G   R   R    147
TGC ACC CAG GGC TCA GAG AGA AGG GTT TTG AGA CAG CTG CCT GAC ACA TCT GGA CGC CGC    963

W   R   E   I   S   A   S   L   L   Y   Q   A   L   P   S   S   P   D   H   E    167
TGG AGA GAA ATC TCT GCC TCA CTC CTC TAC CAA GCT CTT CCA AGC TCC CCA GAC CAT GAG   1023

S   P   S   Q   E   S   P   N   A   P   T   S   T   A   V   L   G   S   W   G    187
TCT CCA AGC CAG GAG TCA CCC AAC GCC CCC ACA TCC ACA GCA GTG CTG GGG AGC TGG GGA   1083

S   P   P   Q   P   S   L   A   P   R   E   Q   E   A   P   G   T   Q   W   P    207
TCC CCA CCT CAG CCC AGC CTA GCA CCC AGA GAG CAG GAG GCT CCT GGG ACC CAA TGG CCT   1143

L   D   E   T   S   G   I   Y   Y   T   E   I   R   E   R   E   R   E   K   S    227
CTG GAT GAA ACG TCA GGA ATT TAC TAC ACA GAA ATC AGA GAA AGA GAG AGA GAG AAA TCA   1203

E   K   G   R   P   P   W   A   A   V   V   G   T   P   P   Q   A   H   T   S    247
GAG AAA GGC AGG CCC CCA TGG GCA GCG GTG GTA GGA ACG CCC CCA CAG GCG CAC ACC AGC   1263

L   Q   P   H   H   H   P   W   E   P   S   V   R   E   S   L   C   S   T   W    267
CTA CAG CCC CAC CAC CAC CCA TGG GAG CCT TCT GTG AGA GAG AGC CTC TGT TCC ACA TGG   1323

P   W   K   N   E   D   F   N   Q   K   F   T   Q   L   L   L   Q   R   P         287
CCC TGG AAA AAT GAG GAT TTT AAC CAA AAA TTC ACA CAG CTG CTA CTT CTA CAA AGA CCT   1383

H   P   R   S   Q   D   P   L   V   K   R   S   W   P   D   Y   V   E   E   N    307
CAC CCC AGA AGC CAA GAT CCC CTG GTC AAG AGA AGC TGG CCT GAT TAT GTG GAG GAG AAT   1443

R   G   H   L   I   E   I   R   D   L   F   G   P   G   L   D   T   Q   E   P    327
CGA GGA CAT TTA ATT GAG ATC AGA GAC TTA TTT GGC CCA GGC CTG GAT ACC CAA GAA CCT   1503

R   I   V   I   L   Q   G   A   A   G   I   G   K   S   T   L   A   R   Q   V    347
CGC ATA GTC ATA CTG CAG GGG GCT GCT GGA ATT GGG AAG TCA ACA CTG GCC AGG CAG GTG   1563
```

FIG. 1A

```
  K   E   A   W   G   R   G   Q   L   Y   G   D   R   F   Q   H   V   F   Y   F   367
AAG GAA GCC TGG GGG AGA GGC CAG CTG TAT GGG GAC CGC TTC CAG CAT GTC TTC TAC TTC  1623

S   C   R   E   L   A   Q   S   K   V   V   S   L   A   E   L   I   G   K   D   387
AGC TGC AGA GAG CTG GCC CAG TCC AAG GTG GTG AGT CTC GCT GAG CTC ATC GGA AAA GAT  1683

G   T   A   T   P   A   P   I   R   Q   I   L   S   R   P   E   R   L   L   F   407
GGG ACA GCC ACT CCG GCT CCC ATT AGA CAG ATC CTG TCT AGG CCA GAG CGG CTG CTC TTC  1743

I   L   D   G   V   D   E   P   G   W   V   L   Q   E   P   S   S   E   L   C   427
ATC CTC GAT GGT GTA GAT GAG CCA GGA TGG GTC TTG CAG GAG CCG AGT TCT GAG CTC TGT  1803

L   H   W   S   Q   P   Q   P   A   D   A   L   L   G   S   L   L   G   K   T   447
CTG CAC TGG AGC CAG CCA CAG CCG GCG GAT GCA CTG CTG GGC AGT TTG CTG GGG AAA ACT  1863

I   L   P   E   A   S   F   L   I   T   A   R   T   T   A   L   Q   N   L   I   467
ATA CTT CCC GAG GCA TCC TTC CTG ATC ACG GCT CGG ACC ACA GCT CTG CAG AAC CTC ATT  1923

P   S   L   E   Q   A   R   W   V   E   V   L   G   F   S   E   S   S   R   K   487
CCT TCT TTG GAG CAG GCA CGT TGG GTA GAG GTC CTG GGG TTC TCT GAG TCC AGC AGG AAG  1983

E   Y   F   Y   R   Y   F   T   D   E   R   Q   A   I   R   A   F   R   L   V   507
GAA TAT TTC TAC AGA TAT TTC ACA GAT GAA AGG CAA GCA ATT AGA GCC TTT AGG TTG GTC  2043

K   S   N   K   E   L   W   A   L   C   L   V   P   W   V   S   W   L   A   C   527
AAA TCA AAC AAA GAG CTC TGG GCC CTG TGT CTT GTG CCC TGG GTG TCC TGG CTG GCC TGC  2103

T   C   L   M   Q   Q   M   K   R   K   E   K   L   T   L   T   S   K   T   T   547
ACT TGC CTG ATG CAG CAG ATG AAG CGG AAG GAA AAA CTC ACA CTG ACT TCC AAG ACC ACC  2163

T   T   L   C   L   H   Y   L   A   Q   A   L   Q   A   Q   P   L   G   P   Q   567
ACA ACC CTC TGT CTA CAT TAC CTT GCC CAG GCT CTC CAA GCT CAG CCA TTG GGA CCC CAG  2223

L   R   D   L   C   S   L   A   A   E   G   I   W   Q   K   K   T   L   F   S   587
CTC AGA GAC CTC TGC TCT CTG GCT GCT GAG GGC ATC TGG CAA AAA AAG ACC CTT TTC AGT  2283

P   D   D   L   R   K   H   G   L   D   G   A   I   I   S   T   F   L   K   M   607
CCA GAT GAC CTC AGG AAG CAT GGG TTA GAT GGG GCC ATC ATC TCC ACC TTC TTG AAG ATG  2343

G   I   L   Q   E   H   P   I   P   L   S   Y   S   F   I   H   L   C   F   Q   627
GGT ATT CTT CAA GAG CAC CCC ATC CCT CTG AGC TAC AGC TTC ATT CAC CTC TGT TTC CAA  2403

E   F   F   A   A   M   S   Y   V   L   E   D   E   K   G   R   G   K   H   S   647
GAG TTC TTT GCA GCA ATG TCC TAT GTC TTG GAG GAT GAG AAG GGG AGA GGT AAA CAT TCT  2463

N   C   I   I   D   L   E   K   T   L   E   A   Y   G   I   H   G   L   F   G   667
AAT TGC ATC ATA GAT TTG GAA AAG ACG CTA GAA GCA TAT GGA ATA CAT GGC CTG TTT GGG  2523

A   S   T   T   R   F   L   L   G   L   L   S   D   E   G   E   R   E   M   E   687
GCA TCA ACC ACA CGT TTC CTA TTG GGC CTG TTA AGT GAT GAG GGG GAG AGA GAG ATG GAG  2583

N   I   F   H   C   R   L   S   Q   G   R   N   L   M   Q   W   V   P   S   L   707
AAC ATC TTT CAC TGC CGG CTG TCT CAG GGG AGG AAC CTG ATG CAG TGG GTC CCG TCC CTG  2643

Q   L   L   L   Q   P   H   S   L   E   S   L   H   C   L   Y   E   T   R   N   727
CAG CTG CTG CTG CAG CCA CAC TCT CTG GAG TCC CTC CAC TGC TTG TAC GAG ACT CGG AAC  2703

K   T   F   L   T   Q   V   M   A   H   F   E   E   M   G   M   C   V   E   T   747
AAA ACG TTC CTG ACA CAA GTG ATG GCC CAT TTC GAA GAA ATG GGC ATG TGT GTA GAA ACA  2763

D   M   E   L   L   V   C   T   F   C   I   K   F   S   R   H   V   K   K   L   767
GAC ATG GAG CTC TTA GTG TGC ACT TTC TGC ATT AAA TTC AGC CGC CAC GTG AAG AAG CTT  2823

Q   L   I   E   G   R   Q   H   R   S   T   W   S   P   T   M   V   V   L   F   787
CAG CTG ATT GAG GGC AGG CAG CAC AGA TCA ACA TGG AGC CCC ACC ATG GTA GTC CTG TTC  2883

```
                                                                               R   N   L   K   E   L   D   L   S   G   N   S   L   S   H   S   A   V   K   S    827
AGG TGG GTC CCA GTC ACA GAT GCC TAT TGG CAG ATT CTC TTC TCC GTC CTC AAG GTC ACC  2943
AGA AAC CTG AAG GAG CTG GAC CTA AGT GGA AAC TCG CTG AGC CAC TCT GCA GTG AAG AGT  3003

L   C   K   T   L   R   R   P   R   C   L   L   E   T   L   R   L   A   G   C    847
CTT TGT AAG ACC CTG AGA CGC CCT CGC TGC CTC CTG GAG ACC CTG CGG TTG GCT GGC TGT  3063

G   L   T   A   E   D   C   K   D   L   A   F   G   L   R   A   N   Q   T   L    867
GGC CTC ACA GCT GAG GAC TGC AAG GAC CTT GCC TTT GGG CTG AGA GCC AAC CAG ACC CTG  3123

T   E   L   D   L   S   F   N   V   L   T   D   A   G   A   K   H   L   C   Q    887
ACC GAG CTG GAC CTG AGC TTC AAT GTG CTC ACG GAT GCT GGA GCC AAA CAC CTT TGC CAG  3183

R   L   R   Q   P   S   C   K   L   Q   R   L   Q   L   V   S   C   G   L   T    907
AGA CTG AGA CAG CCG AGC TGC AAG CTA CAG CGA CTG CAG CTG GTC AGC TGT GGC CTC ACG  3243

S   D   C   C   Q   D   L   A   S   V   L   S   A   S   P   S   L   K   E   L    927
TCT GAC TGC TGC CAG GAC CTG GCC TCT GTG CTT AGT GCC AGC CCC AGC CTG AAG GAG CTA  3303

D   L   Q   Q   N   N   L   D   D   V   G   V   R   L   L   C   E   G   L   R    947
GAC CTG CAG CAG AAC AAC CTG GAT GAC GTT GGC GTG CGA CTG CTC TGT GAG GGC CTC AGG  3363

H   P   A   C   K   L   I   R   L   G   L   D   Q   T   T   L   S   D   E   M    967
CAT CCT GCC TGC AAA CTC ATA CGC CTG GGG CTG GAC CAG ACA ACT CTG AGT GAT GAG ATG  3423

R   Q   E   L   R   A   L   E   Q   E   K   P   Q   L   L   I   F   S   R   R    987
AGG CAG GAA CTG AGG GCC CTG GAG CAG GAG AAA CCT CAG CTG CTC ATC TTC AGC AGA CGG  3483

K   P   S   V   M   T   P   T   E   G   L   D   T   G   E   M   S   N   S   T   1007
AAA CCA AGT GTG ATG ACC CCT ACT GAG GGC CTG GAT ACG GGA GAG ATG AGT AAT AGC ACA  3543

S   S   L   K   R   Q   R   L   G   S   E   R   A   A   S   H   V   A   Q   A   1027
TCC TCA CTC AAG CGG CAG AGA CTC GGA TCA GAG AGG GCG GCT TCC CAT GTT GCT CAG GCT  3603

N   L   K   L   L   D   V   S   K   I   F   P   I   A   E   I   A   E   E   S   1047
AAT CTC AAA CTC CTG GAC GTG AGC AAG ATC TTC CCA ATT GCT GAG ATT GCA GAG GAA AGC  3663

S   P   E   V   V   P   V   E   L   L   C   V   P   S   P   A   S   Q   G   D   1067
TCC CCA GAG GTA GTA CCG GTG GAA CTC TTG TGC GTG CCT TCT CCT GCC TCT CAA GGG GAC  3723

L   H   T   K   P   L   G   T   D   D   D   F   W   G   P   T   G   P   V   A   1087
CTG CAT ACG AAG CCT TTG GGG ACT GAC GAT GAC TTC TGG GGC CCC ACG GGG CCT GTG GCT  3783

T   E   V   V   D   K   E   K   N   L   Y   R   V   H   F   P   V   A   G   S   1107
ACT GAG GTA GTT GAC AAA GAA AAG AAC TTG TAC CGA GTT CAC TTC CCT GTA GCT GGC TCC  3843

Y   R   W   P   N   T   G   L   C   F   V   M   R   E   A   V   T   V   E   I   1127
TAC CGC TGG CCC AAC ACG GGT CTC TGC TTT GTG ATG AGA GAA GCG GTG ACC GTT GAG ATT  3903

E   F   C   V   W   D   Q   F   L   G   E   I   N   P   Q   H   S   W   M   V   1147
GAA TTC TGT GTG TGG GAC CAG TTC CTG GGT GAG ATC AAC CCA CAG CAC AGC TGG ATG GTG  3963

A   G   P   L   L   D   I   K   A   E   P   G   A   V   E   A   V   H   L   P   1167
GCA GGG CCT CTG CTG GAC ATC AAG GCT GAG CCT GGA GCT GTG GAA GCT GTG CAC CTC CCT  4023

H   F   V   A   L   Q   G   G   H   V   D   T   S   L   F   Q   M   A   H   F   1187
CAC TTT GTG GCT CTC CAA GGG GGC CAT GTG GAC ACA TCC CTG TTC CAA ATG GCC CAC TTT  4083

K   E   E   G   M   L   L   E   K   P   A   R   V   E   L   H   H   I   V   L   1207
AAA GAG GAG GGG ATG CTC CTG GAG AAG CCA GCC AGG GTG GAG CTG CAT CAC ATA GTT CTG  4143

E   N   P   S   F   S   P   L   G   V   L   L   K   M   I   H   N   A   L   R   1227
GAA AAC CCC AGC TTC TCC CCC TTG GGA GTC CTC CTG AAA ATG ATC CAT AAT GCC CTG CGC  4203

F   I   P   V   T   S   V   V   L   L   Y   H   R   V   H   P   E   E   V   T   1247
TTC ATT CCC GTC ACC TCT GTG GTG TTG CTT TAC CAC CGC GTC CAT CCT GAG GAA GTC ACC  4263
```

FIG. 1C

```
  F    H    L    Y    L    I    P    S    D    C    S    I    R    K    E    L    E    L    C    Y   1267
 TTC  CAC  CTC  TAC  CTG  ATC  CCA  AGT  GAC  TGC  TCC  ATT  CGG  AAG  GAA  CTG  GAG  CTC  TGC  TAT  4323

R    S    P    G    E    D    Q    L    F    S    E    F    Y    V    G    H    L    G    S    G   1287
 CGA  AGC  CCT  GGA  GAA  GAC  CAG  CTG  TTC  TCG  GAG  TTC  TAC  GTT  GGC  CAC  TTG  GGA  TCA  GGG  4383

I    R    L    Q    V    K    D    K    K    D    E    T    L    V    W    E    A    L    V    K   1307
 ATC  AGG  CTG  CAA  GTG  AAA  GAC  AAG  AAA  GAT  GAG  ACT  CTG  GTG  TGG  GAG  GCC  TTG  GTG  AAA  4443

P    G    D    L    M    P    A    T    T    L    I    P    P    A    R    I    A    V    P    S   1327
 CCA  GGA  GAT  CTC  ATG  CCT  GCA  ACT  ACT  CTG  ATC  CCT  CCA  GCC  CGC  ATA  GCC  GTA  CCT  TCA  4503

P    L    D    A    P    Q    L    L    H    F    V    D    Q    Y    R    E    Q    L    I    A   1347
 CCT  CTG  GAT  GCC  CCG  CAG  TTG  CTG  CAC  TTT  GTG  GAC  CAG  TAT  CGA  GAG  CAG  CTG  ATA  GCC  4563

R    V    T    S    V    E    V    V    L    D    K    L    H    G    Q    V    L    S    Q    E   1367
 CGA  GTG  ACA  TCG  GTG  GAG  GTT  GTC  TTG  GAC  AAA  CTG  CAT  GGA  CAG  GTG  CTG  AGC  CAG  GAG  4623

Q    Y    E    R    V    L    A    E    N    T    R    P    S    Q    M    R    K    L    F    S   1387
 CAG  TAC  GAG  AGG  GTG  CTG  GCT  GAG  AAC  ACG  AGG  CCC  AGC  CAG  ATG  CGG  AAG  CTG  TTC  AGC  4683

L    S    Q    S    W    D    R    K    C    K    D    G    L    Y    Q    A    L    K    E    T   1407
 TTG  AGC  CAG  TCC  TGG  GAC  CGG  AAG  TGC  AAA  GAT  GGA  CTC  TAC  CAA  GCC  CTG  AAG  GAG  ACC  4743

H    P    H    L    I    M    E    L    W    E    K    G    S    K    K    G    L    L    P    L   1427
 CAT  CCT  CAC  CTC  ATT  ATG  GAA  CTC  TGG  GAG  AAG  GGC  AGC  AAA  AAG  GGA  CTC  CTG  CCA  CTC  4803

S    S    *                                                                                         1430
 AGC  AGC  TGA                                                                                        4812
```

AGTATCAACACCAGCCCTTGACCCTTGAGTCCTGGCTTTGGCTGACCCTTCTTTGGGTCTCAGTTTCTTTCTCTGCAAA 4891

CAAGTTGCCATCTGGTTTGCCTTCCAGCACTAAAGTAATGGAACTTTGATGATGCCTTTGCTGGGCATTATGTGTCCAT 4970

GCCAGGGATGCCACAGGGGGCCCCAGTCCAGGTGGCCTAACAGCATCTCAGGGAATGTCCATCTGGAGCTGGCAAGACC 5049

CCTGCAGACCTCATAGAGCCTCATCTGGTGGCCACAGCAGCCAAGCCTAGAGCCCTCCGGATCCCATCCAGGCGCAAAG 5128

AGGAATAGGAGGGACATGGAACCATTTGCCTCTGGCTGTGTCACAGGGTGAGCCCCAAAATTGGGGTTCAGCGTGGGAG 5207

GCCACGTGGATTCTTGGCTTTGTACAGGAAGATCTACAAGAGCAAGCCAACAGAGTAAAGTGGAAGGAAGTTTATTCAG 5286

AAAATAAAGGAGTATCACAGCTCTTTTAGAATTTGTCTAGCAGGCTTTCCAGTTTTTACCAGAAAACCCCTATAAATTA 5365

AAAATTTTTTACTTAAATTTAAGAATTAAAAAAATACAAAAAAGAAAAAATGAAAATAAAGGAATAAGAAGTTACCTAC 5444

AAAATTTTTTACTTAAATTTAAGAATTAAAAAAATACAAAAAAGAAAAAATGAAAATAAAGGAATAAGAAGTTACCTAC 5444

FIG. 1D

```
CTGGTTCTCAACTTCTTTTGAAATAATGTTCATAGAGAAGGAGGGCTGTCTGAGATTCGAGGGAAACAAGCTCTCAGGA      79

CTTCCGGTCGCCATGATGGCTGTGGGCGGTAAACGCGGTTAGTGCAAGCATCTGGGCCATCTTCAATGGTAAAAAAGAT     158

ACAGTAAAGACATAAATACCACATTTGACAAATGGAAAAAAAGGAGTGTCCAGAAAAGAGTAGCAGCAGTGAGGAAGAG     237

CTGCCGAGACGGGTATACAGGGAGCTACCCTGTGTTTCTGAGACCCTTTGTGACATCTCACATTTTTTCCAAGAAG       313
```

|   |   |   |   |   |   |   |   |   |   |   |   |   |   |   |   |   |   |   |   |   |      |
|---|---|---|---|---|---|---|---|---|---|---|---|---|---|---|---|---|---|---|---|---|------|
| M | M | R | Q | R | Q | S | H | Y | C | S | V | L | F | L | S | V | N | Y | L |   | 20   |
| ATG | ATG | AGA | CAG | AGG | CAG | AGC | CAT | TAT | TGT | TCC | GTG | CTG | TTC | CTG | AGT | GTC | AAC | TAT | CTG |   | 373  |
| G | G | T | F | P | G | D | I | C | S | E | E | N | Q | I | V | S | S | Y | A |   | 40   |
| GGG | GGG | ACA | TTC | CCA | GGA | GAC | ATT | TGC | TCA | GAA | GAG | AAT | CAA | ATA | GTT | TCC | TCT | TAT | GCT |   | 433  |
| S | K | V | C | F | E | I | E | E | D | Y | K | N | R | Q | F | L | G | P | E |   | 60   |
| TCT | AAA | GTC | TGT | TTT | GAG | ATC | GAA | GAA | GAT | TAT | AAA | AAT | CGT | CAG | TTT | CTG | GGG | CCT | GAA |   | 493  |
| G | N | V | D | V | E | L | I | D | K | S | T | N | R | Y | S | V | W | F | P |   | 80   |
| GGA | AAT | GTG | GAT | GTT | GAG | TTG | ATT | GAT | AAG | AGC | ACA | AAC | AGA | TAC | AGC | GTT | TGG | TTC | CCC |   | 553  |
| T | A | G | W | Y | L | W | S | A | T | G | L | G | F | L | V | R | D | E | V |   | 100  |
| ACT | GCT | GGC | TGG | TAT | CTG | TGG | TCA | GCC | ACA | GGC | CTC | GGC | TTC | CTG | GTA | AGG | GAT | GAG | GTC |   | 613  |
| T | V | T | I | A | F | G | S | W | S | Q | H | L | A | L | D | L | Q | H | H |   | 120  |
| ACA | GTG | ACG | ATT | GCG | TTT | GGT | TCC | TGG | AGT | CAG | CAC | CTG | GCC | CTG | GAC | CTG | CAG | CAC | CAT |   | 673  |
| E | Q | W | L | V | G | G | P | L | F | D | V | T | A | E | P | E | E | A | V |   | 140  |
| GAA | CAG | TGG | CTG | GTG | GGC | GGC | CCC | TTG | TTT | GAT | GTC | ACT | GCA | GAG | CCA | GAG | GAG | GCT | GTC |   | 733  |
| A | E | I | H | L | P | H | F | I | S | L | Q | G | E | V | D | V | S | W | F |   | 160  |
| GCC | GAA | ATC | CAC | CTC | CCC | CAC | TTC | ATC | TCC | CTC | CAA | GGT | GAG | GTG | GAC | GTC | TCC | TGG | TTT |   | 793  |
| L | V | A | H | F | K | N | E | G | M | V | L | E | H | P | A | R | V | E | P |   | 180  |
| CTC | GTT | GCC | CAT | TTT | AAG | AAT | GAA | GGG | ATG | GTC | CTG | GAG | CAT | CCA | GCC | CGG | GTG | GAG | CCT |   | 853  |
| F | Y | A | V | L | E | S | P | S | F | S | L | M | G | I | L | L | R | I | A |   | 200  |
| TTC | TAT | GCT | GTC | CTG | GAA | AGC | CCC | AGC | TTC | TCT | CTG | ATG | GGC | ATC | CTG | CTG | CGG | ATC | GCC |   | 913  |
| S | G | T | R | L | S | I | P | I | T | S | N | T | L | I | Y | Y | H | P | H |   | 220  |
| AGT | GGG | ACT | CGC | CTC | TCC | ATC | CCC | ATC | ACT | TCC | AAC | ACA | TTG | ATC | TAT | TAT | CAC | CCC | CAC |   | 973  |
| P | E | D | I | K | F | H | L | Y | L | V | P | S | D | A | L | L | T | K | A |   | 240  |
| CCC | GAA | GAT | ATT | AAG | TTC | CAC | TTG | TAC | CTT | GTC | CCC | AGC | GAC | GCC | TTG | CTA | ACA | AAG | GCG |   | 1033 |
| I | D | D | E | E | D | R | F | H | G | V | R | L | Q | T | S | P | P | M | E |   | 260  |
| ATA | GAT | GAT | GAG | GAA | GAT | CGC | TTC | CAT | GGT | GTG | CGC | CTG | CAG | ACT | TCG | CCC | CCA | ATG | GAA |   | 1093 |
| P | L | N | F | G | S | S | Y | I | V | S | N | S | A | N | L | K | V | M | P |   | 280  |
| CCC | CTG | AAC | TTT | GGT | TCC | AGT | TAT | ATT | GTG | TCT | AAT | TCT | GCT | AAC | CTG | AAA | GTA | ATG | CCC |   | 1153 |
| K | E | L | K | L | S | Y | R | S | P | G | E | I | Q | H | F | S | K | F | Y |   | 300  |
| AAG | GAG | TTG | AAA | TTG | TCC | TAC | AGG | AGC | CCT | GGA | GAA | ATT | CAG | CAC | TTC | TCA | AAA | TTC | TAT |   | 1213 |
| A | G | Q | M | K | E | P | I | Q | L | E | I | T | E | K | R | H | G | T | L |   | 320  |
| GCT | GGG | CAG | ATG | AAG | GAA | CCC | ATT | CAA | CTT | GAG | ATT | ACT | GAA | AAA | AGA | CAT | GGG | ACT | TTG |   | 1273 |
| V | W | D | T | E | V | K | P | V | D | L | Q | L | V | A | A | S | A | P | P |   | 340  |
| GTG | TGG | GAT | ACT | GAG | GTG | AAG | CCA | GTG | GAT | CTC | CAG | CTT | GTA | GCT | GCA | TCA | GCC | CCT | CCT |   | 1333 |
| P | F | S | G | A | A | F | V | K | E | N | H | R | Q | L | Q | A | R | M | G |   | 360  |
| CCT | TTC | TCA | GGT | GCA | GCC | TTT | GTG | AAG | GAG | AAC | CAC | CGG | CAA | CTC | CAA | GCC | AGG | ATG | GGG |   | 1393 |
| D | L | K | G | V | L | D | D | L | Q | D | N | E | V | L | T | E | N | E | K |   | 380  |
| GAC | CTG | AAA | GGG | GTG | CTC | GAT | GAT | CTC | CAG | GAC | AAT | GAG | GTT | CTT | ACT | GAG | AAT | GAG | AAG |   | 1453 |
| E | L | V | E | Q | E | K | T | R | Q | S | K | N | E | A | L | L | S | M | V |   | 400  |

FIG. 4A

```
GAG CTG GTG GAG CAG GAA AAG ACA CGG CAG AGC AAG AAT GAG GCC TTC CTG AGC ATG GTG    1513
 E   L   V   E   Q   E   K   T   R   Q   S   K   N   E   A   F   L   S   M   V    420
GAG AAG AAA GGG GAC CTG GCC CTG GAC GTG CTC TTC AGA AGC ATT AGT GAA AGG GAC CCT    1573
 Y   L   V   S   Y   L   R   Q   Q   N   L   *                                    432
TAC CTC GTG TCC TAT CTT AGA CAG CAG AAT TTG TAA                                    1609
AATGAGTCAGTTAGGTAGTCTGGAAGAGAGAATCCAGCGTTCTCATTGGAAATGGATAAACAGAAATGTGATCATTGAT    1688
TTCAGTGTTCAAGACAGAAGAAGACTGGGTAACATCTATCACACAGGCTTTCAGGACAGACTTGTAACCTGGCATGTAC    1767
CTATTGACTGTATCCTCATGCATTTTCCTCAAGAATGTCTGAAGAAGGTAGTAATATTCCTTTTAAATTTTTTCCAACC    1846
ATTGCTTGATATATCACTATTTTATCCATTGACATGATTCTTGAAGACCCAGGATAAAGGACATCCGGATAGGTGTGTT    1925
TATGAAGGATGGGGCCTGGAAAGGCAACTTTTCCTGATTAATGTGAAAAATAATTCCTATGGACACTCCGTTTGAAGTA    2004
TCACCTTCTCATAACTAAAAGCAGAAAAGCTAACAAAAGCTTCTCAGCTGAGGACACTCAAGGCATACATGATGACAGT    2083
CTTTTTTTTTTTTGTATGTTAGGACTTTAACACTTTATCTATGGCTACTGTTATTAGAACAATGTAAATGTATTTGCTG    2162
AAAGAGAGCACAAAAATGGGAGAAAATGCAAACATGAGCAGAAAATATTTTCCCACTGGTGTGTAGCCTGCTACAAGGA    2241
GTTGTTGGGTTAAATGTTCATGGTCAACTCCAAGGAATACTGAGATGAAATGTGGTAAATCAACTCCACAGAACCACCA    2320
AAAAGAAAATGAGGGTAATTCAGCTTATTCTGAGACAGACATTCCTGGCAATGTACCATACAAAAAATAAGCCAACTCT    2399
GACATTTGGATTCTACCATAGACTCTGTCATTTTGTAGCCATTTCAGCTGTCTTTTGATTAATGTTTTCGTGGCACACA    2478
TATTTCCATCCTTTTATGTTTAATCTGTTTAAAACAAGTTCCTAGTAGACACCATCTGGTTGAGTCAGTTTTTTTTTATG    2557
GTGTATTTTGAACCCATTCTGATAGTCTCTTTTAACTGGAAGATTTCAATTACTTACGTTAATGTAATTATTAATATGT    2636
TAGGATTTATCCTCAGTCAGCCAGTTTGTTATGTCTTTTCTATTCTACTGTTATCACATTTGTACCACTTAAAGTGGAA    2715
TCTAGGCACTTTATCACCATTTAGATCCTATTACCTTTTCTCATCTAGGATATAGTTATCTTCTACATAATCTTTCTGT    2794
ATCTTAAAACCCATCAATAAATTATTATATATTTTCTACTTTTAATCACTCAGAAGATTTAAAAAACTCATGAGAAGAG    2873
TAATCTGTTATGTTTTTCCAGATATTTACCATTTCTGTTGCTCTTCCTTCATTATTTTCCAAATTTCGTTCTGCAAATT    2952
TCCACTTCTTCTGATAGACGTTTTTTAGTTCTTTTAGAGTGGTTCTGATAGGTACAGATTCTCTTATTTTTTGCTPCCT    3031
CTGAGGACATCTTTTTCTCACCTTCATTCTCAGTGATGTTTTTTGCTTGTAGTATTTTTAGTTGACATTGTTTTCTGTT    3110
CAGCAGTTTCCTTTTAGCTTCCGTATTTCCTGATGAGAAATCTGCAGTCATTCAAATTGTTGTTTCCCTGTATGTAGTG    3189
TGTCATTTTTCTGTCAGATTTCAAGGTATTTATCTTTAGTTTTTAGCCATTTCATTATGTTGGGGATGAGTTTCCTTGT    3268
TTTATTCCCTTTGGAATTTGCTCCAATTCATAAATTTGCAGTTTTATGTCTTTTACCAAACTTAGAGGTTTTCAGCCTA    3347
ATTTCTAAAAATACTTTTTATTAGCCTGATTTTCATCTTTATAGGAAATAGTTTAAGTGATGACAAGTTCCAATAGCTT    3426
ATATGCCCAGAAGGCCTTCAAAATAAGAATTTTGAAAGAATACAGAAAACAAACTTTTATATCCTTCTCATGTCTTCTA    3505
CTGTAAAATTCATATGCTTTGCTACTCTAAACCTAGTTTGAAATCAACAGTCTTGAGAATAGATGAAAATTTTGATGAA    3584
TAGTGGAATTCTTTTAAATGGAAACCTCTTACATGTGATTTTCCTTGCCATCTAGAAATAAACCATAGTATTTATGTTG    3663
AATCAATCAATATTATATTTTGTTTTTTTCCTCCTCTTCTGAGACTCTTATTGTGGAAATGTTAGACTTTTATGTTTTC    3742
CTAAATGTCCCTGATATTCTACTTATTTAGAACATCTTTTCATTTTTTCCATTATTCTGATTGGGTAATTTTAATTTGT    3821
CTATTTTCAAATTTGCTGGAGTGTTCACCTGTTGTTGTCTGTGTCGTCCCACTGAGTGCATTCACCACCTTTTAAATTT    3900
TGGTCACTGTATGTATCAGTTCTAAAATTTCCATTTTGTTCTCTATATTTTAAATTTCTTGGCTTATATTCTATTTTCC    3979
```

FIG. 4B

```
TGCAAATGTGTCAGCATTTGCTTGTTTGAGCTTTTTTTTTTTCAAGACAGGGTCTCAACTCTGTTACCCAGGCTGGAGT    4058
GCAGTGGTGCGATCTCAGCTCACTGCAACCTCTGCCTCCTGGTTCAAGCGATTATTGTGCCTCAGCCTCCTGAGTAGCT    4137
GGGATTACAGGCATGCACCACCACAGCCCAGCTAATTTTTTGTATTTTTAGTAGAGACAGAGTTTTGCTATGTTGGCCA    4216
GGCTGGTTTTGAACTCCTGGCCTCAAGTGATCCACCCACCTCAGCCTCCCAAAGTGCTGGGATTACAGGCCACTACACC    4295
TGGCACATTTGAGTATTTTTTTTTTTTTTTTTTTTTGAGATGGAGTCTCGCTCTGTCATCTAGGCTGGAGTGCAGTGG    4374
TGTGATCTCAGCTCACTGCAGCCTCTGTCTCCCGGGCTCAAGCGATTCTCTTGCCTCAGCCTCCTGAGTAGCTAGGACT    4453
ACAGGTGCATGCCAACACGCCCGGCTAATTTTTTTAAAAAATATTTTTAGTAGAGACAGGGTTTCACCATTTTGGCCAG    4532
GATGGTCTCGATCTCCTGACCTCATGATCCACCCGCCTCGGCCTTCCAAAGTGCTGGGATTACAGGCATGAGCCACCGT    4611
GCCTGGCCTCATTTGAGTATTTTTATAATGTCTCTTTTAAAGTCTTTGTCAGATAATTCCACTGTACATGTTATTCAGT    4690
GTTTGGTGTCCACTGAGTTGTCATTTGCCAGACAAGTGGAGATTTTTGCAGCTCATCCTTGTATTCTCAGTAGTTCCGA    4769
TATGTACCCTCGACATGTGAATGTTATCTTATGAGACTCTGTTTTATTTGTATCCAACAGAAGATGTTTATTATTTATT    4848
TGGCTTTCTGTGAACTGAGGTCTTAATATCAGCTCATTTTAAAAGTCTTTGCAGTGGTATTCGGATCTATCCTGTGTGT    4927
GCCTATGAGATTGGGTGCAGTGTATCCTGTTAGCTCCATTCTCAGGGCGTTTGAATGTGAATTAGGACCAGCGCAATGA    5006
ATGCTCAAGTTGGGGTTGGGCGTTAGAATTCATAAAAGTCTTTATATGCTCAG    5059
```

FIG. 4C

```
  1 CGCGTCCGGCTGCAGCGGGGTGAGCGGCGGCAGCGGCCGGGGATCCTGGAGCCATGGGGC
    GCGCAGGCCGACGTCGCCCCACTCGCCGCCGTCGCCGGCCCCTAGGACCTCGGTACCCCG
                                                          1▶ M  G

61 GCGCGCGCGACGCCATCCTGGATGCGCTGGAGAACCTGACCGCCGAGGAGCTCAAGAAGT
    CGCGCGCGCTGCGGTAGGACCTACGCGACCTCTTGGACTGGCGGCTCCTCGAGTTCTTCA
  3▶ R  A  R  D  A  I  L  D  A  L  E  N  L  T  A  E  E  L  K  K

121 TCAAGCTGAAGCTGCTGTCGGTGCCGCTGCGCGAGGGCTACGGGCGCATCCCGCGGGGCG
    AGTTCGACTTCGACGACAGCCACGGCGACGCGCTCCCGATGCCCGCGTAGGGCGCCCCGC
 23▶ F  K  L  K  L  L  S  V  P  L  R  E  G  Y  G  R  I  P  R  G

181 CGCTGCTGTCCATGGACGCCTTGGACCTCACCGACAAGCTGGTCAGCTTCTACCTGGAGA
    GCGACGACAGGTACCTGCGGAACCTGGAGTGGCTGTTCGACCAGTCGAAGATGGACCTCT
 43▶ A  L  L  S  M  D  A  L  D  L  T  D  K  L  V  S  F  Y  L  E

241 CCTACGGCGCCGAGCTCACCGCTAACGTGCTGCGCGACATGGGCCTGCAGGAGATGGCCG
    GGATGCCGCGGCTCGAGTGGCGATTGCACGACGCGCTGTACCCGGACGTCCTCTACCGGC
 63▶ T  Y  G  A  E  L  T  A  N  V  L  R  D  M  G  L  Q  E  M  A

301 GGCAGCTGCAGGCGGCCACGCACCAGGGCTCTGGAGCCGCGCCAGCTGGGATCCAGGCCC
    CCGTCGACGTCCGCCGGTGCGTGGTCCCGAGACCTCGGCGCGGTCGACCCTAGGTCCGGG
 83▶ G  Q  L  Q  A  A  T  H  Q  G  S  G  A · A  P  A  G  I  Q  A

361 CTCCTCAGTCGGCAGCCAAGCCAGGCCTGCACTTTATAGACCAGCACCGGGCTGCGCTTA
    GAGGAGTCAGCCGTCGGTTCGGTCCGGACGTGAAATATCTGGTCGTGGCCCGACGCGAAT
103▶ P  P  Q  S  A  A  K  P  G  L  H  F  I  D  Q  H  R  A  A  L

421 TCGCGAGGGTCACAAACGTTGAGTGGCTGCTGGATGCTCTGTACGGGAAGGTCCTGACGG
    AGCGCTCCCAGTGTTTGCAACTCACCGACGACCTACGAGACATGCCCTTCCAGGACTGCC
123▶ I  A  R  V  T  N  V  E  W  L  L  D  A  L  Y  G  K  V  L  T

481 ATGAGCAGTACCAGGCAGTGCGGGCCGAGCCCACCAACCCAAGCAAGATGCGGAAGCTCT
    TACTCGTCATGGTCCGTCACGCCCGGCTCGGGTGGTTGGGTTCGTTCTACGCCTTCGAGA
143▶ D  E  Q  Y  Q  A  V  R  A  E  P  T  N  P  S  K  M  R  K  L

541 TCAGTTTCACACCAGCCTGGAACTGGACCTGCAAGGACTTGCTCCTCCAGGCCCTAAGGG
    AGTCAAAGTGTGGTCGGACCTTGACCTGGACGTTCCTGAACGAGGAGGTCCGGGATTCCC
163▶ F  S  F  T  P  A  W  N  W  T  C  K  D  L  L  L  Q  A  L  R

601 AGTCCCAGTCCTACCTGGTGGAGGACCTGGAGCGGAGCTGAGGCTCCTTCCCAGCAACAC
    TCAGGGTCAGGATGGACCACCTCCTGGACCTCGCCTCGACTCCGAGGAAGGGTCGTTGTG
183▶ E  S  Q  S  Y  L  V  E  D  L  E  R  S

661 TCCGGTCAGCCCCTGGCAATCCCACCAAATCATCCTGAATCTGATCTTTTTTATACACAAT
    AGGCCAGTCGGGGACCGTTAGGGTGGTTTAGTAGGACTTAGACTAGAAAAATATGTGTTA

721 ATACGAAAAGCCAGCTTGAA
    TATGCTTTTCGGTCGAACTT
```

FIG. 7

MOLECULES OF THE CARD-RELATED PROTEIN FAMILY AND USES THEREOF

CROSS REFERENCE TO RELATED APPLICATIONS

This application is a continuation-in-part of: U.S. application Ser. No. 09/931,071, filed Aug. 15, 2001, which is a continuation-in-part of U.S. application Ser. No. 09/428,252, filed Oct. 27, 1999 now abandoned; and U.S. application Ser. No. 09/340,620, filed Jun. 28, 1999 now U.S. Pat. No. 6,482,933. The contents of each of these applications is incorporated herein by reference.

BACKGROUND OF THE INVENTION

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. For many years, the magnitude of apoptotic cell death was not appreciated because the dying cells are quickly eliminated by phagocytes, without an inflammatory response.

The mechanisms that mediate apoptosis have been intensively studied. These mechanisms involve the activation of endogenous proteases, loss of mitochondrial function, and structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved from worms, such as C. elegans, to humans. In fact, invertebrate model systems have been invaluable tools in identifying and characterizing the genes that control apoptosis. Through the study of invertebrates and more evolved animals, numerous genes that are associated with cell death have been identified, but the way in which their products interact to execute the apoptotic program is poorly understood.

Caspases, a class of proteins central to the apoptotic program, are responsible for the degradation of cellular proteins that leads to the morphological changes seen in cells undergoing apoptosis. Caspases are cysteine proteases having specificity for aspartate at the substrate cleavage site. An effector caspase is activated by an initiator caspase which cleaves the effector caspase at specific internal aspartate residues resulting in the separation of the large and small subunits of the effector caspase. For example, one of the caspases identified in humans was previously known as the interleukin-1 (IL-1α) converting enzyme (ICE), a cysteine protease responsible for the processing of pro-IL-1α to the active cytokine. Overexpression of ICE in Rat-1 fibroblasts induces apoptosis (Miura et al., Cell 75:653, 1993).

Many caspases and proteins that interact with caspases possess domains of about 60 amino acids called a caspase recruitment domain (CARD domain). Hofmann et al. (TIBS 22:155, 1997) and others have postulated that certain apoptotic proteins bind to each other via their CARD domains and that different subtypes of CARD domains may confer binding specificity, regulating the activity of various caspases, for example. The functional significance of CARD domains has been repeatedly demonstrated. For example, Duan et al. (Nature 385:86, 1997) showed that deleting the CARD at the N-terminus of RAIDD abolished the ability of RAIDD to bind to caspases. The interaction of protein through their CARD domains may inhibit apoptosis. For example, CARD domain containing proteins may interact with cIAP-1 and cIAP2 via CARD domain interaction and activate the anti-apoptotic activity of cIAP-1 and cIAP-2. In addition, CARD domain interaction is thought to play a role in NF-κB activation.

Caspase-9 activation may precede the activation of all other cell death-related caspases in the mitochondrial pathways of apoptosis (Slee et al., J. Cell Biol. 144:281–292, 1999). Inactive procaspase-9 is activated by interaction with a complex which includes Apaf-1, a CARD-containing protein, and other factors (Li et al., Cell 91:479, 1997; Srinivasula et al., Mol. Cell 1:949–959, 1998). Recognition of procaspase-9 by Apaf-1 occurs primarily through the interaction of the CARD of Apaf-1 with the prodomain of caspase-9. The CARD of Apaf-1 shares about 20% sequence identity with the prodomain of procaspase-9. The prodomain of caspase-9 is a member of the CARD family of apoptotic signaling motifs (Hofinann and Bucher, Trends in Biochem. Sci. 22:155–156, 1997). A similar domain is present in caspase activating proteins CED-4 and RAIDD/CRADD as well as in initiator caspases CED-3 and caspase-2/ICH-1 (Duan and Dixit, Nature 385:86–89, 1997; Ahmad et al., Cancer Res. 57:615–619, 1997; Alnemri et al., Cell 87:171, 1996). Apaf-1 can bind several other caspases, e.g., caspase-4 and caspase-8 (Inohara et al., J. Biol. Chem. 273:12296–12300, 1998).

Nuclear factor-B (NF-κB) is a transcription factor expressed in many cell types and which activates homologous or heterologous genes that have NF-κB sites in their promoters. Molecules that regulate NF-κB activation play a critical role in both apoptosis and inflammation. Quiescent NF-κB resides in the cytoplasm as a heterodimer of proteins referred to as p50 and p65 and is complexed with the regulatory protein IκB. NF-κB binding to IκB causes NF-κB to remain in the cytoplasm. At least two dozen stimuli that activate NF-κB are known (New England Journal of Medicine 336:1066, 1997) and they include cytokines, protein kinase C activators, oxidants, viruses, and immune system stimuli. NF-κB activating stimuli activate specific IκB kinases that phosphorylate IκB leading to its degradation. Once liberated from IκB, NF-κB translocates to the nucleus and activates genes with κB sites in their promoters. The proinflammatory cytokines TNF-α and IL-1 induce NF-κB activation by binding their cell-surface receptors and activating the NF-κB-inducing kinase, NIK, and NF-κB. NIK phosphorylates the IκB kinases α and β which phosphorylate IκB, leading to its degradation.

Interactions between proteins having CARD domain can lead to the activation of NF-κB. Moreover, activation of NF-κB has bee correlated with both activation and inhibition of apoptotic signaling pathways.

NF-κB and the NF-κB pathway has been implicated in mediating chronic inflammation in inflammatory diseases such as asthma, ulcerative colitis, rheumatoid arthritis (Epstein, New England Journal of Medicine 336:1066, 1997) and inhibiting NF-κB or NF-κB pathways may be an effective way of treating these diseases. NF-κB and the NF-κB pathway has also been implicated in atherosclerosis (Navab et al., American Journal of Cardiology 76:1 8C, 1995), especially in mediating fatty streak formation, and inhibiting NF-κB or NF-κB pathways may be an effective therapy for atherosclerosis. Among the genes activated by NF-κB are cIAP-1, cIAP-2, TRAF1, and TRAF2, all of which have been shown to protect cells from TNF-α induced cell death (Wang et al., Science 281:1680–83, 1998). CLAP, a protein which includes a CARD, activates the Apaf-1-caspase-9 pathway and activates NF-κB by acting upstream of NIK and IκB kinase (Srinivasula et al., supra).

Bcl-2 family proteins are important regulators of pathways involved in apoptosis and can act to inhibit or promote cell death. Expression of certain anti-apoptotic Bcl-2 family members is commonly altered in cancerous cells, suppressing programmed cell death and extending tumor growth. Among the anti-apoptotic Bcl-2 family members thus far identified are Boo, Bcl-2, Bcl-xL, Bcl-w, NR-13, A1, and Mcl-2. Pro-apoptotic Bcl-2 family members include Bax, Bak, Bad, Bik, Bid, Hrk, Bim, and Bok/Mtd. Significantly, the anti-apoptotic Bcl-2 family member, Bcl-xL, has been shown to interact with Apaf-1 and block Apaf-1-dependent caspase-9 activation (Hu et al., Proc. Nat'l. Acad. Sci. 95:4386–4391, 1998). Boo, another anti-apoptotic Bcl-2 family member, interacts with Apaf-1 and caspase-9. Bak and Bik, pro-apoptotic Bcl-2 family members, can disrupt the association of Boo with Apaf-1 (Song et al., EMBO J. 18:167–178, 1999). Boo is thought to be involved in the control of ovarian atresia and sperm maturation. Diva, another member of the Bcl-2 family, inhibits binding of Bcl-xL to Apf-1, preventing Bcl-xL from binding to Apaf-1.

Neurotrophins (e.g., NGF), which are best known as neuronal survival factors, can mediate apoptosis via the p75 neurotrophin receptor (p75NTR). It is thought that p75NTR activation can lead to NF-κB activation (Carter et al., Science 272:542–545, 1996). It has been proposed that p75NTR -mediated cell death acts to ensure rapid cell death when a neuron is unable to obtain sufficient neurotropins. This mechanism could, for example, cause the elimination of neurons that reach an inappropriate target or that reach an appropriate target at an inappropriate time (Miller and Kaplan, Cell Death and Diff. 5:343–345, 1998).

SUMMARY OF THE INVENTION

The present invention is based, at least in part, on the identification of genes encoding human CARD-7 and human CARD-8, both of which are predicted to be involved in regulating caspase activity.

The 5445 nucleotide CARD-7 cDNA described below (SEQ ID NO:1) has a 4287 nucleotide open reading frame (nucleotides 523 to 4809 of SEQ ID NO: 1; SEQ ID NO:5) which encodes a 1429 amino acid protein (SEQ ID NO:2). The nucleotide and predicted amino acid sequence of the CARD-7 cDNA are depicted in FIGS. 1A–1D. CARD-7 is predicted to be an intracellular protein. CARD-7 contains a nucleotide binding domain at amino acids 329–645 of SEQ ID NO:2. Within this domain there is a kinase 1A (P loop; Walker Box A subdomain) subdomain at amino acids 333–341 of SEQ ID NO:2; a kinase 2 subdomain (Walker Box B subdomain) at amino acids 404–413 of SEQ ID NO:2; a kinase 3a subdomain at amino acids 454–463 of SEQ ID NO:2; and a motif 2 domain at amino acids 615–622 of SEQ ID NO:2. CARD-7 also contains six leucine rich domains (amino acids 807–834; 836–863; 864–891; 893–920; 921–948; and 950–976 of SEQ ID NO:2). CARD-7 has a CARD domain at amino acids 1335–1429 of SEQ ID NO:2.

The 5059 nucleotide CARD-8 cDNA described below (SEQ ID NO:3) has a 1293 nucleotide open reading frame (nucleotides 314–1606 of SEQ ID NO:3) which encodes a 431 amino acid protein (SEQ ID NO:4). The nucleotide and predicted amino acid sequence of the CARD-8 cDNA are depicted in FIGS. 4A–4D. CARD-8 is predicted to be an intracellular protein. CARD-8 has a CARD domain at amino acids 348–431 of SEQ ID NO:2.

CARD-7 and CARD-8 include domains and subdomains that are similar to domains and subdomains found in CARD-3, CARD-4, CARD-5, and CARD-6. Detailed information concerning CARD-3, CARD-4, CARD-5, and CARD-6 can be found in U.S. application Ser. No. 09/245,281, filed Feb. 5, 1999, U.S. application Ser. No. 09/207,359, filed Dec. 8, 1998, U.S. application Ser. No. 09/099,041, filed Jun. 17, 1998, U.S. application Ser. No. 09/019,942, filed Feb. 6, 1998, and U.S. application Ser. No. 09/340,620, filed Jun. 28, 1999. The entire content of each of these applications is incorporated herein by reference.

Like other proteins containing a CARD domain, CARD-7 and CARD-8, likely participate in the network of interactions that modulate caspase activity. CARD-7 and CARD-8 molecules are useful as modulating agents in regulating a variety of cellular processes including cell growth and cell death.

The invention encompasses methods of diagnosing and treating patients who are suffering from a disorder associated with an abnormal level or rate (undesirably high or undesirably low) of apoptotic cell death, abnormal activity of the Fas/APO-1 receptor complex, abnormal activity of the TNF receptor complex, or abnormal activity of a caspase by administering a compound that modulates the expression of CARD-7 or CARD-8 (at the DNA, mRNA or protein level, e.g., by altering mRNA splicing) or by altering the activity of CARD-7 or CARD-8. Examples of such compounds include small molecules, antisense nucleic acid molecules, ribozymes, and polypeptides.

Certain disorders are associated with an increased number of surviving cells, which are produced and continue to survive or proliferate when apoptosis is inhibited or occurs at an undesirably low rate. Compounds that modulate the expression or activity of CARD-7 or CARD-8 can be used to treat or diagnose such disorders. These disorders include cancer (particularly follicular lymphomas, chronic myelogenous leukemia, melanoma, colon cancer, lung carcinoma, carcinomas associated with mutations in p53, and hormone-dependent tumors such as breast cancer, prostate cancer, and ovarian cancer). Such compounds can also be used to treat viral infections (such as those caused by herpesviruses, poxviruses, and adenoviruses). Failure to remove autoimmune cells that arise during development or that develop as a result of somatic mutation during an immune response can result in autoimmune disease. Thus, certain autoimmune disorders can be caused by an undesirably low level of apoptosis. Accordingly, modulators of CARD-7 or CARD-8 activity or expression can be used to treat autoimmune disorders (e.g., systemic lupus erythematosis, immune-mediated glomerulonephritis, and arthritis).

Many diseases are associated with an undesirably high rate of apoptosis. Modulators of CARD-7 or CARD-8 expression or activity can be used to treat or diagnose such disorders. For example, populations of cells are often depleted in the event of viral infection, with perhaps the most dramatic example being the cell depletion caused by the human immunodeficiency virus (HIV). Surprisingly, most T cells that die during HIV infections do not appear to be infected with HIV. Although a number of explanations have been proposed, recent evidence suggests that stimulation of the CD4 receptor results in the enhanced susceptibility of uninfected T cells to undergo apoptosis. A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

Proteins containing a CARD domain are thought to be involved in various inflammatory disorders. Accordingly, CARD-7 and CARD-8 polypeptides, nucleic acids and modulators of CARD-7 or CARD-8 expression or activity can be used to treat immune disorders. Such immune disorders include, but are not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, and bacterial infections, including tuberculosis and lepromatous leprosy.

In addition to the aforementioned disorders, CARD-7 and CARD-8 polypeptides, nucleic acids, and modulators of CARD-7 or CARD-8 expression or activity can be used to treat disorders of cell signaling and disorders of tissues in which CARD-7 or CARD-8 is expressed.

The present invention provides a method for detecting the presence of CARD-7 or CARD-8 activity or expression in a biological sample by contacting the biological sample with an agent capable of detecting an indicator of CARD-7 or CARD-8 activity such that the presence of CARD-7 or CARD-8 activity is detected in the biological sample. These methods can be used to detect a variety of disorders, e.g., the disorders discussed above.

In another aspect, the invention provides a method for modulating CARD-7 or CARD-8 activity comprising contacting a cell with an agent that modulates (inhibits or stimulates) CARD-7 or CARD-8 activity or expression such that CARD-7 or CARD-8 activity or expression in the cell is modulated. In one embodiment, the agent is an antibody that specifically binds to CARD-7 or CARD-8 protein. In another embodiment, the agent modulates expression of CARD-7 or CARD-8 by modulating transcription of a CARD-7 or CARD-8 gene, splicing of a CARD-7 or CARD-8 mRNA, or translation of a CARD-7 or CARD-8 mRNA. In yet another embodiment, the agent is a nucleic acid molecule having a nucleotide sequence that is antisense to the coding strand of the CARD-7 or CARD-8 mRNA or the CARD-7 or CARD-8 gene.

In one embodiment, the methods of the present invention are used to treat a subject having a disorder characterized by aberrant CARD-7 or CARD-8 protein or nucleic acid expression or activity or related to CARD-7 or CARD-8 expression or activity by administering an agent which is a CARD-7 or CARD-8 modulator to the subject. In one embodiment, the CARD-7 or CARD-8 modulator is a CARD-7 or CARD-8 protein. In another embodiment the CARD-7 or CARD-8 modulator is a CARD-7 or CARD-8 nucleic acid molecule. In other embodiments, the CARD-7 or CARD-8 modulator is a peptide, peptidomimetic, or other small molecule.

The present invention also provides a diagnostic assay for identifying the presence or absence of a genetic lesion or mutation characterized by at least one of: (i) aberrant modification or mutation of a gene encoding a CARD-7 or CARD-8 protein; (ii) mis-regulation of a gene encoding a CARD-7 or CARD-8 protein; (iii) aberrant RNA splicing; and (iv) aberrant post-translational modification of a CARD-7 or CARD-8 protein, wherein a wild-type form of the gene encodes a protein with a CARD-7 or CARD-8 activity.

In another aspect, the invention provides a method for identifying a compound that binds to or modulates the activity of a CARD-7 or CARD-8 protein. In general, such methods entail measuring a biological activity of a CARD-7 or CARD-8 protein in the presence and absence of a test compound and identifying those compounds that alter the activity of the CARD-7 or CARD-8 protein.

The invention also features methods for identifying a compound that modulates the expression of CARD-7 or CARD-8 by measuring the expression of CARD-7 or CARD-8 in the presence and absence of a compound.

Other features and advantages of the invention will be apparent from the following detailed description and claims.

BRIEF DESCRIPTION OF THE DRAWINGS

FIGS. 1A–1D depict the cDNA sequence (SEQ ID NO:1) and predicted amino acid sequence (SEQ ID NO:2) of human CARD-7. The methionine-initiated open reading frame of human CARD-7 (nucleotides 523 to 4809 of SEQ ID NO:1) is shown in SEQ ID NO:5.

FIGS. 4A–4C depict the cDNA sequence (SEQ ID NO:3) and predicted amino acid sequence (SEQ ID NO:4) of human CARD-8. The methionine-initiated open reading frame of human CARD-8 (nucleotides 314 to 1606 of SEQ ID NO:3) is shown in SEQ ID NO:6.

FIG. 7 depicts the nucleotide sequence of a human CARD-5 cDNA (SEQ ID NO:7). The open reading frame of this cDNA extends from nucleotide 54 to nucleotide 638 of SEQ ID NO:7 (SEQ ID NO:9) and encodes a 195 amino acid protein SEQ ID NO:8). The complementary strand of SEQ ID NO:7 is shown in SEQ ID NO:10.

DETAILED DESCRIPTION OF THE INVENTION

Figure 2:
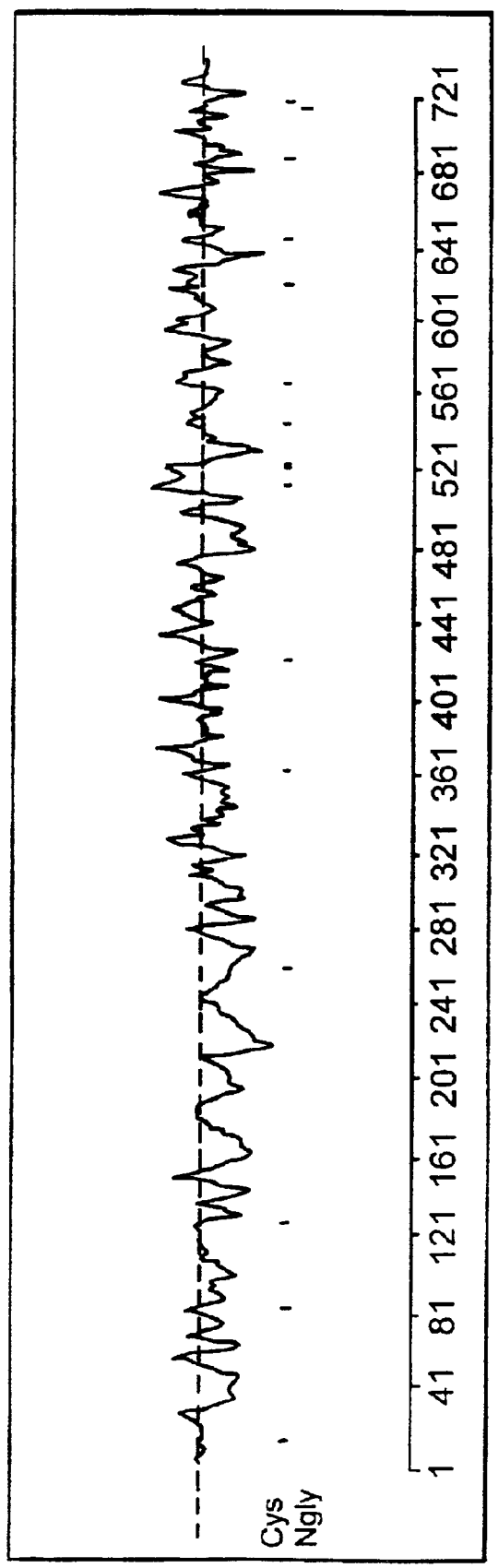
FIG. 2 depicts a hydropathy plot of human CARD-7. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.

The present invention is based, in part, on the identification of cDNA molecules encoding human CARD-7 and human CARD-8.

Identification of CARD-7

A cDNA encoding CARD-7 was identified by searching public protein sequence databases with an amino acid sequence based on the sequence of the CARD domain of CARD-5. CARD-5 is described in U.S. application Ser. No. 09/340,620, filed Jun. 28, 1999.

This analysis led to the identification of a clone (KIAA0926; AB023143; Nagase et al. (1999) DNA Res. 6:63–70) that appeared to encode a protein, later designated CARD-7, possessing a CARD domain.

The 5445 nucleotide CARD-7 cDNA described below (SEQ ID NO:1) has a 4287 nucleotide open reading frame (nucleotides 523 to 4809 of SEQ ID NO: 1; SEQ ID NO:5) which encodes a 1429 amino acid protein (SEQ ID NO:2). The nucleotide and predicted amino acid sequence of the CARD-7 cDNA are depicted in FIGS. 1A–1D. CARD-7 is predicted to be an intracellular protein. CARD-7 contains a nucleotide binding domain at amino acids 329–645 of SEQ ID NO:2. Within this domain there is a kinase 1A (P loop) subdomain at amino acids 333–341 of SEQ ID NO:2; a kinase 2 subdomain at amino acids 404–413 of SEQ ID NO:2; a kinase 3a subdomain at amino acids 454–463 of SEQ ID NO:2; and a motif 2 domain at amino acids 615–622 of SEQ ID NO:2. CARD-7 also contains six leucine rich domains (amino acids 807–834; 836–863; 864–891; 893–920; 921–948; and 950–976 of SEQ ID NO:2). CARD-7 has a CARD domain at amino acids 1335–1429 of SEQ ID NO:2.

Identification of CARD-8

A cDNA encoding CARD-8 was identified by searching public protein sequence databases with an amino acid sequence based on the sequence of the CARD domain of CARD-5. CARD-5 is described in U.S. application Ser. No. 09/340,620, filed Jun. 28, 1999.

This analysis led to the identification of a clone (KIAA0955; AB023172; Nagase et al. (1999) DNA Res. 6:63–70) that appeared to encode a protein, later designated CARD-8, possessing a CARD domain.

The 5059 nucleotide CARD-8 cDNA described below (SEQ ID NO:3) has a 1293 nucleotide open reading frame (nucleotides 314–1606 of SEQ ID NO:3) which encodes a 431 amino acid protein (SEQ ID NO:4). The nucleotide and predicted amino acid sequence of the CARD-8 cDNA are depicted in FIGS. 4A–4D. CARD-8 is predicted to be an intracellular protein. CARD-8 has a CARD domain at amino acids 348–431 of SEQ ID NO:4.

TABLE 1

Summary of CARD-7 and CARD-8 Sequence Information.

| Gene | cDNA | Protein | ORF | Figure |
| --- | --- | --- | --- | --- |
| human CARD-7 | SEQ ID NO: 1 | SEQ ID NO: 2 | SEQ ID NO: 5 | FIGS. 1A–1D |
| human CARD-8 | SEQ ID NO: 3 | SEQ ID NO: 4 | SEQ ID NO: 6 | FIGS. 3A–3D |

CARD-5

CARD-5 is described in detail in U.S. application Ser. No. 09/340,620, filed Jun. 28, 1999. A 740 nucleotide sequence encoding a human CARD-5 protein is shown in FIG. 7 (SEQ ID NO:7; SEQ ID NO:9 includes the open reading frame only). A predicted 195 amino acid sequence of human CARD-5 protein is also shown in FIG. 7 (SEQ ID NO:8). Human CARD-5 contains a CARD domain which extends from amino acid 111 to amino acid 181 of SEQ ID NO:8.

Identification of an Interaction Between CARD-7 and CARD-5

A mammalian two-hybrid screening assay revealed that CARD-7 interacts with CARD-5.

The Stratagene® Mammalian Two-Hybrid Assay Kit (Stratagene, Inc; La Jolla, Calif.) was used to prepare a vector expressing a protein (Gal4-BD/CARD-7) consisting of the DNA binding domain of yeast Gal4 (amino acids 1–147) fused to full-length human CARD-7. In addition, a library of DNA sequences encoding CARD domains was used to create a library of expression vectors encoding the murine NF-κB transcriptional activation domain (amino acids 364–550) fused to a CARD domain (NF-κB-AD/CARD). The Gal4-BD/CARD-7 vector, the NF-κB-AD/CARD domain vector library, and a luciferase reporter construct were introduced into human 293T embryonic kidney cells. If a given CARD domain expressed fused to the NF-κB transcriptional activation domain interacts with CARD-7, the NF-κB transcriptional activation domain will be brought into proximity with the promoter controlling luciferase expression, activating luciferase expression and permitting detection of the interaction. This analysis revealed that CARD-7 interacts with the CARD domain of CARD-5.

CARD-7 and CARD-5 could be involved in modulating the activity of caspase-1 (ICE). For example, CARD-5 may act as an inhibitor or activator of caspase-1 activity (e.g., by binding to caspase-1) and CARD-7 could be a co-inhibitor of caspase-1 through its interaction with CARD-5. Alternatively, CARD-7 might interfere with inhibition or activation of caspase-1 by CARD-5. The mammalian two-hybrid screening assay described above can be used to identify compounds that modulate the interaction between CARD-5 and CARD-7 and thus identify potential useful modulators of caspase, e.g., caspase-1, activity as well as modulators of apoptosis and immune response. Because caspase-1 plays a role in amyotropic lateral sclerosis and cerebral ischemia-induced injury, CARD-7 (and potentially CARD-8) polypeptides and nucleic acids, as well as modulators of CARD-7 (or CARD-8) activity or expression can be used to treat various neurodegenerative disorders and various inflammatory disorders of the central and peripheral nervous system.

Each of CARD-7 and CARD-8 are members of a family of molecules (the CARD-7 family and the CARD-8 family, respectively) having certain conserved structural and functional features. The term "family" when referring to the protein and nucleic acid molecules of the invention is intended to mean two or more proteins or nucleic acid molecules having a common structural domain and having sufficient amino acid or nucleotide sequence identity as defined herein. Such family members can be naturally occurring and can be from either the same or different species. For example, a family can contain a first protein of human origin and a homologue of that protein of murine origin, as well as a second, distinct protein of human origin and a murine homologue of that protein. Members of a family may also have common functional characteristics.

CARD-7 or CARD-8 proteins useful in the methods of the invention include a CARD domain having at least about 65%, preferably at least about 75%, and more preferably about 85%, 95%, or 98% amino acid sequence identity to the CARD domain of CARD-7 or CARD-8.

Useful CARD-7 polypeptides can also include an amino acid sequence sufficiently identical to one or more of the following domains: the nucleotide binding domain, the kinase 1A subdomain, the kinase 2 subdomain, the kinsae 3A subdomain, a motif 2 domain, a leucine rich repeat, and a CARD domain.

As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

As used interchangeably herein a "CARD-7 or CARD-8 activity", "biological activity of CARD-7 or CARD-8" or "functional activity of CARD-7 or CARD-8", refers to an activity exerted by a CARD-7 or CARD-8 protein, polypeptide or nucleic acid molecule on a CARD-7 or CARD-8 responsive cell as determined in vivo, or in vitro, according to standard techniques. A CARD-7 or CARD-8 activity can be a direct activity, such as an association with or an enzymatic activity on a second protein or an indirect activity, such as a cellular signaling activity mediated by interaction of the CARD-7 or CARD-8 protein with a second protein.

A CARD-7 activity includes at least one or more of the following activities: (i) the ability to interact with proteins in an apoptotic signaling pathway (ii) the ability to interact with a CARD-7 ligand; (iii) the ability to interact with an intracellular target protein; (iv) the ability to interact, directly or indirectly with one or more with caspases; (v) the ability to modulate the activity of a caspase, e.g., caspase-9; (vi) the ability to modulate the activity of NF-κB; (vii) the ability to modulate Apaf-1; (viii) the ability to modulate caspase-1; and (ix) the ability interact with CARD-5.

A CARD-8 activity includes at least one or more of the following activities: (i) the ability to interact with proteins in an apoptotic signaling pathway (ii) the ability to interact with a CARD-8 ligand; (iii) the ability to interact with an intracellular target protein; (iv) the ability to interact, directly or indirectly with one or more with caspases; (v) the ability to modulate the activity of a caspase, e.g., caspase-9; (vi) the ability to modulate the activity of NF-κB; and (vii) the ability to modulate caspase-1.

CARD-7 and CARD-8, as well as modulators of CARD-7 or CARD-8 expression or activity can be used to treat disorders associated with inappropriate apoptosis in tissues in which they are expressed (e.g., disorders of the heart, lund, brain, liver,kidney, pancreas, spleen, testis, ovary, smooth muscle, and spinal cord).

Various aspects of the invention are described in further detail in the following subsections.

I. Isolated Nucleic Acid Molecules

One aspect of the invention pertains to methods which employ isolated nucleic acid molecules that encode CARD-7 or CARD-8 proteins or biologically active portions thereof, as well as nucleic acid molecules sufficient for use as hybridization probes to identify CARD-7 or CARD-8-encoding nucleic acids (e.g., CARD-7 or CARD-8 mRNA) and fragments for use as PCR primers for the amplification or mutation of CARD-7 or CARD-8 nucleic acid molecules. As used herein, the term "nucleic acid molecule" is intended to include DNA molecules (e.g., CDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one that is separated from other nucleic acid molecules which are present in the natural source of the nucleic acid. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated CARD-7 or CARD-8 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule useful in the present invention, e.g., a nucleic acid molecule having the nucleotide sequence of SEQ ID NO:1, SEQ ID NO:3, SEQ ID NO:5, and SEQ ID NO:6, or a complement of any of these nucleotide sequences, can be isolated using standard molecular biology techniques and the sequence information provided herein. Using all or portion of the nucleic acid sequences of SEQ ID NO:1, SEQ ID NO:3, SEQ ID NO:5, or SEQ ID NO:6, as a hybridization probe, CARD-7 or CARD-8 nucleic acid molecules can be isolated using standard hybridization and cloning techniques (e.g., as described in Sambrook et al., eds., Molecular Cloning: A Laboratory Manual. 2nd, ed., Cold Spring Harbor Laboratory, Cold Spring Harbor Laboratory Press, Cold Spring Harbor, N.Y., 1989).

A useful nucleic acid molecule can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to CARD-7 or CARD-8 nucleotide sequences can be prepared by standard synthetic techniques, e.g., using an automated DNA synthesizer.

A useful nucleic acid molecule can comprise only a portion of a nucleic acid sequence encoding CARD-7 or CARD-8, for example, a fragment which can be used as a probe or primer or a fragment encoding a biologically active portion of CARD-7 or CARD-8. The nucleotide sequence determined from the cloning of the human CARD-7 or CARD-8 gene allows for the generation of probes and primers designed for use in identifying and/or cloning CARD-7 or CARD-8 homologues in other cell types, e.g., from other tissues, as well as CARD-7 or CARD-8 homologues and orthologs from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1, SEQ ID NO:3, SEQ ID NO:5, or SEQ ID NO:6, or of a naturally occurring mutant of one of SEQ ID NO:1, SEQ ID NO:3, SEQ ID NO:5, and SEQ ID NO:6.

Probes based on the CARD-7 or CARD-8 nucleotide sequence can be used to detect transcripts or genomic sequences encoding the same or similar proteins. The probe comprises a label group attached thereto, e.g., a radioisotope, a fluorescent compound, an enzyme, or an enzyme co-factor. Such probes can be used as a part of a diagnostic test kit for identifying allelic variants and orthologs of the CARD-7 or CARD-8 proteins, identifying cells or tissue which mis-express a CARD-7 or CARD-8 protein, such as by measuring a level of a CARD-7 or CARD-8-encoding nucleic acid in a sample of cells from a subject, e.g., detecting CARD-7 or CARD-8 mRNA levels or determining whether a genomic CARD-7 or CARD-8 gene has been mutated or deleted.

A nucleic acid fragment encoding a "biologically active portion" of CARD-7 or CARD-8 can be prepared by isolating a portion of SEQ ID NO:1, SEQ ID NO:3, SEQ ID NO:5, or SEQ ID NO:6, which encodes a polypeptide having a CARD-7 or CARD-8 biological activity, expressing the encoded portion of CARD-7 or CARD-8 protein (e.g., by recombinant expression in vitro) and assessing the activity of the encoded portion of CARD-7 or CARD-8. For example, a nucleic acid fragment encoding a biologically active portion of CARD-7 or CARD-8 includes a CARD domain.

Also useful are nucleic acid molecules that differ from the nucleotide sequence of SEQ ID NO:1, SEQ ID NO:3, SEQ ID NO:5, or SEQ ID NO:6, due to degeneracy of the genetic code and thus encode the same CARD-7 or CARD-8 protein as that encoded by the nucleotide sequence shown in SEQ ID NO:1, SEQ ID NO:3, SEQ ID NO:5, or SEQ ID NO:6. In addition to the CARD-7 or CARD-8 nucleotide sequences shown in SEQ ID NO:1, SEQ ID NO:3, SEQ ID NO:5, and SEQ ID NO:6, it will be appreciated by those skilled in the art that DNA sequence polymorphisms that lead to changes in the amino acid sequences of CARD-7 or CARD-8 may exist within a population (e.g., the human population). Such genetic polymorphism in the CARD-7 or CARD-8 gene may exist among individuals within a population due to natural allelic variation. As used herein, the terms "gene" and "recombinant gene" refer to nucleic acid molecules comprising an open reading frame encoding a CARD-7 or CARD-8 protein, preferably a mammalian CARD-7 or CARD-8 protein. Such natural allelic variations can typically result in 1–5% variance in the nucleotide sequence of the CARD-7 or CARD-8 gene. Thus, e.g., 1%, 2%, 3%, 4%, or 5% (e.g., 1, 2, 3, 4, 5, 8, 10, 12, 14, or 15, or 20) of the amino acids in CARD-7 or CARD-8 are replaced by another amino acid, preferably by conservative substitution.

Moreover, nucleic acid molecules encoding CARD-7 or CARD-8 proteins from other species (CARD-7 or CARD-8 orthologs/homologues), which have a nucleotide sequence which differs from that of a CARD-7 or CARD-8 disclosed herein, are also useful in the methods of the invention.

Nucleic acid molecules corresponding to natural allelic variants and homologues of the CARD-7 or CARD-8 cDNA can be isolated based on their similarity to the nucleic acids disclosed herein using the human or murine cDNAs, or a portion thereof, as a hybridization probe according to standard hybridization techniques under stringent hybridization conditions.

Useful isolated nucleic acid molecules can be at least 100 (150, 200, 250, 300, 325, 350, 375, 400, 425, 450, 500, 550, 600, 650, 700, 800, 900, 1000, 1300, 1600, 2000, 2500, 3000, 3500, 4000, 4500, or 5000) nucleotides in length and hybridize under stringent conditions to the nucleic acid molecule comprising the nucleotide sequence, preferably the coding sequence, of SEQ ID NO:1, SEQ ID NO:5, SEQ ID NO:3 or SEQ ID NO:6.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1–6.3.6. An, non-limiting example of stringent hybridization conditions are hybridization in 6X sodium chloride/sodium citrate (SSC) at about 45° C., followed by one or more washes in 0.2 X SSC, 0.1% SDS at 50–65 C. (e.g., 50 C. or 60° C. or 65° C.). Preferably, the isolated nucleic acid molecule that hybridizes under stringent conditions corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the CARD-7 or CARD-8 sequence that may exist in the population, the skilled artisan will further appreciate that changes can be introduced by mutation into the nucleotide sequence of SEQ ID NO: 1, SEQ ID NO:3, SEQ ID NO:5, or SEQ ID NO:6, thereby leading to changes in the amino acid sequence of the encoded protein without altering the functional ability of the protein. For example, one can make nucleotide substitutions leading to amino acid substitutions at "non-essential" amino acid residues. A "non-essential" amino acid residue is a residue that can be altered from the wild-type sequence of CARD-7 or CARD-8 protein without altering the biological activity, whereas an "essential" amino acid residue is required for biological activity. For example, amino acid residues that are conserved between the CARD-7 or CARD-8 proteins of various species are predicted to be relatively unamenable to alteration.

For example, useful CARD-7 and CARD-8 proteins can contain at least one CARD domain. Additionally, a CARD-7 protein also contains at least one of: a nucleotide binding domain, a kinase 1A subdomain, a kinase 2 subdomain, a kinsase 3A subdomain, a motif 2 domain, a leucine-rich repeat, and a CARD domain. Such conserved domains are less likely to be amenable to mutation. Other amino acid residues, however, (e.g., those that are not conserved or only semi-conserved among CARD-7 or CARD-8 of various species) may not be essential for activity and thus are more likely to be amenable to alteration.

Other useful nucleic acid molecules encoding CARD-7 or CARD-8 proteins contain changes in amino acid residues that are not essential for activity. Such CARD-7 or CARD-8 proteins differ in amino acid sequence from SEQ ID NO:2 or SEQ ID NO:4, and yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of SEQ ID NO:2 or SEQ ID NO:4.

An isolated nucleic acid molecule encoding a CARD-7 or CARD-8 protein having a sequence which differs from that of SEQ ID NO:2 or SEQ ID NO:4, can be created by introducing one or more nucleotide substitutions, additions or deletions into the nucleotide sequence of CARD-7 (SEQ ID NO:1, SEQ ID NO:5) or CARD-8 (SEQ ID NO:3, SEQ ID NO:6) such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. Thus, for example, 1%, 2%, 3%, 5%, or 10% of the amino acids can be replaced by conservative substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in CARD-7 or CARD-8 is preferably replaced with another amino acid residue from the same side chain family. Alternatively, mutations can be introduced randomly along all or part of a CARD-7 or CARD-8 coding sequence, such as by saturation mutagenesis, and the resultant mutants can be screened for CARD-7 or CARD-8 biological activity to identify mutants that retain activity. Following mutagenesis, the encoded protein can be expressed recombinantly and the activity of the protein can be determined.

A mutant CARD-7 or CARD-8 protein can be assayed for: (1) the ability to form protein:protein interactions with proteins in the apoptotic signalling pathway; (2) the ability to bind a CARD-7 or CARD-8 ligand (e.g., CARD-5); or (3) the ability to bind to an intracellular target protein. In yet another embodiment, a mutant CARD-7 or CARD-8 protein can be assayed for the ability to modulate cellular proliferation, cellular differentiation, or cellular death.

The present invention encompasses the use of antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CARD-7 or CARD-8 coding strand, or to only a portion thereof, e.g., all or part of the protein coding region (or open reading frame). An antisense nucleic acid molecule can be antisense to a noncoding region of the coding strand of a nucleotide sequence encoding CARD-7 or CARD-8. The noncoding regions ("5' and 3' untranslated regions") are the 5' and 3' sequences which flank the coding region and are not translated into amino acids. Given the coding strand sequences encoding CARD-7 and CARD-8 disclosed herein, antisense nucleic acids can be designed according to the rules of Watson and Crick base pairing. The antisense nucleic acid molecule can be complementary to the entire coding region of CARD-7 or CARD-8 mRNA, but more preferably is an oligonucleotide which is antisense to only a portion of the coding or noncoding region of CARD-7 or CARD-8 mRNA. For example, the antisense oligonucleotide can be complementary to the region surrounding the translation start site of CARD-7 or CARD-8. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-aino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described furthr in the following subsection).

The antisense nucleic acid molecules are typically administered to a subject or generated in situ such that they hybridize with or bind to cellular mRNA and/or genomic DNA encoding a CARD-7 or CARD-8 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration for antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625–6641). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave CARD-7 or CARD-8 mRNA transcripts to thereby inhibit translation of CARD-7 or CARD-8 mRNA. A ribozyme having specificity for a CARD-7 or CARD-8-encoding nucleic acid can be designed based upon the nucleotide sequence of a CARD-7 or CARD-8 cDNA disclosed herein. For example, a derivative of a Tetrahymena L-19 IVS RNA can be constructed in which the nucleotide sequence of the active site is complementary to the nucleotide sequence to be cleaved in a CARD-7 or CARD-8-encoding mRNA. See, e.g., Cech et al. U.S. Pat. No. 4,987,071; and Cech et al. U.S. Pat. No. 5,116,742. Alternatively, CARD-7 or CARD-8 mRNA can be used to select a catalytic RNA having a specific ribonuclease activity from a pool of RNA molecules. See, e.g., Bartel and Szostak (1993) Science 261:1411–1418.

The invention also encompasses nucleic acid molecules which form triple helical structures. For example, CARD-7 or CARD-8 gene expression can be inhibited by targeting nucleotide sequences complementary to the regulatory region of the CARD-7 or CARD-8 (e.g., the CARD-7 or CARD-8 promoter and/or enhancers) to form triple helical structures that prevent transcription of the CARD-7 or CARD-8 gene in target cells. See generally, Helene (1991) Anticancer Drug Des. 6(6):569–84; Helene (1992) Ann. N.Y. Acad. Sci. 660:27–36; and Maher (1992) Bioassays 14(12):807–15.

Useful nucleic acid molecules can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) Bioorganic & Medicinal Chemistry 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) Proc. Natl. Acad. Sci. USA 93:14670–675.

PNAs of CARD-7 or CARD-8 can be used for therapeutic and diagnostic applications. For example, PNAs can be used as antisense or antigene agents for sequence-specific modulation of gene expression by, e.g., inducing transcription or translation arrest or inhibiting replication. PNAs of CARD-7 or CARD-8 can also be used, e.g., in the analysis of single base pair mutations in a gene by, e.g., PNA directed PCR clamping; as artificial restriction enzymes when used in combination with other enzymes, e.g., S1 nucleases (Hyrup (1996) supra; or as probes or primers for DNA sequence and hybridization (Hyrup (1996) supra; Perry-O'Keefe et al. (1996) Proc. Natl. Acad. Sci. USA 93: 14670–675).

PNAs of CARD-7 or CARD-8 can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of CARD-7 or CARD-8 can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) supra). The synthesis of PNA-DNA chimeras can be performed as described in Hyrup (1996) supra and Finn et al. (1996) Nucleic Acids Research 24(17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag et al. (1989) Nucleic Acid Res. 17:5973–88). PNA monomers are then coupled in a stepwise manner to produce a chimeric molecule with a 5' PNA segment and a 3' DNA segment (Finn et al. (1996) Nucleic Acids Research 24(17):3357–63). Alternatively, chimeric molecules can be synthesized with a 5' DNA segment and a 3' PNA segment (Peterser et al. (1975) Bioorganic Med. Chem. Lett. 5:1119–11124).

The oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) Bio/Techniques 6:958–976) or intercalating agents (see, e.g., Zon (1988) Pharm. Res. 5:539–549). To this end, the oligonucleotide may be conjugated to another molecule, e.g., a peptide, hybridization triggered cross-linking agent, transport agent, hybridization-triggered cleavage agent, etc.

II. Isolated CARD-7 and CARD-8 Proteins and Anti-CARD-7 and CARD-8 Antibodies.

One aspect of the invention pertains to the use of isolated CARD-7 and CARD-8 proteins, and biologically active portions thereof, as well as polypeptide fragments suitable for use as immunogens to raise anti-CARD-7 or CARD-8 antibodies. Native CARD-7 or CARD-8 proteins can be isolated from cells or tissue sources by an appropriate purification scheme using standard protein purification techniques. CARD-7 or CARD-8 proteins can be produced by recombinant DNA techniques. Alternative to recombinant expression, a CARD-7 or CARD-8 protein or polypeptide can be synthesized chemically using standard peptide synthesis techniques.

An "isolated" or "purified" protein or biologically active portion thereof is substantially free of cellular material or other contaminating proteins from the cell or tissue source from which the CARD-7 or CARD-8 protein is derived, or substantially free from chemical precursors or other chemicals when chemically synthesized. The language "substantially free of cellular material" includes preparations of CARD-7 or CARD-8 protein in which the protein is separated from cellular components of the cells from which it is isolated or recombinantly produced. Thus, CARD-7 or CARD-8 protein that is substantially free of cellular material includes preparations of CARD-7 or CARD-8 protein having less than about 30%, 20%, 10%, or 5% (by dry weight) of non-CARD-7 or CARD-8 protein (also referred to herein as a "contaminating protein"). When the CARD-7 or CARD-8 protein or biologically active portion thereof is recombinantly produced, it is also preferably substantially free of culture medium, i.e., culture medium represents less than about 20%, 10%, or 5% of the volume of the protein preparation. When CARD-7 or CARD-8 protein is produced by chemical synthesis, it is preferably substantially free of chemical precursors or other chemicals, i.e., it is separated from chemical precursors or other chemicals which are involved in the synthesis of the protein. Accordingly such preparations of CARD-7 or CARD-8 protein have less than about 30%, 20%, 10%, 5% (by dry weight) of chemical precursors or non-CARD-7 or CARD-8 chemicals.

Biologically active portions of a CARD-7 or CARD-8 protein include peptides comprising amino acid sequences sufficiently identical to or derived from the amino acid sequence of the CARD-7 or CARD-8 protein (e.g., the amino acid sequence shown in SEQ ID NO:2 or SEQ ID NO:4), which include less amino acids than the full length CARD-7 or CARD-8 protein, and exhibit at least one activity of a CARD-7 or CARD-8 protein. Typically, biologically active portions comprise a domain or motif with at least one activity of the CARD-7 or CARD-8 protein. A biologically active portion of a CARD-7 or CARD-8 protein can be a polypeptide which is, for example, 10, 25, 50, 100 or more amino acids in length. Preferred biologically active polypeptides include one or more identified CARD-7 or CARD-8 structural domains, e.g., the CARD domain.

Moreover, other biologically active portions, in which other regions of the protein are deleted, can be prepared by recombinant techniques and evaluated for one or more of the functional activities of a native CARD-7 or CARD-8 protein.

Useful CARD-7 or CARD-8 protein has the amino acid sequence shown of SEQ ID NO:2 or SEQ ID NO:4. Other useful CARD-7 or CARD-8 proteins are substantially identical to SEQ ID NO:2 or SEQ ID NO:4, and retain the functional activity of the protein of SEQ ID NO:2 or SEQ ID NO:4, yet differ in amino acid sequence due to natural allelic variation or mutagenesis.

A useful CARD-7 or CARD-8 protein is a protein which includes an amino acid sequence at least about 45%, preferably 55%, 65%, 75%, 85%, 95%, or 99% identical to the amino acid sequence of SEQ ID NO:2 or SEQ ID NO:4 and retains the functional activity of the CARD-7 or CARD-8 proteins of SEQ ID NO:2 or SEQ ID NO:4.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position. in the first sequence is occupied by the same amino acid residue or nucleotide as the corresponding position in the second sequence, then the molecules are identical at that position. The percent identity between the two sequences is a function of the number of identical positions shared by the sequences (i.e., % identity =# of identical positions/total # of positions ×100).

The determination of percent homology between two sequences can be accomplished using a mathematical algorithm. A preferred, non-limiting example of a mathematical algorithm utilized for the comparison of two sequences is the algorithm of Karlin and Altschul (1990) Proc. Nat'l Acad. Sci. USA 87:2264–2268, modified as in Karlin and Altschul (1993) Proc. Nat'l Acad. Sci. USA 90:5873–5877. Such an algorithm is incorporated into the NBLAST and XBLAST programs of Altschul, et al. (1990) J. Mol. Biol. 215:403–410. BLAST nucleotide searches can be performed with the NBLAST program, score=100, wordlength=12 to obtain nucleotide sequences similar or homologous to CARD-7 or CARD-8 nucleic acid molecules. BLAST protein searches can be performed with the XBLAST program, score=50, wordlength=3 to obtain amino acid sequences homologous to CARD-7 or CARD-8 protein molecules. To obtain gapped alignments for comparison purposes, Gapped BLAST can be utilized as described in Altschul et al. (1997) Nucleic Acids Res. 25:3389–3402. When utilizing BLAST and Gapped BLAST programs, the default parameters of the respective programs (e.g., XBLAST and NBLAST) can be used. See www.ncbi.nlm.nih.gov. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. When utilizing the ALIGN program for comparing nucleic acid sequences, a gap length penalty of 12 and a gap penalty of 4 can be used.

The percent identity between two sequences can be determined using techniques similar to those described above, with or without allowing gaps. In calculating percent identity, typically exact matches are counted.

CARD-7 or CARD-8 chimeric or fusion proteins are also useful. As used herein, a CARD-7 or CARD-8 "chimeric protein" or "fusion protein" comprises a CARD-7 or CARD-8 polypeptide operatively linked to a non-CARD-7 or CARD-8 polypeptide. A "CARD-7 or CARD-8 polypeptide" refers to a polypeptide having an amino acid sequence corresponding to all or a portion (preferably a biologically active portion) of a CARD-7 or CARD-8, whereas a "non-CARD-7 or CARD-8 polypeptide" refers to a polypeptide having an amino acid sequence corresponding to a protein which is not substantially identical to the CARD-7 or CARD-8 protein, e.g., a protein which is different from the CARD-7 or CARD-8 proteins and which is derived from the same or a different organism. Within the fusion protein, the term "operatively linked" is intended to indicate that the CARD-7 or CARD-8 polypeptide and the non-CARD-7 or CARD-8 polypeptide are fused in-frame to each other. The heterologous polypeptide can be fused to the N-terminus or C-terminus of the CARD-7 or CARD-8 polypeptide.

One useful fusion protein is a GST fusion protein in which the CARD-7 or CARD-8 sequences are fused to the C-terminus of the GST sequences. Such fusion proteins can facilitate the purification of recombinant CARD-7 or CARD-8. In another embodiment, the fusion protein contains a signal sequence from another protein. In certain host cells (e.g., mammalian host cells), expression and/or secretion of CARD-7 or CARD-8 can be increased through use of a heterologous signal sequence. For example, the gp67 secretory sequence of the baculovirus envelope protein can be used as a heterologous signal sequence (Current Protocols in Molecular Biology, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Molecular cloning, Sambrook et al, second edition, Cold spring harbor laboratory press, 1989) and the protein A secretory signal (Pharmacia Biotech; Piscataway, N.J.).

A useful fusion protein can be a CARD-7 or CARD-8-immunoglobulin fusion protein in which all or part of CARD-7 or CARD-8 is fused to sequences derived from a member of the immunoglobulin protein family. The CARD-7 or CARD-8-immunoglobulin fusion proteins can be incorporated into pharmaceutical compositions and administered to a subject to inhibit an interaction between a CARD-7 or CARD-8 ligand and a CARD-7 or CARD-8 protein on the surface of a cell, to thereby suppress CARD-7 or CARD-8-mediated signal transduction in vivo. The CARD-7 or CARD-8-immunoglobulin fusion proteins can be used to affect the bioavailability of a CARD-7 or CARD-8 cognate ligand. Inhibition of the CARD-7 ligand/CARD-7, CARD-8 ligand/CARD-8 interaction may be useful therapeutically for both the treatment of proliferative and differentiative disorders, as well as modulating (e.g., promoting or inhibiting) cell survival. Moreover, the CARD-7 or CARD-8-immunoglobulin fusion proteins can be used as immunogens to produce anti-CARD-7 or CARD-8 antibodies in a subject, to purify CARD-7 or CARD-8 ligands and in screening assays to identify molecules which inhibit the interaction of CARD-7 or CARD-8 with a CARD-7 or CARD-8 ligand.

Preferably, a CARD-7 or CARD-8 chimeric or fusion protein is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al. eds., John Wiley & Sons: 1992). Moreover, many expression vectors are commercially available that already encode a fusion moiety (e.g., a GST polypeptide). A CARD-7 or CARD-8-encoding nucleic acid can be cloned into such an expression vector such that the fusion moiety is linked in-frame to the CARD-7 or CARD-8 protein.

The present invention also pertains to variants of the CARD-7 or CARD-8 proteins which function as either CARD-7 or CARD-8 agonists (mimetics) or as CARD-7 or CARD-8 antagonists. Variants of the CARD-7 or CARD-8 protein can be generated by mutagenesis, e.g., discrete point mutation or truncation of the CARD-7 or CARD-8 protein. An agonist of the CARD-7 or CARD-8 protein can retain substantially the same, or a subset, of the biological activities of the naturally occurring form of the CARD-7 or CARD-8 protein. An antagonist of the CARD-7 or CARD-8 protein can inhibit one or more of the activities of the naturally-occurring form of the CARD-7 or CARD-8 protein by, for example, competitively binding to a downstream or upstream member of a cellular signaling cascade which includes the CARD-7 or CARD-8 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the CARD-7 or CARD-8 proteins.

Variants of the CARD-7 or CARD-8 protein which function as either CARD-7 or CARD-8 agonists (mimetics) or as CARD-7 or CARD-8 antagonists can be identified by screening combinatorial libraries of mutants, e.g., truncation mutants of the CARD-7 or CARD-8 protein for CARD-7 or CARD-8 protein agonist or antagonist activity. In one embodiment, a variegated library of CARD-7 or CARD-8 variants is generated by combinatorial mutagenesis at the nucleic acid level and is encoded by a variegated gene library. A variegated library of CARD-7 or CARD-8 variants can be produced by, for example, ligating a mixture of synthetic oligonucleotides into gene sequences such that a degenerate set of potential CARD-7 or CARD-8 sequences is expressible as individual polypeptides, or alternatively, as a set of larger fusion proteins (e.g., for phage display) containing the set of CARD-7 or CARD-8 sequences therein. There are a variety of methods which can be used to produce libraries of potential CARD-7 or CARD-8 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential CARD-7 or CARD-8 sequences. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

Useful fragments of CARD-7 and CARD-8 include fragments comprising or consisting of a domain or subdomain described herein, e.g., a CARD domain.

In addition, libraries of fragments of the CARD-7 or CARD-8 protein coding sequence can be used to generate a variegated population of CARD-7 or CARD-8 fragments for screening and subsequent selection of variants of a CARD-7 or CARD-8 protein. In one embodiment, a library of coding sequence fragments can be generated by treating a double stranded PCR fragment of a CARD-7 or CARD-8 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the CARD-7 or CARD-8 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CARD-7 or CARD-8 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify CARD-7 or CARD-8 variants (Arkin and Yourvan (1992) Proc. Natl. Acad. Sci. USA 89:7811–7815; Delgrave et al. (1993) Protein Engineering 6(3):327–33 1).

An isolated CARD-7 or CARD-8 protein, or a portion or fragment thereof, can be used as an immunogen to generate antibodies that bind CARD-7 or CARD-8 using standard techniques for polyclonal and monoclonal antibody preparation. The full-length CARD-7 or CARD-8 protein can be used or, alternatively, the invention provides antigenic peptide fragments of CARD-7 or CARD-8 for use as immunogens. The antigenic peptide of CARD-7 or CARD-8 comprises at least 8 (preferably 10, 15, 20, or 30) amino acid residues of the amino acid sequence shown in SEQ ID NO:2 or SEQ ID NO:8 and encompasses an epitope of CARD-7 or CARD-8 such that an antibody raised against the peptide forms a specific immune complex with CARD-7 or CARD-8.

Useful antibodies include antibodies which bind to a domain or subdomain of CARD-7 or CARD-8 described herein (e.g., a kinase domain, a CARD domain, or a leucine-rich domain).

Figure 3:
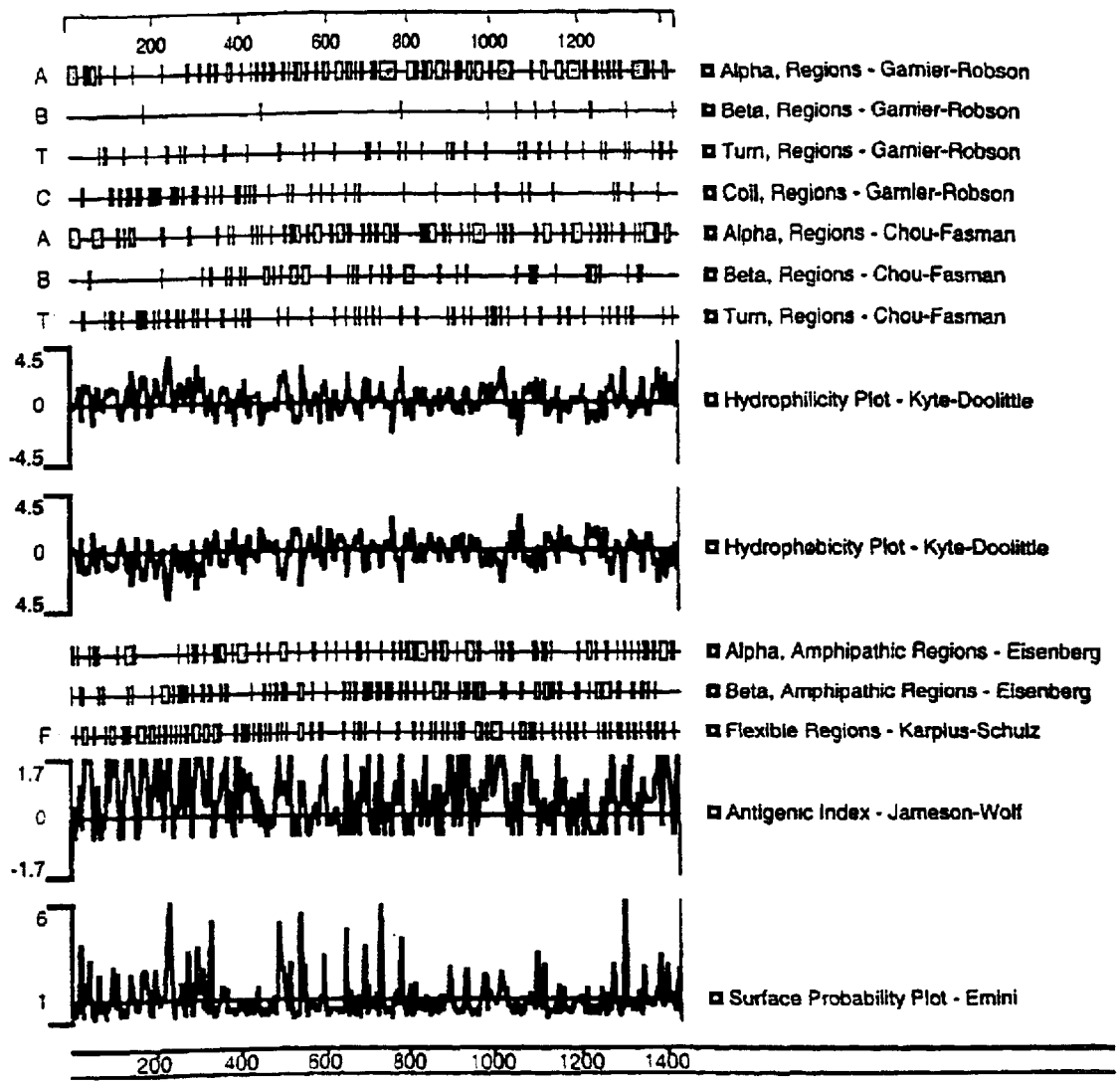
FIG. 3 depicts a plot showing the predicted structural features of human CARD-7. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).
Figure 5:
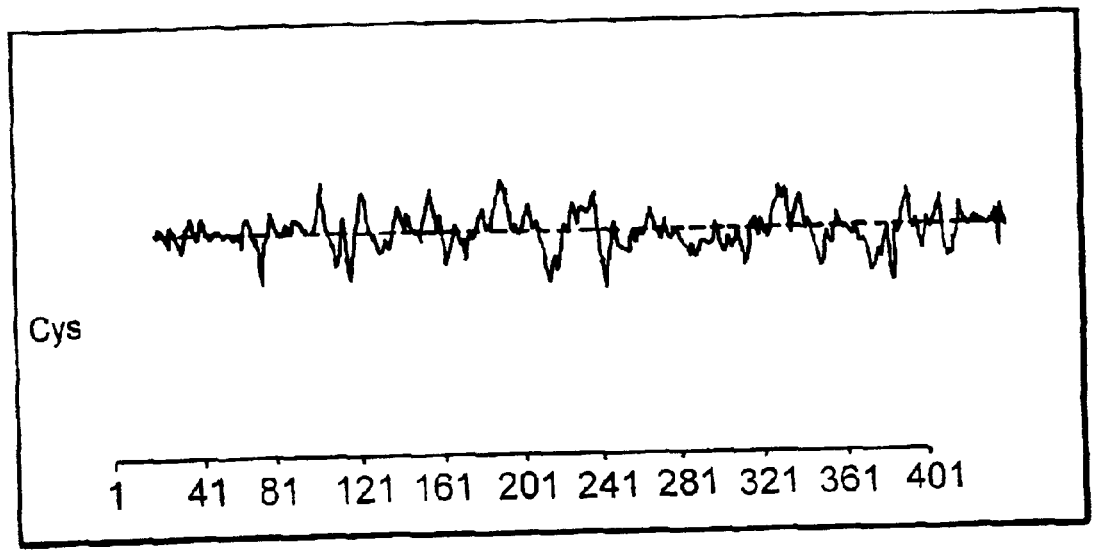
FIG. 5 depicts a hydropathy plot of human CARD-8. Relatively hydrophobic residues are above the dashed horizontal line, and relatively hydrophilic residues are below the dashed horizontal line. The cysteine residues (cys) and potential N-glycosylation sites (Ngly) are indicated by short vertical lines just below the hydropathy trace.
Figure 6:
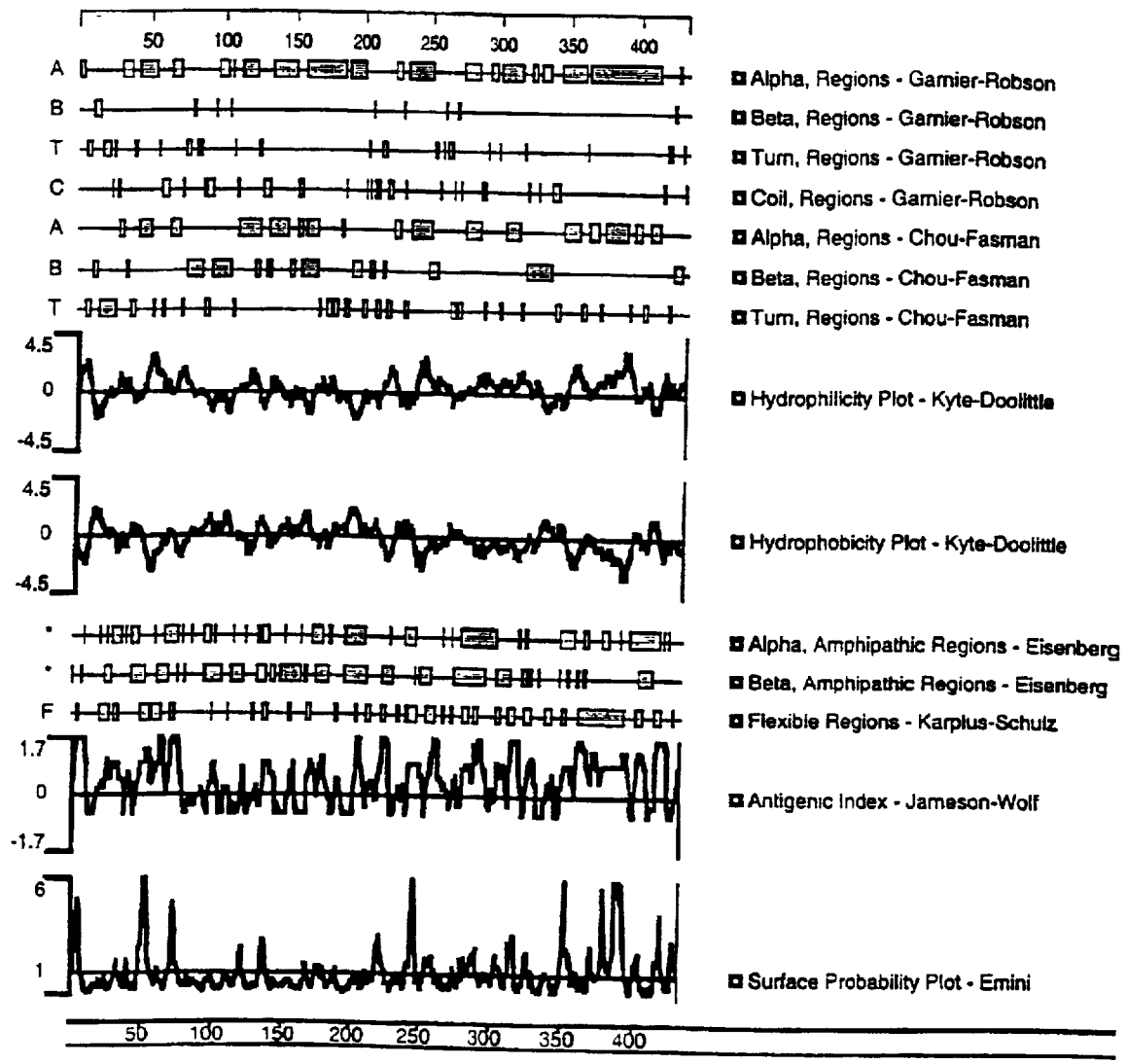
FIG. 6 depicts a plot showing the predicted structural features of human CARD-8. This figure shows the predicted alpha regions (Garnier-Robinson and Chou-Fasman), the predicted beta regions (Garnier-Robinson and Chou-Fasman), the predicted turn regions (Garnier-Robinson and Chou-Fasman) and the predicted coil regions (Garnier-Robinson and Chou-Fasman). Also included in the figure is a hydrophilicity plot (Kyte-Doolittle), the predicted alpha and beta-amphatic regions (Eisenberg), the predicted flexible regions (Karplus-Schulz), the predicted antigenic index (Jameson-Wolf) and the predicted surface probability plot (Emini).

Preferred epitopes encompassed by the antigenic peptide are regions of CARD-7 or CARD-8 that are located on the surface of the protein, e.g., hydrophilic regions. Other important criteria include a preference for a terminal sequence, high antigenic index (e.g., as predicted by Jameson-Wolf algorithm), ease of peptide synthesis (e.g., avoidance of prolines); and high surface probability (e.g., as predicted by the Emini algorithm; FIG. 3 and FIG. 6).

A CARD-7 or CARD-8 immunogen typically is used to prepare antibodies by immunizing a suitable subject, (e.g., rabbit, goat, mouse or other mammal) with the immunogen. An appropriate immunogenic preparation can contain, for example, recombinantly expressed CARD-7 or CARD-8 protein or a chemically synthesized CARD-7 or CARD-8 polypeptide. The preparation can further include an adjuvant, such as Freund's complete or incomplete adjuvant, or similar immunostimulatory agent. Immunization of a suitable subject with an immunogenic CARD-7 or CARD-8 preparation induces a polyclonal anti-CARD-7 or CARD-8 antibody response.

Accordingly, another aspect of the invention pertains to anti-CARD-7 or CARD-8 antibodies. The term "antibody" as used herein refers to immunoglobulin molecules and immunologically active portions of immunoglobulin molecules, i.e., molecules that contain an antigen binding site which specifically binds an antigen, such as CARD-7 or CARD-8. A molecule which specifically binds to CARD-7 or CARD-8 is a molecule which binds CARD-7 or CARD-8, but does not substantially bind other molecules in a sample, e.g., a biological sample, which naturally contains CARD-7 or CARD-8. Examples of immunologically active portions of immunoglobulin molecules include F(ab) and F(ab')2 fragments which can be generated by treating the antibody with an enzyme such as pepsin. The invention provides polyclonal and monoclonal antibodies that bind CARD-7 or CARD-8. The term "monoclonal antibody" or "monoclonal antibody composition", as used herein, refers to a population of antibody molecules that contain only one species of an antigen binding site capable of immunoreacting with a particular epitope of CARD-7 or CARD-8. A monoclonal antibody composition thus typically displays a single binding affinity for a particular CARD-7 or CARD-8 protein with which it immunoreacts.

Polyclonal anti-CARD-7 or CARD-8 antibodies can be prepared as described above by immunizing a suitable subject with a CARD-7 or CARD-8 immunogen. The anti-CARD-7 or CARD-8 antibody titer in the immunized subject can be monitored over time by standard techniques, such as with an enzyme linked immunosorbent assay (ELISA) using immobilized CARD-7 or CARD-8. If desired, the antibody molecules directed against CARD-7 or CARD-8 can be isolated from the mammal (e.g., from the blood) and further purified by well-known techniques, such as protein A chromatography to obtain the IgG fraction. At an appropriate time after immunization, e.g., when the anti-CARD-7 or CARD-8 antibody titers are highest, antibody-producing cells can be obtained from the subject and used to prepare monoclonal antibodies by standard techniques, such as the hybridoma technique originally described by Kohler and Milstein (1975) Nature 256:495–497, the human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing various antibodies monoclonal antibody hybridomas is well known (see generally Current Protocols in Immunology (1994) Coligan et al. (eds.) John Wiley & Sons, Inc., New York, N.Y.). Briefly, an immortal cell line (typically a myeloma) is fused to lymphocytes (typically splenocytes) from a mammal immunized with a CARD-7 or CARD-8 immunogen as described above, and the culture supernatants of the resulting hybridoma cells are screened to identify a hybridoma producing a monoclonal antibody that binds CARD-7 or CARD-8.

Any of the many well known protocols used for fusing lymphocytes and immortalized cell lines can be applied for the purpose of generating an anti-CARD-7 or CARD-8 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CARD-7 or CARD-8, e.g., using a standard ELISA assay.

Alternative to preparing monoclonal antibody-secreting hybridomas, a monoclonal anti-CARD-7 or CARD-8 antibody can be identified and isolated by screening a recombinant combinatorial immunoglobulin library (e.g., an antibody phage display library) with CARD-7 or CARD-8 to thereby isolate immunoglobulin library members that bind CARD-7 or CARD-8. Kits for generating and screening phage display libraries are commercially available (e.g., the Pharmacia Recombinant Phage Antibody System, Catalog No. 27-9400–01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J. 12:725–734.

Additionally, recombinant anti-CARD-7 or CARD-8 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125, 023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, (1985) Science 229:1202–1207; Oi et al. (1986) Bio/Techniques 4:214; U.S. Pat. No. 5,225, 539; Jones et al. (1986) Nature 321:552–525; Verhoeyan et al. (1988) Science 239:1534; and Beidler et al. (1988) J. Immunol. 141:4053–4060.

An anti-CARD-7 or CARD-8 antibody (e.g., monoclonal antibody) can be used to isolate CARD-7 or CARD-8 by standard techniques, such as affinity chromatography or immunoprecipitation. An anti-CARD-7 or CARD-8 antibody can facilitate the purification of natural CARD-7 or CARD-8 from cells and of recombinantly produced CARD-7 or CARD-8 expressed in host cells. Moreover, an anti-CARD-7 or CARD-8 antibody can be used to detect CARD-7 or CARD-8 protein (e.g., in a cellular lysate or cell supernatant) in order to evaluate the abundance and pattern of expression of the CARD-7 or CARD-8 protein. Anti-CARD-7 or CARD-8 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to the use of vectors, preferably expression vectors, containing a nucleic acid encoding CARD-7 or CARD-8 (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operatively linked. In general, expression vectors of utility in recombinant DNA techniques are often in the form of plasmids (vectors). However, other forms of expression vectors (e.g., replication defective retroviruses, adenoviruses and adeno-associated viruses) which serve equivalent functions are also useful.

Recombinant expression vectors comprise a nucleic acid molecule in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors can be introduced into host cells to thereby produce proteins or peptides, including fusion proteins or peptides, encoded by nucleic acids as described herein (e.g., CARD-7 or CARD-8 proteins, mutant forms of CARD-7 or CARD-8, fusion proteins, etc.).

Recombinant expression vectors can be designed for expression of CARD-7 or CARD-8 in prokaryotic or eukaryotic cells, e.g., bacterial cells such as E. coli, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31–40), pMAL (New England Biolabs, Beverly, Mass. ) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301–315) and pET 11d (Studier et al., Gene Expression Technology: Methods in Enzymology 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident ë prophage harboring a T7 gn1 gene under the transcriptional control of the lacUV5 promoter.

One strategy to maximize recombinant protein expression in E. coli is to express the protein in a host bacteria with an impaired capacity to proteolytically cleave the recombinant protein (Gottesman, Gene Expression Technology: Methods in Enzymology 185, Academic Press, San Diego, Calif. (1990) 119–128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111–2118). Such alteration of nucleic acid sequences can be carried out by standard DNA synthesis techniques.

In another embodiment, the CARD-7 or CARD-8 expression vector is a yeast expression vector. Examples of vectors for expression in yeast S. cerivisae include pYepSec1 (Baldari et al. (1987) EMBO J. 6:229–234), pMFa (Kurjan and Herskowitz, (1982) Cell 30:933–943), pJRY88 (Schultz et al. (1987) Gene 54:113–123), pYES2 (Invitrogen Corporation, San Diego, Calif.), pGBT9 (Clontech, Palo Alto, Calif.), pGAD10 (Clontech, Palo Alto, Calif.), pYADE4 and pYGAE2 and pYPGE2 (Brunelli and Pall, (1993) Yeast 9:1299–1308), pYPGE15 (Brunelli and Pall, (1993) Yeast 9:1309–1318), pACTII (Dr. S. E. Elledge, Baylor College of Medicine), and picZ (InVitrogen Corp, San Diego, Calif.).

Alternatively, CARD-7 or CARD-8 can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156–2165) and the pVL series (Lucklow and Summers (1989) Virology 170:31–39).

Examples of useful mammalian expression vectors include pCDM8 (Seed (1987) Nature 329:840), pCI (Promega), and pMT2PC (Kaufman et al. (1987) EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al. (supra).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268–277), lymphoid-specific promoters (Calame and Eaton (1988) Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) Science 249:374–379) and the α-fetoprotein promoter (Campes and Tilghman (1989) Genes Dev. 3:537–546).

A useful recombinant expression vector can comprise a DNA molecule cloned into the expression vector in an antisense orientation. That is, the DNA molecule is operatively linked to a regulatory sequence in a manner which allows for expression (by transcription of the DNA molecule) of an RNA molecule which is antisense to CARD-7 or CARD-8 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to the use of host cells into which a recombinant expression vector or isolated nucleic acid molecule has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, CARD-7 or CARD-8 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA or an isolated nucleic acid molecule can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In some cases vector DNA is retained by the host cell. In other cases the host cell does not retain vector DNA and retains only an isolated nucleic acid molecule carried by the vector. In some cases, and isolated nucleic acid molecule is used to transform a cell without the use of a vector.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding CARD-7 or CARD-8 or can be introduced on a separate vector. Cells stably transfected with the introduced nucleic acid can be identified by drug selection (e.g., cells that have incorporated the selectable marker gene will survive, while the other cells die).

A host cell, such as a prokaryotic or eukaryotic host cell in culture, can be used to produce (i.e., express) a CARD-7 or CARD-8 protein. Accordingly, the invention further provides methods for producing CARD-7 or CARD-8 protein using the host cells of the invention. In one embodiment, the method comprises culturing the host cell of the invention (into which a recombinant expression vector or isolated nucleic acid molecule encoding CARD-7 or CARD-8 has been introduced) in a suitable medium such that CARD-7 or CARD-8 protein is produced. In another embodiment, the method further comprises isolating CARD-7 or CARD-8 from the medium or the host cell.

The expression characteristics of an endogenous CARD-7 or CARD-8 gene within a cell may be modified by inserting a heterologous DNA regulatory element into the genome of the cell such that the inserted regulatory element is operably linked to the endogenous CARD-7 or CARD-8 gene. For example, an endogenous CARD-7 or CARD-8 gene which is normally transcriptionally silent o rexpressed at only a very low level may be activated by inserting a regulatory element which is capable of promoting the expression of a normally expressed gene product in that cell type. Alternatively, an endogenous CARD-7 or CARD-8 gene can be activated by insertion of a promiscuous regulatory element which works in many cell types. Insertion of regulatory elements can be accomplished by procedures known to those of skill in the art (U.S. Pat. No. 5,272,071; PCT Publication No. WO 91/06667, published May 16, 1991).

The host cells can also be used to produce nonhuman transgenic animals. For example, in one embodiment, a host cell of the invention is a fertilized oocyte or an embryonic stem cell into which CARD-7 or CARD-8-coding sequences have been introduced. Such host cells can then be used to create non-human transgenic animals in which exogenous CARD-7 or CARD-8 sequences have been introduced into their genome or homologous recombinant animals in which endogenous CARD-7 or CARD-8 sequences have been altered. Such animals are useful for studying the finction and/or activity of CARD-7 or CARD-8 and for identifying and/or evaluating modulators of CARD-7 or CARD-8 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous CARD-7 or CARD-8 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing CARD-7 or CARD-8-encoding nucleic acid into the male pronuclei of a fertilized oocyte, e.g., by microinjection, retroviral infection, and allowing the oocyte to develop in a pseudopregnant female foster animal. The CARD-7 or CARD-8 cDNA sequence, e.g., that of SEQ ID NO:1, SEQ ID NO:3, SEQ ID NO:5, or SEQ ID NO:6, can be introduced as a transgene into the genome of a non-human animal. Alternatively, a nonhuman homolog or ortholog of the human CARD-7 or CARD-8 gene, such as a mouse CARD-7 or CARD-8 gene, can be isolated based on hybridization to the human CARD-7 or CARD-8 cDNA and used as a transgene. Intronic sequences and polyadenylation signals can also be included in the transgene to increase the efficiency of expression of the transgene. A tissue-specific regulatory sequence(s) can be operably linked to the CARD-7 or CARD-8 transgene to direct expression of CARD-7 or CARD-8 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of the CARD-7 or CARD-8 transgene in its genome and/or expression of CARD-7 or CARD-8 mRNA in tissues or cells of the animals. A transgenic founder animal can then be used to breed additional animals carrying the transgene. Moreover, transgenic animals carrying a transgene encoding CARD-7 or CARD-8 can further be bred to other transgenic animals carrying other transgenes.

To create an homologous recombinant animal, a vector is prepared which contains at least a portion of a CARD-7 or CARD-8 gene (e.g., a human or a non-human homolog of the CARD-7 or CARD-8 gene, e.g., a murine CARD-7 or CARD-8 gene) into which a deletion, addition or substitution has been introduced to thereby alter, e.g., functionally disrupt, the CARD-7 or CARD-8 gene. In an embodiment, the vector is designed such that, upon homologous recombination, the endogenous CARD-7 or CARD-8 gene is functionally disrupted (i.e., no longer encodes a functional protein; also referred to as a "knock out" vector). Alternatively, the vector can be designed such that, upon homologous recombination, the endogenous CARD-7 or CARD-8 gene is mutated or otherwise altered but still encodes functional protein (e.g., the upstream regulatory region can be altered to thereby alter the expression of the endogenous CARD-7 or CARD-8 protein). In the homologous recombination vector, the altered portion of the CARD-7 or CARD-8 gene is flanked at its 5' and 3' ends by additional nucleic acid of the CARD-7 or CARD-8 gene to allow for homologous recombination to occur between the exogenous CARD-7 or CARD-8 gene carried by the vector and an endogenous CARD-7 or CARD-8 gene in an embryonic stem cell. The additional flanking CARD-7 or CARD-8 nucleic acid is of sufficient length for successful homologous recombination with the endogenous gene. Typically, several kilobases of flanking DNA (both at the 5' and 3' ends) are included in the vector (see, e.g., Thomas and Capecchi (1987) Cell 51:503 for a description of homologous recombination vectors). The vector is introduced into an embryonic stem cell line (e.g., by electroporation) and cells in which the introduced CARD-7 or CARD-8 gene has homologously recombined with the endogenous CARD-7 or CARD-8 gene are selected (see, e.g., Li et al. (1992) Cell 69:915). The selected cells are then injected into a blastocyst of an animal (e.g., a mouse) to form aggregation chimeras (see, e.g., Bradley in Teratocarcinomas and Embryonic Stem Cells: A Practical Approach, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) Current Opinion in Bio/Technology 2:823–829 and in PCT Publication Nos. WO 90/11354, WO 91/01140, WO 92/0968, and WO 93/04169.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) Nature 385:810–813 and PCT Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The CARD-7 or CARD-8 nucleic acid molecules, CARD-7 or CARD-8 proteins, and anti-CARD-7 or CARD-8 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of the invention. Such methods comprise formulating a pharmaceutically acceptable carrier with an agent which modulates expression or activity of a CARD-7 or CARD-8 polypeptide or nucleic acid. Such compositions can further include additional active agents. Thus, the invention further includes methods for preparing a pharmaceutical composition by formulating a pharmaceutically acceptable carrier with an agent which modulates expression or activity of a CARD-7 or CARD-8 polypeptide or nucleic acid and one or more additional active compounds.

The agent which modulates expression or activity may, for example, be a small molecule. For example, such small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight les than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to modulated. Such appropriate doses may be determined using the assays described herein. When one or more of these small molecules is to be administered to an animal (e.g., a human) in order to modulate expression or activity of a CARD-7 or CARD-8 polypeptide or nucleic acid, a physician, veterinarian, or researcher may, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a CARD-7 or CARD-8 protein or anti-CARD-7 or CARD-8 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

A CARD-7 or CARD-8 nucleic acid molecule can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) Proc. Natl. Acad. Sci. USA 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). A CARD-7 or CARD-8 protein interacts with other cellular proteins and can thus be used for (i) regulation of cellular proliferation; (ii) regulation of cellular differentiation; and (iii) regulation of cell survival. The isolated nucleic acid molecules of the invention can be used to express CARD-7 or CARD-8 protein (e.g., via a recombinant expression vector in a host cell in gene therapy applications), to detect CARD-7 or CARD-8 mRNA (e.g., in a biological sample) or a genetic lesion in a CARD-7 or CARD-8 gene, and to modulate CARD-7 or CARD-8 activity. In addition, the CARD-7 or CARD-8 proteins can be used to screen drugs or compounds which modulate the CARD-7 or CARD-8 activity or expression as well as to treat disorders characterized by insufficient or excessive production of CARD-7 or CARD-8 protein or production of CARD-7 or CARD-8 protein forms which have decreased or aberrant activity compared to CARD-7 or CARD-8 wild type protein. In addition, the anti-CARD-7 or CARD-8 antibodies of the invention can be used to detect and isolate CARD-7 or CARD-8 proteins and modulate CARD-7 or CARD-8 activity.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to CARD-7 or CARD-8 proteins or biologically active portions thereof or have a stimulatory or inhibitory effect on, for example, CARD-7 or CARD-8 expression or CARD-7 or CARD-8 activity.

Among the screening assays provided by the invention are screening to identify molecules that prevent the dimerization of a CARD-containing polypeptide of the invention, screening to identify molecules which block the binding of a CARD containing polypeptide to a CARD-containing polypeptide of the invention (e.g., CARD-7), screening to identify a competitive inhibitor of the binding of a nucleotide to the nucleotide binding site of a CARD-containing polypeptide of the invention, screening to identify compounds which block the interaction between the leucine-rich repeat of a CARD-containing polypeptide of the invention and a ligand which binds to the leucine-rich repeat.

Among the screening assays provided by the invention are screening to identify molecules that increase or decrease the dimerization (or oligomerization) of CARD-7 or CARD-8, screening to identify molecules which block the binding of a CARD containing polypeptide to CARD-7 or CARD-8, and screening to identify a competitive inhibitor of the binding of a nucleotide to the nucleotide binding site of CARD-7. Screening assays, e.g., dimerization assays, can employ full-length CARD-7 or CARD-8 or a portion of CARD-7 or CARD-8, e.g, the CARD domain, the nucleotide binding site domain, or the leucine-rich repeat.

Screening assays can also be used to identify compounds which bind to the the nucleotide binding site domain of CARD-7 or to the leucine-rich repeat of CARD-7 (e.g., a molecule which blocks binding of a second protein the leucine-rich repeat of CARD-7).

The assays described below can be used to identify compounds that modulate the interaction between CARD-7 and CARD-5. Such assays can employ full-length CARD-5 and CARD-7 or fragments thereof (e.g., a fragment which includes a CARD domain).

In one embodiment, the invention provides assays for screening candidate or test compounds which bind to or modulate the activity of a CARD-7 or CARD-8 proteins or polypeptides or biologically active portions thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145). Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994)J.Med.Chem. 37:1233.

Libraries of compounds may be presented in solution (e.g., Houghten (1992) Bio/Techniques 13:412–421), or on beads (Lam (1991) Nature 354:82–84), chips (Fodor (1993) Nature 364:555–556), bacteria (U.S. Pat. No. 5,223,409), spores (U.S. Pat. Nos. 5,571,698; 5,403,484; and 5,223, 409), plasmids (Cull et al. (1992) Proc. Natl. Acad. Sci. USA 89:1865–1869) or on phage (Scott and Smith (1990) Science 249:386–390; Devlin (1990) Science 249:404–406; Cwirla et al. (1990) Proc. Natl. Acad. Sci. 87:6378–6382; and Felici (1991) J. Mol. Biol. 222:301–310).

Determining the ability of the test compound to modulate the activity of CARD-7 or CARD-8 or a biologically active portion thereof can be accomplished, for example, by determining the ability of the CARD-7 or CARD-8 protein to bind to or interact with a CARD-7 or CARD-8 target molecule. As used herein, a "target molecule" is a molecule with which a CARD-7 or CARD-8 protein binds or interacts in nature, for example, a molecule associated with the internal surface of a cell membrane or a cytoplasmic molecule. A CARD-7 or CARD-8 target molecule can be a non-CARD-7 or CARD-8 molecule or a CARD-7 or CARD-8 protein or polypeptide of the present invention. In one embodiment, a CARD-7 or CARD-8 target molecule is a component of an apoptotic signal transduction pathway. The target, for example, can be a second intracellular protein which has catalytic activity or a protein which facilitates the association of downstream signaling molecules with CARD-7 or CARD-8.

Determining the ability of the test compound to modulate the activity of CARD-7 or CARD-8 or a biologically active portion thereof can be accomplished, for example, by determining the ability of the CARD-7 or CARD-8 protein to bind to or interact with any of the specific proteins listed in the previous paragraph as CARD-7 or CARD-8 target molecules. In another embodiment, CARD-7 or CARD-8 target molecules include all proteins that bind to a CARD-7 or CARD-8 protein or a fragment thereof in a two-hybrid system binding assay which can be used without undue experimentation to isolate such proteins from cDNA or genomic two-hybrid system libraries.

Determining the ability of the CARD-7 or CARD-8 protein to bind to or interact with a CARD-7 or CARD-8 target molecule can be accomplished by one of the methods described above for determining direct binding. In an embodiment, determining the ability of the CARD-7 or CARD-8 protein to bind to or interact with a CARD-7 or CARD-8 target molecule can be accomplished by determining the activity of the target molecule. For example, the activity of the target molecule can be determined by detecting induction of a cellular second messenger of the target (e.g., intracellular Ca2+, diacylglycerol, IP3, etc.), detecting catalytic/enzymatic activity of the target on an appropriate substrate, detecting the induction of a reporter gene (e.g., a CARD-7 or CARD-8-responsive regulatory element operatively linked to a nucleic acid encoding a detectable marker, e.g., luciferase), or detecting a cellular response, for example, cell survival, cellular differentiation, or cell proliferation. In addition, and in another embodiment, genes induced by CARD-7 or CARD-8 expression can be identified by expressing CARD-7 or CARD-8 in a cell line and conducting a transcriptional profiling experiment wherein the mRNA expression patterns of the cell line transformed with an empty expression vector and the cell line transformed with a CARD-7 or CARD-8 expression vector are compared. The promoters of genes induced by CARD-7 or CARD-8 expression can be operatively linked to reporter genes suitable for screening such as luciferase, secreted alkaline phosphatase, or beta-galactosidase and the resulting constructs could be introduced into appropriate expression vectors. A recombinant cell line containing CARD-7 or CARD-8 and transfected with an expression vector containing a CARD-7 or CARD-8 responsive promoter operatively linked to a reporter gene can be used to identify test compounds that modulate CARD-7 or CARD-8 activity by assaying the expression of the reporter gene in response to contacting the recombinant cell line with test compounds. CARD-7 or CARD-8 agonists can be identified as increasing the expression of the reporter gene and CARD-7 or CARD-8 antagonists can be identified as decreasing the expression of the reporter gene.

In another embodiment of the invention, the ability of a test compound to modulate the activity of CARD-7, CARD-8, or biologically active portions thereof can be determined by assaying the ability of the test compound to modulate CARD-7 or CARD-8-dependent pathways or processes where the CARD-7 or CARD-8 target proteins that mediate the CARD-7 or CARD-8 effect are known or unknown. Potential CARD-7 or CARD-8-dependent pathways or processes include, but are not limited to, the modulation of cellular signal transduction pathways and their related second messenger molecules (e.g., intracellular $Ca^{2+}$, diacylglycerol, IP3, cAMP etc.), cellular enzymatic activities, cellular responses (e.g., cell survival, cellular differentiation, or cell proliferation), or the induction or repression of cellular or heterologous mRNAs or proteins. CARD-7 or CARD-8-dependent pathways or processes could be assayed by standard cell-based or cell free assays appropriate for the specific pathway or process under study. In yet another embodiment, an assay of the present invention is a cell-free assay comprising contacting a CARD-7 or CARD-8 protein or biologically active portion thereof with a test compound and determining the ability of the test compound to bind to the CARD-7 or CARD-8 protein or biologically active portion thereof. Binding of the test compound to the CARD-7 or CARD-8 protein can be determined either directly or indirectly as described above. In one embodiment, a competitive binding assay includes contacting the CARD-7 or CARD-8 protein or biologically active portion thereof with a compound known to bind CARD-7 or CARD-8 to form an assay mixture, contacting the assay mixture with a test compound, and determining the ability of the test compound to interact with a CARD-7 or CARD-8 protein, wherein determining the ability of the test compound to interact with a CARD-7 or CARD-8 protein comprises determining the ability of the test compound to preferentially bind to CARD-7 or CARD-8 or biologically active portion thereof as compared to the known binding compound.

In another embodiment, an assay is a cell-free assay comprising contacting CARD-7 or CARD-8 protein or biologically active portion thereof with a test compound and determining the ability of the test compound to modulate (e.g., stimulate or inhibit) the activity of the CARD-7 or CARD-8 protein or biologically active portion thereof. Determining the ability of the test compound to modulate the activity of CARD-7 or CARD-8 can be accomplished, for example, by determining the ability of the CARD-7 or CARD-8 protein to bind to a CARD-7 or CARD-8 target molecule by one of the methods described above for determining direct binding. In an alternative embodiment, determining the ability of the test compound to modulate the activity of CARD-7 or CARD-8 can be accomplished by determining the ability of the CARD-7 or CARD-8 protein to further modulate a CARD-7 or CARD-8 target molecule. For example, the catalytic/enzymatic activity of the target molecule on an appropriate substrate can be determined as previously described.

In yet another embodiment, the cell-free assay comprises contacting the CARD-7 or CARD-8 protein or biologically active portion thereof with a known compound which binds CARD-7 or CARD-8 to form an assay mixture, contacting the assay mixture with a test compound, and determining the ability of the test compound to interact with a CARD-7 or CARD-8 protein, wherein determining the ability of the test compound to interact with a CARD-7 or CARD-8 protein comprises determining the ability of the CARD-7 or CARD-8 protein to preferentially bind to or modulate the activity of a CARD-7 or CARD-8 target molecule. The cell-free assays of the present invention are amenable to use of both the soluble form or the membrane-associated form of CARD-7 or CARD-8. A membrane-associated form of CARD-7 or CARD-8 refers to CARD-7 or CARD-8 that interacts with a membrane-bound target molecule. In the case of cell-free assays comprising the membrane-associated form of CARD-7 or CARD-8, it may be desirable to utilize a solubilizing agent such that the membrane-associated form of CARD-7 or CARD-8 is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® -114, Thesit®, Isotridecypoly(ethylene glycol ether)n, 3-[(3-cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either CARD-7 or CARD-8 or its target molecule to facilitate separation of complexed from uncomplexed forms of one or both of the proteins, as well as to accommodate automation of the assay. Binding of a test compound to CARD-7 or CARD-8, or interaction of CARD-7 or CARD-8 with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/CARD-7 or CARD-8 fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or CARD-7 or CARD-8 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-7 or CARD-8 binding or activity determined using standard techniques. In an alternative embodiment, MYC or HA epitope tag CARD-7 or CARD-8 fusion proteins or MYC or HA epitope tag target fusion proteins can be adsorbed onto anti-MYC or anti-HA antibody coated microbeads or onto anti-MYC or anti-HA antibody coated microtitre plates, which are then combined with the test compound or the test compound and either the non-adsorbed target protein or CARD-7 or CARD-8 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of CARD-7 or CARD-8 binding or activity determined using standard techniques.

Other techniques for immobilizing proteins on matrices can also be used in the screening assays of the invention. For example, CARD-7 or CARD-8 or its target molecule can be immobilized utilizing conjugation of biotin and streptavidin. Biotinylated CARD-7 or CARD-8 or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with CARD-7 or CARD-8 or target molecules but which do not interfere with binding of the protein to its target molecule can be derivatized to the wells of the plate, and unbound target or protein trapped in the wells by antibody conjugation. Methods for detecting such complexes, in addition to those described above for the GST-immobilized complexes and epitope tag immobilized complexes, include immunodetection of complexes using antibodies reactive with the CARD-7 or CARD-8 or target molecule, as well as enzyme-linked assays which rely on detecting an enzymatic activity associated with CARD-7, CARD-8 or target molecule.

In another embodiment, modulators of CARD-7 or CARD-8 expression are identified in a method in which a cell is contacted with a candidate compound and the expression of the CARD-7 or CARD-8 promoter, mRNA or protein in the cell is determined. The level of expression of CARD-7 or CARD-8 mRNA or protein in the presence of the candidate compound is compared to the level of expression of CARD-7 or CARD-8 mRNA or protein in the absence of the candidate compound. The candidate compound can then be identified as a modulator of CARD-7 or CARD-8 expression based on this comparison. For example, when expression of CARD-7 or CARD-8 mRNA or protein is greater (statistically significantly greater) in the presence of the candidate compound than in its absence, the candidate compound is identified as a stimulator of CARD-7 or CARD-8 mRNA or protein expression. Alternatively, when expression of CARD-7 or CARD-8 MRNA or protein is less (statistically significantly less) in the presence of the candidate compound than in its absence, the candidate compound is identified as an inhibitor of CARD-7 or CARD-8 mRNA or protein expression. The level of CARD-7 or CARD-8 mRNA or protein expression in the cells can be determined by methods described herein for detecting CARD-7 or CARD-8 mRNA or protein. The activity of the CARD-7 or CARD-8 promoter can be assayed by linking the CARD-7 or CARD-8 promoter to a reporter gene such as luciferase, secreted alkaline phosphatase, or beta-galactosidase and introducing the resulting construct into an appropriate vector, transfecting a host cell line, and measuring the activity of the reporter gene in response to test compounds.

In yet another aspect of the invention, the CARD-7 or CARD-8 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with CARD-7 or CARD-8 ("CARD-7 or CARD-8-binding proteins" or "CARD-7 or CARD-8-bp") and modulate CARD-7 or CARD-8 activity. Such CARD-7 or CARD-8-binding proteins are also likely to be involved in the propagation of signals by the CARD-7 or CARD-8 proteins as, for example, upstream or downstream elements of the CARD-7 or CARD-8 pathway.

The two-hybrid system is based on the modular nature of most transcription factors, which consist of separable DNA-binding and activation domains. Briefly, the assay utilizes two different DNA constructs. In one construct, the gene that codes for CARD-7 or CARD-8 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact in vivo, forming a CARD-7 or CARD-8-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with CARD-7 or CARD-8.

In an embodiment of the invention, the ability of a test compound to modulate the activity of CARD-7 or CARD-8, or a biologically active portion thereof can be determined by assaying the ability of the test compound to block the binding of CARD-7 or CARD-8 to its target proteins in a two-hybrid system assay. To screen for test compounds that block the interaction between, e.g., CARD-7 or CARD-8 and their target proteins, which include but are not limited to CARD-5, a yeast two-hybrid screening strain coexpressing the interacting bait and prey constructs, for example, a CARD-7 bait construct and a CARD-5 prey construct as described in the Example above, is contacted with the test compound and the activity of the two-hybrid system reporter gene, usually luciferase, HIS3, lacZ, or URA3 is assayed. If the strain remains viable but exhibits a significant decrease in reporter gene activity, this would indicate that the test compound has inhibited the interaction between the bait and prey proteins. This assay could be automated for high throughput drug screening purposes. In another embodiment of the invention, CARD-7 or CARD-8 and their target proteins could be configured in the reverse two-hybrid system (Vidal et al. (1996) Proc. Natl. Acad. Sci. USA 93:10321–6 and Vidal et al. (1996) Proc. Natl. Acad. Sci. USA 93:10315–20) designed specifically for efficient drug screening. In the reverse two-hybrid system, inhibition of a CARD-7 or CARD-8 physical interaction with a target protein would result in induction of a reporter gene in contrast to the normal two-hybrid system where inhibition of CARD-7 or CARD-8 physical interaction with a target protein would lead to reporter gene repression. The reverse two-hybrid system is preferred for drug screening because reporter gene induction is more easily assayed than report gene repression.

Proteins found to physically interact with proteins that bind to CARD-7 or CARD-8, i.e., CARD-7 or CARD-8 interactors, including but not limited to CARD-5, can be configured into two-hybrid system baits and used in two-hybrid screens to identify additional members of the CARD-7 or CARD-8 pathway. The interactors of CARD-7 or CARD-8 interactors identified in this way could be useful targets for therapeutic intervention in CARD-7 or CARD-8 related diseases and pathologies and an assay of their enzymatic or binding activity could be useful for the identification of test compounds that modulate CARD-7 or CARD-8 activity.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, CARD-7 or CARD-8 nucleic acid molecules described herein or fragments thereof, can be used to map the location of CARD-7 or CARD-8 genes on a chromosome. The mapping of the CARD-7 or CARD-8 sequences to chromosomes is an important first step in correlating these sequences with genes associated with disease.

Briefly, CARD-7 or CARD-8 genes can be mapped to chromosomes by preparing PCR primers (preferably 15–25 bp in length) from the CARD-7 or CARD-8 sequences. Computer analysis of CARD-7 or CARD-8 sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the CARD-7 or CARD-8 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells car, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the CARD-7 or CARD-8 sequences to design oligonucleotide primers, sublocalization can be achieved with panels of fragments from specific chromosomes. Other mapping strategies which can similarly be used to map a CARD-7 or CARD-8 sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature, 325:783–787.

Moreover, differences in the DNA sequences between individuals affected and unaffected with a disease associated with the CARD-7 or CARD-8 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The CARD-7 or CARD-8 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the CARD-7 or CARD-8 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The CARD-7 or CARD-8 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or SEQ ID NO:3 can comfortably provide positive individual identification with a panel of perhaps 10 to 1,000 primers which each yield a noncoding amplified sequence of 100 bases. If predicted coding sequences, such as those in SEQ ID NO:5 or SEQ ID NO:6 are used, a more appropriate number of primers for positive individual identification would be 500–2,000.

If a panel of reagents from CARD-7 or CARD-8 sequences described herein is used to generate a unique identification database for an individual, those same reagents can later be used to identify tissue from that individual. Using the unique identification database, positive identification of the individual, living or dead, can be made from extremely small tissue samples.

3. Use of Partial Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or SEQ ID NO:3 are particularly appropriate for this use as greater numbers of polymorphisms occur in the noncoding regions, making it easier to differentiate individuals using this technique. Examples of polynucleotide reagents include the CARD-7 or CARD-8 sequences or portions thereof, e.g., fragments derived from the noncoding regions of SEQ ID NO:1 or SEQ ID NO:3 which have a length of at least 20 or 30 bases.

The sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such CARD-7 or CARD-8 probes can be used to identify tissue by species and/or by organ type.

In a similar fashion, these reagents, e.g., CARD-7 or CARD-8 primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining CARD-7 or CARD-8 protein and/or nucleic acid expression as well as CARD-7 or CARD-8 activity, in the context of a biological sample (e.g., blood, serum, cells, tissue) to thereby determine whether an individual is afflicted with a disease or disorder, or is at risk of developing a disorder, associated with aberrant CARD-7 or CARD-8 expression or activity. The invention also provides for prognostic (or predictive) assays for determining whether an individual is at risk of developing a disorder associated with CARD-7 or CARD-8 protein, nucleic acid expression or activity. For example, mutations in a CARD-7 or CARD-8 gene can be assayed in a biological sample. Such assays can be used for prognostic or predictive purpose to thereby prophylactically treat an individual prior to the onset of a disorder characterized by or associated with CARD-7 or CARD-8 protein, nucleic acid expression or activity.

Another aspect of the invention provides methods for determining CARD-7 or CARD-8 protein, nucleic acid expression or CARD-7 or CARD-8 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs or other compounds) on the expression or activity of CARD-7 or CARD-8 in clinical trials.

These and other agents are described in further detail in the following sections.

1. Diagnostic Assays

An exemplary method for detecting the presence or absence of CARD-7 or CARD-8 in a biological sample involves obtaining a biological sample from a test subject and contacting the biological sample with a compound or an agent capable of detecting CARD-7 or CARD-8 protein or nucleic acid (e.g., mRNA, genomic DNA) that encodes CARD-7 or CARD-8 protein such that the presence of CARD-7 or CARD-8 is detected in the biological sample. An agent for detecting CARD-7 or CARD-8 mRNA or genomic DNA is a labeled nucleic acid probe capable of hybridizing to CARD-7 or CARD-8 mRNA or genomic DNA. The nucleic acid probe can be, for example, a full-length CARD-7 or CARD-8 nucleic acid, such as the nucleic acid of SEQ ID NO:1, SEQ ID NO:3, SEQ ID NO:5, or SEQ ID NO:6, or a portion thereof, such as an oligonucleotide of at least 15, 30, 50, 100, 250 or 500 nucleotides in length and sufficient to specifically hybridize under stringent conditions to mRNA or genomic DNA. Other suitable probes for use in the diagnostic assays of the invention are described herein.

An agent for detecting CARD-7 or CARD-8 protein can be an antibody capable of binding to CARD-7 or CARD-8 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect CARD-7 or CARD-8 mRNA, protein, or genomic DNA in a biological sample in vitro as well as in vivo. For example, in vitro techniques for detection of CARD-7 or CARD-8 mRNA include Northern hybridizations and in situ hybridizations. In vitro techniques for detection of CARD-7 or CARD-8 protein include enzyme linked immunosorbent assays (ELISAs), Western blots, immunoprecipitations and immunofluorescence. In vitro techniques for detection of CARD-7 or CARD-8 genomic DNA include Southern hybridizations. Furthermore, in vivo techniques for detection of CARD-7 or CARD-8 protein include introducing into a subject a labeled anti-CARD-7 or CARD-8 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting CARD-7 or CARD-8 protein, mRNA, or genomic DNA, such that the presence of CARD-7 or CARD-8 protein, MRNA or genomic DNA is detected in the biological sample, and comparing the presence of CARD-7 or CARD-8 protein, mRNA or genomic DNA in the control sample with the presence of CARD-7 or CARD-8 protein, mRNA or genomic DNA in the test sample.

The invention also encompasses kits for detecting the presence of CARD-7 or CARD-8 in a biological sample (a test sample). Such kits can be used to determine if a subject is suffering from or is at increased risk of developing a disorder associated with aberrant expression of CARD-7 or CARD-8 (e.g., an immunological disorder). For example, the kit can comprise a labeled compound or agent capable of detecting CARD-7 or CARD-8 protein or mRNA in a biological sample and means for determining the amount of CARD-7 or CARD-8 in the sample (e.g., an anti-CARD-7 or CARD-8 antibody or an oligonucleotide probe which binds to DNA encoding CARD-7 or CARD-8. Kits may also include instruction for observing that the tested subject is suffering from or is at risk of developing a disorder associated with aberrant expression of CARD-7 or CARD-8 if the amount of CARD-7 or CARD-8 protein or mRNA is above or below a normal level.

For antibody-based kits, the kit may comprise, for example: (1) a first antibody (e.g., attached to a solid support) which binds to CARD-7 or CARD-8 protein; and, optionally, (2) a second, different antibody which binds to CARD-7 or CARD-8 protein or the first antibody and is conjugated to a detectable agent. For oligonucleotide-based kits, the kit may comprise, for example: (1) an oligonucleotide, e.g., a detectably labelled oligonucleotide, which hybridizes to a CARD-7 or CARD-8 nucleic acid sequence or (2) a pair of primers useful for amplifying a CARD-7 or CARD-8 nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of CARD-7 or CARD-8.

2. Prognostic Assays

The methods described herein can furthermore be utilized as diagnostic or prognostic assays to identify subjects having or at risk of developing a disease or disorder associated with aberrant CARD-7 or CARD-8 expression or activity. For example, the assays described herein, such as the preceding diagnostic assays or the following assays, can be utilized to identify a subject having or at risk of developing a disorder associated with CARD-7 or CARD-8 protein, nucleic acid expression or activity. Alternatively, the prognostic assays can be utilized to identify a subject having or at risk for developing such a disease or disorder. Thus, the present invention provides a method in which a test sample is obtained from a subject and CARD-7 or CARD-8 protein or nucleic acid (e.g., mRNA, genomic DNA) is detected, wherein the presence of CARD-7 or CARD-8 protein or nucleic acid is diagnostic for a subject having or at risk of developing a disease or disorder associated with aberrant CARD-7 or CARD-8 expression or activity. As used herein, a "test sample" refers to a biological sample obtained from a subject of interest. For example, a test sample can be a biological fluid (e.g., serum), cell sample, or tissue. Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant CARD-7 or CARD-8 expression or activity. For example, such methods can be used to determine whether a subject can be effectively treated with a specific agent or class of agents (e.g., agents of a type which decrease CARD-7 or CARD-8 activity). Thus, the present invention provides methods for determining whether a subject can be effectively treated with an agent for a disorder associated with aberrant CARD-7 or CARD-8 expression or activity in which a test sample is obtained and CARD-7 or CARD-8 protein or nucleic acid is detected (e.g., wherein the presence of CARD-7 or CARD-8 protein or nucleic acid is diagnostic for a subject that can be administered the agent to treat a disorder associated with aberrant CARD-7 or CARD-8 expression or activity).

The methods of the invention can also be used to detect genetic lesions or mutations in a CARD-7 or CARD-8 gene, thereby determining if a subject with the lesioned gene is at risk for a disorder characterized by aberrant cell proliferation and/or differentiation. In preferred embodiments the methods include detecting, in a sample of cells from the subject, the presence or absence of a genetic lesion characterized by at least one of an alteration affecting the integrity of a gene encoding a CARD-7 or CARD-8-protein, or the mis-expression of the CARD-7 or CARD-8 gene. For example, such genetic lesions can be detected by ascertaining the existence of at least one of 1) a deletion of one or more nucleotides from a CARD-7 or CARD-8 gene; 2) an addition of one or more nucleotides to a CARD-7 or CARD-8 gene; 3) a substitution of one or more nucleotides of a CARD-7 or CARD-8 gene; 4) a chromosomal rearrangement of a CARD-7 or CARD-8 gene; 5) an alteration in the level of a messenger RNA transcript of a CARD-7 or CARD-8 gene; 6) aberrant modification of a CARD-7 or CARD-8 gene, such as of the methylation pattern of the genomic DNA; 7) the presence of a non-wild type splicing pattern of a messenger RNA transcript of a CARD-7 or CARD-8 gene (e.g, caused by a mutation in a splice donor or splice acceptor site); 8) a non-wild type level of a CARD-7 or CARD-8-protein; 9) allelic loss of a CARD-7 or CARD-8 gene; and 10) inappropriate post-translational modification of a CARD-7 or CARD-8-protein. As described herein, there are a large number of assay techniques known in the art which can be used for detecting lesions in a CARD-7 or CARD-8 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in the CARD-7 or CARD-9-gene (see, e.g., Abravaya et al. (1995) Nucleic Acids Res. 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a CARD-7 or CARD-8 gene under conditions such that hybridization and amplification of the CARD-7 or CARD-8-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) Proc. Natl. Acad. Sci. USA 87:1874–1878), transcriptional amplification system (Kwoh, et al. (1989) Proc. Natl. Acad. Sci. USA 86:1173–1177), Q-Beta Replicase (Lizardi et al. (1988) Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a CARD-7 or CARD-8 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498, 531) can be used to score for the presence of specific mutations by development or loss of a ribozyme cleavage site.

In other embodiments, genetic mutations in CARD-7 or CARD-8 can be identified by hybridizing a sample and control nucleic acids, e.g., DNA or RNA, to high density arrays containing hundreds or thousands of oligonucleotides probes (Cronin et al. (1996) Human Mutation 7:244–255; Kozal et al. (1996) Nature Medicine 2:753–759). For example, genetic mutations in CARD-7 or CARD-8 can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the CARD-7 or CARD-8 gene and detect mutations by comparing the sequence of the sample CARD-7 or CARD-8 with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Bio/Techniques 19:448), including sequencing by mass spectrometry (see, e.g., PCT Publication No. WO 94/16101; Cohen et al. (1996) Adv. Chromatogr. 36:127–162; and Griffin et al. (1993) Appl. Biochem. Biotechnol. 38:147–159).

Other methods for detecting mutations in the CARD-7 or CARD-8 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes of formed by hybridizing (labeled) RNA or DNA containing the wild-type CARD-7 or CARD-8 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al (1988) Proc. Natl Acad Sci USA 85:4397; Saleeba et al (1992) Methods Enzymol. 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in CARD-7 or CARD-8 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on a CARD-7 or CARD-8 sequence, e.g., a wild-type CARD-7 or CARD-8 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in CARD-7 or CARD-8 genes. For example, single strand conformation polymorphism (SSCP) may be used to detect differences in electrophoretic mobility between mutant and wild type nucleic acids (Orita et al. (1989) Proc Natl. Acad. Sci USA: 86:2766, see also Cotton (1993) Mutat. Res. 285:125–144; and Hayashi (1992) Genet Anal Tech Appl 9:73–79). Single-stranded DNA fragments of sample and control CARD-7 or CARD-8 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163); Saiki et al. (1989) Proc. Natl Acad. Sci USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437–2448) or at the extreme 3' end of one primer where, under appropriate conditions, mismatch can prevent, or reduce polymerase extension (Prossner (1993) Tibtech 11:238). In addition, it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a CARD-7 or CARD-8 gene.

Furthermore, any cell type or tissue, preferably peripheral blood leukocytes, in which CARD-7 or CARD-8 is expressed may be utilized in the prognostic assays described herein.

3. Pharmacogenomics

Agents, or modulators which have a stimulatory or inhibitory effect on CARD-7 or CARD-8 activity (e.g., CARD-7 or CARD-8 gene expression) as identified by a screening assay described herein can be administered to individuals to treat (prophylactically or therapeutically) disorders (e.g., an immunological disorder) associated with aberrant CARD-7 or CARD-8 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of CARD-7 or CARD-8 protein, expression of CARD-7 or CARD-8 nucleic acid, or mutation content of CARD-7 or CARD-8 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug.

These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the ultra-rapid metabolizers who do not respond to standard doses. Recently, the molecular basis of ultra-rapid metabolism has been identified to be due to CYP2D6 gene amplification.

Thus, the activity of CARD-7 or CARD-8 protein, expression of CARD-7 or CARD-8 nucleic acid, or mutation content of CARD-7 or CARD-8 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a CARD-7 or CARD-8 modulator, such as a modulator identified by one of the exemplary screening assays described herein.

4. Monitoring of Effects During Clinical Trials

Monitoring the influence of agents (e.g., drugs, compounds) on the expression or activity of CARD-7 or CARD-8 (e.g., the ability to modulate aberrant cell proliferation and/or differentiation) can be applied not only in basic drug screening, but also in clinical trials. For example, the effectiveness of an agent determined by a screening assay as described herein to increase CARD-7 or CARD-8 gene expression, protein levels, or upregulate CARD-7 or CARD-8 activity, can be monitored in clinical trails of subjects exhibiting decreased CARD-7 or CARD-8 gene expression, protein levels, or downregulated CARD-7 or CARD-8 activity. Alternatively, the effectiveness of an agent determined by a screening assay to decrease CARD-7 or CARD-8 gene expression, protein levels, or downregulated CARD-7 or CARD-8 activity, can be monitored in clinical trials of subjects exhibiting increased CARD-7 or CARD-8 gene expression, protein levels, or upregulated CARD-7 or CARD-8 activity. In such clinical trials, the expression or activity of CARD-7 or CARD-8 and, preferably, other genes that have been implicated in, for example, a cellular proliferation disorder can be used as a "read out" or markers of the immune responsiveness of a particular cell.

For example, and not by way of limitation, genes, including CARD-7 or CARD-8, that are modulated in cells by treatment with an agent (e.g., compound, drug or small molecule) which modulates CARD-7 or CARD-8 activity (e.g., identified in a screening assay as described herein) can be identified. Thus, to study the effect of agents on cellular proliferation disorders, for example, in a clinical trial, cells can be isolated and RNA prepared and analyzed for the levels of expression of CARD-7 or CARD-8 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of CARD-7 or CARD-8 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a CARD-7 or CARD-8 protein, mRNA, or genomic DNA in the preadministration sample; (iii) obtaining one or more post-administration samples from the subject; (iv) detecting the level of expression or activity of the CARD-7 or CARD-8 protein, mRNA, or genomic DNA in the post-administration samples; (v) comparing the level of expression or activity of the CARD-7 or CARD-8 protein, mRNA, or genomic DNA in the pre-administration sample with the CARD-7 or CARD-8 protein, mRNA, or genomic DNA in the post administration sample or samples; and (vi) altering the administration of the agent to the subject accordingly. For example, increased administration of the agent may be desirable to increase the expression or activity of CARD-7 or CARD-8 to higher levels than detected, i.e., to increase the effectiveness of the agent. Alternatively, decreased administration of the agent may be desirable to decrease expression or activity of CARD-7 or CARD-8 to lower levels than detected, i.e., to decrease the effectiveness of the agent.

5. Transcriptional Profiling

The CARD-7 and CARD-8 nucleic acid molecules described herein, including small oligonucleotides, can be used in transcriptionally profiling. For example, these nucleic acids can be used to examine the expression of CARD-7 and CARD-8 in normal tissue or cells and in tissue or cells subject to a disease state, e.g., tissue or cells derived from a patient having a disease of interest or cultured cells which model or reflect a disease state of interest, e.g., cells of a cultured tumor cell line. By measuring expression of CARD-7 and CARD-8, together or individually, a profile of expression in normal and disease states can be developed. This profile can be used diagnostically and to examine the effectiveness of a therapeutic regime.

C. Methods of Treatment

The present invention provides for both prophylactic and therapeutic methods of treating a subject at risk of (or susceptible to) a disorder or having a disorder associated with aberrant CARD-7 or CARD-8 expression or activity, examples of which are provided herein.

1. Prophylactic Methods

In one aspect, the invention provides a method for preventing in a subject, a disease or condition associated with an aberrant CARD-7 or CARD-8 expression or activity, by administering to the subject an agent which modulates CARD-7 or CARD-8 expression or at least one CARD-7 or CARD-8 activity. Subjects at risk for a disease which is caused or contributed to by aberrant CARD-7 or CARD-8 expression or activity can be identified by, for example, any or a combination of diagnostic or prognostic assays as described herein. Administration of a prophylactic agent can occur prior to the manifestation of symptoms characteristic of the CARD-7 or CARD-8 aberrancy, such that a disease or disorder is prevented or, alternatively, delayed in its progression. Depending on the type of CARD-7 or CARD-8 aberrancy, for example, a CARD-7 or CARD-8 agonist or CARD-7 or CARD-8 antagonist agent can be used for treating the subject. The appropriate agent can be determined based on screening assays described herein. Activities of CARD-7 or CARD-8 that could be modulated for prophylactic purposes include, but are not limited to: 1) CARD-7 or CARD-8 gene or protein expression; and 2) CARD-7 or CARD-8 binding to a target protein.

2. Therapeutic Methods

Another aspect of the invention pertains to methods of modulating CARD-7 or CARD-8 expression or activity for therapeutic purposes. The modulatory method of the invention involves contacting a cell with an agent that modulates one or more of the activities of CARD-7 or CARD-8 protein activity associated with the cell. An agent that modulates CARD-7 or CARD-8 protein activity can be an agent as described herein, such as a nucleic acid or a protein, a naturally-occurring cognate ligand of a CARD-7 or CARD-8 protein, a peptide, a CARD-7 or CARD-8 peptidomimetic, or other small molecule. In one embodiment, the agent stimulates one or more of the biological activities of CARD-7 or CARD-8 protein. Examples of such stimulatory agents include active CARD-7 or CARD-8 protein and a nucleic acid molecule encoding CARD-7 or CARD-8 that has been introduced into the cell. In another embodiment, the agent inhibits one or more of the biological activities of CARD-7 or CARD-8 protein. Examples of such inhibitory agents include antisense CARD-7 or CARD-8 nucleic acid molecules and anti-CARD-7 or CARD-8 antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a CARD-7 or CARD-8 protein or nucleic acid molecule or a disorder related to CARD-7 or CARD-8 expression or activity. In one embodiment, the method involves administering an agent (e.g., an agent identified by a screening assay described herein), or combination of agents that modulates (e.g., upregulates or downregulates) CARD-7 or CARD-8 expression or activity. In another embodiment, the method involves administering a CARD-7 or CARD-8 protein or nucleic acid molecule as therapy to compensate for reduced or aberrant CARD-7 or CARD-8 expression or activity. Activities of CARD-7 or CARD-8 that could be modulated for therapeutic purposes include, but are not limited to: 1) CARD-7 or CARD-8 gene or protein expression; 2) CARD-7 or CARD-8 binding to a target protein.

Stimulation of CARD-7 or CARD-8 activity is desirable in situations in which CARD-7 or CARD-8 is abnormally downregulated and/or in which increased CARD-7 or CARD-8 activity is likely to have a beneficial effect. Conversely, inhibition of CARD-7 or CARD-8 activity is desirable in situations in which CARD-7 or CARD-8 is abnormally upregulated, e.g., in myocardial infarction, and/or in which decreased CARD-7 or CARD-8 activity is likely to have a beneficial effect.

This invention is further illustrated by the following examples which should not be construed as limiting. The contents of all references, patents and published patent applications cited throughout this application are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

<160> NUMBER OF SEQ ID NOS: 10

<210> SEQ ID NO 1
<211> LENGTH: 5444
<212> TYPE: DNA
<213> ORGANISM: Homo sapiens
<220> FEATURE:
<221> NAME/KEY: CDS
<222> LOCATION: (523)...(4809)

<400> SEQUENCE: 1

| | | | | | |
|---|---|---|---|---|---|
| gccccagggc | ctggagaggt | ctgaagaaac | ctgggagcca | gcagcccggg | gctccactct | 60 |
| gggttctgaa | agcccattcc | ctgctctgcg | gctcctccca | ccccacctct | tctcagcctt | 120 |
| gcagctcaag | ggttgatctc | aggagtccag | gacccaggag | agggaagaat | ctgaggaaca | 180 |
| cagaacagtg | agcgttgccc | acaccccatc | tcccgtcacc | acatctcccc | tcaccctcac | 240 |
| cctccctgcc | tggccctgga | ccccatccca | ggacctccct | atcagctgac | ttcttccagt | 300 |
| gtcttgcagg | ccctctggg | ctcctccctc | ccctggcttt | tcctaccact | cccctctat | 360 |
| cggcgtctat | ctgtaggtgc | cctgggattt | ataaaactgg | gttccgaatg | ctgaataaga | 420 |
| gacggtaaga | gccaaggcaa | aggacagcac | tgttctctgc | ctgcctgata | ccctcaccac | 480 |
| ctgggaacat | ccccagaca | ccctcttaac | tccgggacag | ag atg gct ggc gga | | 534 |

-continued

```
                                    Met Ala Gly Gly
                                    1
gcc tgg ggc cgc ctg gcc tgt tac ttg gag ttc ctg aag aag gag gag    582
Ala Trp Gly Arg Leu Ala Cys Tyr Leu Glu Phe Leu Lys Lys Glu Glu
  5              10                  15                  20 ctg aag gag ttc cag ctt ctg ctc gcc aat aaa gcg cac tcc agg agc    630
Leu Lys Glu Phe Gln Leu Leu Leu Ala Asn Lys Ala His Ser Arg Ser
             25                  30                  35 tct tcg ggt gag aca ccc gct cag cca gag aag acg agt ggc atg gag    678
Ser Ser Gly Glu Thr Pro Ala Gln Pro Glu Lys Thr Ser Gly Met Glu
         40                  45                  50 gtg gcc tcg tac ctg gtg gct cag tat ggg gag cag cgg gcc tgg gac    726
Val Ala Ser Tyr Leu Val Ala Gln Tyr Gly Glu Gln Arg Ala Trp Asp
     55                  60                  65 cta gcc ctc cat acc tgg gag cag atg ggg ctg agg tca ctg tgc gcc    774
Leu Ala Leu His Thr Trp Glu Gln Met Gly Leu Arg Ser Leu Cys Ala
 70                  75                  80 caa gcc cag gaa ggg gca ggc cac tct ccc tca ttc ccc tac agc cca    822
Gln Ala Gln Glu Gly Ala Gly His Ser Pro Ser Phe Pro Tyr Ser Pro
 85                  90                  95                 100 agt gaa ccc cac ctg ggg tct ccc agc caa ccc acc tcc acc gca gtg    870
Ser Glu Pro His Leu Gly Ser Pro Ser Gln Pro Thr Ser Thr Ala Val
                105                 110                 115 cta atg ccc tgg atc cat gaa ttg ccg gcg ggg tgc acc cag ggc tca    918
Leu Met Pro Trp Ile His Glu Leu Pro Ala Gly Cys Thr Gln Gly Ser
            120                 125                 130 gag aga agg gtt ttg aga cag ctg cct gac aca tct gga cgc cgc tgg    966
Glu Arg Arg Val Leu Arg Gln Leu Pro Asp Thr Ser Gly Arg Arg Trp
        135                 140                 145 aga gaa atc tct gcc tca ctc ctc tac caa gct ctt cca agc tcc cca   1014
Arg Glu Ile Ser Ala Ser Leu Leu Tyr Gln Ala Leu Pro Ser Ser Pro
    150                 155                 160 gac cat gag tct cca agc cag gag tca ccc aac gcc ccc aca tcc aca   1062
Asp His Glu Ser Pro Ser Gln Glu Ser Pro Asn Ala Pro Thr Ser Thr
165                 170                 175                 180 gca gtg ctg ggg agc tgg gga tcc cca cct cag ccc agc cta gca ccc   1110
Ala Val Leu Gly Ser Trp Gly Ser Pro Pro Gln Pro Ser Leu Ala Pro
                185                 190                 195 aga gag cag gag gct cct ggg acc caa tgg cct ctg gat gaa acg tca   1158
Arg Glu Gln Glu Ala Pro Gly Thr Gln Trp Pro Leu Asp Glu Thr Ser
            200                 205                 210 gga att tac tac aca gaa atc aga gaa aga gag aga gag aaa tca gag   1206
Gly Ile Tyr Tyr Thr Glu Ile Arg Glu Arg Glu Arg Glu Lys Ser Glu
        215                 220                 225 aaa ggc agg ccc cca tgg gca gcg gtg gta gga acg ccc cca cag gcg   1254
Lys Gly Arg Pro Pro Trp Ala Ala Val Val Gly Thr Pro Pro Gln Ala
    230                 235                 240 cac acc agc cta cag ccc cac cac cac cca tgg gag cct tct gtg aga   1302
His Thr Ser Leu Gln Pro His His His Pro Trp Glu Pro Ser Val Arg
245                 250                 255                 260 gag agc ctc tgt tcc aca tgg ccc tgg aaa aat gag gat ttt aac caa   1350
Glu Ser Leu Cys Ser Thr Trp Pro Trp Lys Asn Glu Asp Phe Asn Gln
                265                 270                 275 aaa ttc aca cag ctg cta ctt cta caa aga cct cac ccc aga agc caa   1398
Lys Phe Thr Gln Leu Leu Leu Leu Gln Arg Pro His Pro Arg Ser Gln
            280                 285                 290 gat ccc ctg gtc aag aga agc tgg cct gat tat gtg gag gag aat cga   1446
Asp Pro Leu Val Lys Arg Ser Trp Pro Asp Tyr Val Glu Glu Asn Arg
        295                 300                 305
```

```
gga cat tta att gag atc aga gac tta ttt ggc cca ggc ctg gat acc      1494
Gly His Leu Ile Glu Ile Arg Asp Leu Phe Gly Pro Gly Leu Asp Thr
310             315                 320 caa gaa cct cgc ata gtc ata ctg cag ggg gct gct gga att ggg aag      1542
Gln Glu Pro Arg Ile Val Ile Leu Gln Gly Ala Ala Gly Ile Gly Lys
325             330                 335                 340 tca aca ctg gcc agg cag gtg aag gaa gcc tgg ggg aga ggc cag ctg      1590
Ser Thr Leu Ala Arg Gln Val Lys Glu Ala Trp Gly Arg Gly Gln Leu
                345                 350                 355 tat ggg gac cgc ttc cag cat gtc ttc tac ttc agc tgc aga gag ctg      1638
Tyr Gly Asp Arg Phe Gln His Val Phe Tyr Phe Ser Cys Arg Glu Leu
                360                 365                 370 gcc cag tcc aag gtg gtg agt ctc gct gag ctc atc gga aaa gat ggg      1686
Ala Gln Ser Lys Val Val Ser Leu Ala Glu Leu Ile Gly Lys Asp Gly
                375                 380                 385 aca gcc act ccg gct ccc att aga cag atc ctg tct agg cca gag cgg      1734
Thr Ala Thr Pro Ala Pro Ile Arg Gln Ile Leu Ser Arg Pro Glu Arg
390             395                 400 ctg ctc ttc atc ctc gat ggt gta gat gag cca gga tgg gtc ttg cag      1782
Leu Leu Phe Ile Leu Asp Gly Val Asp Glu Pro Gly Trp Val Leu Gln
405             410                 415                 420 gag ccg agt tct gag ctc tgt ctg cac tgg agc cag cca cag ccg gcg      1830
Glu Pro Ser Ser Glu Leu Cys Leu His Trp Ser Gln Pro Gln Pro Ala
                425                 430                 435 gat gca ctg ctg ggc agt ttg ctg ggg aaa act ata ctt ccc gag gca      1878
Asp Ala Leu Leu Gly Ser Leu Leu Gly Lys Thr Ile Leu Pro Glu Ala
                440                 445                 450 tcc ttc ctg atc acg gct cgg acc aca gct ctg cag aac ctc att cct      1926
Ser Phe Leu Ile Thr Ala Arg Thr Thr Ala Leu Gln Asn Leu Ile Pro
                455                 460                 465 tct ttg gag cag gca cgt tgg gta gag gtc ctg ggg ttc tct gag tcc      1974
Ser Leu Glu Gln Ala Arg Trp Val Glu Val Leu Gly Phe Ser Glu Ser
470             475                 480 agc agg aag gaa tat ttc tac aga tat ttc aca gat gaa agg caa gca      2022
Ser Arg Lys Glu Tyr Phe Tyr Arg Tyr Phe Thr Asp Glu Arg Gln Ala
485             490                 495                 500 att aga gcc ttt agg ttg gtc aaa tca aac aaa gag ctc tgg gcc ctg      2070
Ile Arg Ala Phe Arg Leu Val Lys Ser Asn Lys Glu Leu Trp Ala Leu
                505                 510                 515 tgt ctt gtg ccc tgg gtg tcc tgg ctg gcc tgc act tgc ctg atg cag      2118
Cys Leu Val Pro Trp Val Ser Trp Leu Ala Cys Thr Cys Leu Met Gln
                520                 525                 530 cag atg aag cgg aag gaa aaa ctc aca ctg act tcc aag acc acc aca      2166
Gln Met Lys Arg Lys Glu Lys Leu Thr Leu Thr Ser Lys Thr Thr Thr
                535                 540                 545 acc ctc tgt cta cat tac ctt gcc cag gct ctc caa gct cag cca ttg      2214
Thr Leu Cys Leu His Tyr Leu Ala Gln Ala Leu Gln Ala Gln Pro Leu
550             555                 560 gga ccc cag ctc aga gac ctc tgc tct ctg gct gct gag ggc atc tgg      2262
Gly Pro Gln Leu Arg Asp Leu Cys Ser Leu Ala Ala Glu Gly Ile Trp
565             570                 575                 580 caa aaa aag acc ctt ttc agt cca gat gac ctc agg aag cat ggg tta      2310
Gln Lys Lys Thr Leu Phe Ser Pro Asp Asp Leu Arg Lys His Gly Leu
                585                 590                 595 gat ggg gcc atc atc tcc acc ttc ttg aag atg ggt att ctt caa gag      2358
Asp Gly Ala Ile Ile Ser Thr Phe Leu Lys Met Gly Ile Leu Gln Glu
                600                 605                 610 cac ccc atc cct ctg agc tac agc ttc att cac ctc tgt ttc caa gag      2406
His Pro Ile Pro Leu Ser Tyr Ser Phe Ile His Leu Cys Phe Gln Glu
                615                 620                 625
```

-continued

| | |
|---|---|
| ttc ttt gca gca atg tcc tat gtc ttg gag gat gag aag ggg aga ggt<br>Phe Phe Ala Ala Met Ser Tyr Val Leu Glu Asp Glu Lys Gly Arg Gly<br>630                        635                     640 | 2454 |
| aaa cat tct aat tgc atc ata gat ttg gaa aag acg cta gaa gca tat<br>Lys His Ser Asn Cys Ile Ile Asp Leu Glu Lys Thr Leu Glu Ala Tyr<br>645                        650                     655                     660 | 2502 |
| gga ata cat ggc ctg ttt ggg gca tca acc aca cgt ttc cta ttg ggc<br>Gly Ile His Gly Leu Phe Gly Ala Ser Thr Thr Arg Phe Leu Leu Gly<br>                        665                     670                     675 | 2550 |
| ctg tta agt gat gag ggg gag aga gag atg gag aac atc ttt cac tgc<br>Leu Leu Ser Asp Glu Gly Glu Arg Glu Met Glu Asn Ile Phe His Cys<br>                680                     685                     690 | 2598 |
| cgg ctg tct cag ggg agg aac ctg atg cag tgg gtc ccg tcc ctg cag<br>Arg Leu Ser Gln Gly Arg Asn Leu Met Gln Trp Val Pro Ser Leu Gln<br>695                        700                     705 | 2646 |
| ctg ctg ctg cag cca cac tct ctg gag tcc ctc cac tgc ttg tac gag<br>Leu Leu Leu Gln Pro His Ser Leu Glu Ser Leu His Cys Leu Tyr Glu<br>             710                     715                     720 | 2694 |
| act cgg aac aaa acg ttc ctg aca caa gtg atg gcc cat ttc gaa gaa<br>Thr Arg Asn Lys Thr Phe Leu Thr Gln Val Met Ala His Phe Glu Glu<br>725                        730                     735                     740 | 2742 |
| atg ggc atg tgt gta gaa aca gac atg gag ctc tta gtg tgc act ttc<br>Met Gly Met Cys Val Glu Thr Asp Met Glu Leu Leu Val Cys Thr Phe<br>                        745                     750                     755 | 2790 |
| tgc att aaa ttc agc cgc cac gtg aag aag ctt cag ctg att gag ggc<br>Cys Ile Lys Phe Ser Arg His Val Lys Lys Leu Gln Leu Ile Glu Gly<br>             760                     765                     770 | 2838 |
| agg cag cac aga tca aca tgg agc ccc acc atg gta gtc ctg ttc agg<br>Arg Gln His Arg Ser Thr Trp Ser Pro Thr Met Val Val Leu Phe Arg<br>775                        780                     785 | 2886 |
| tgg gtc cca gtc aca gat gcc tat tgg cag att ctc ttc tcc gtc ctc<br>Trp Val Pro Val Thr Asp Ala Tyr Trp Gln Ile Leu Phe Ser Val Leu<br>             790                     795                     800 | 2934 |
| aag gtc acc aga aac ctg aag gag ctg gac cta agt gga aac tcg ctg<br>Lys Val Thr Arg Asn Leu Lys Glu Leu Asp Leu Ser Gly Asn Ser Leu<br>805                        810                     815                     820 | 2982 |
| agc cac tct gca gtg aag agt ctt tgt aag acc ctg aga cgc cct cgc<br>Ser His Ser Ala Val Lys Ser Leu Cys Lys Thr Leu Arg Arg Pro Arg<br>                        825                     830                     835 | 3030 |
| tgc ctc ctg gag acc ctg cgg ttg gct ggc tgt ggc ctc aca gct gag<br>Cys Leu Leu Glu Thr Leu Arg Leu Ala Gly Cys Gly Leu Thr Ala Glu<br>             840                     845                     850 | 3078 |
| gac tgc aag gac ctt gcc ttt ggg ctg aga gcc aac cag acc ctg acc<br>Asp Cys Lys Asp Leu Ala Phe Gly Leu Arg Ala Asn Gln Thr Leu Thr<br>                855                     860                     865 | 3126 |
| gag ctg gac ctg agc ttc aat gtg ctc acg gat gct gga gcc aaa cac<br>Glu Leu Asp Leu Ser Phe Asn Val Leu Thr Asp Ala Gly Ala Lys His<br>870                        875                     880 | 3174 |
| ctt tgc cag aga ctg aga cag ccg agc tgc aag cta cag cga ctg cag<br>Leu Cys Gln Arg Leu Arg Gln Pro Ser Cys Lys Leu Gln Arg Leu Gln<br>885                        890                     895                     900 | 3222 |
| ctg gtc agc tgt ggc ctc acg tct gac tgc tgc cag gac ctg gcc tct<br>Leu Val Ser Cys Gly Leu Thr Ser Asp Cys Cys Gln Asp Leu Ala Ser<br>                        905                     910                     915 | 3270 |
| gtg ctt agt gcc agc ccc agc ctg aag gag cta gac ctg cag cag aac<br>Val Leu Ser Ala Ser Pro Ser Leu Lys Glu Leu Asp Leu Gln Gln Asn<br>                920                     925                     930 | 3318 |
| aac ctg gat gac gtt ggc gtg cga ctg ctc tgt gag ggg ctc agg cat<br>Asn Leu Asp Asp Val Gly Val Arg Leu Leu Cys Glu Gly Leu Arg His | 3366 |

```
                935                 940                  945
cct gcc tgc aaa ctc ata cgc ctg ggg ctg gac cag aca act ctg agt       3414
Pro Ala Cys Lys Leu Ile Arg Leu Gly Leu Asp Gln Thr Thr Leu Ser
    950                 955                 960 gat gag atg agg cag gaa ctg agg gcc ctg gag cag gag aaa cct cag       3462
Asp Glu Met Arg Gln Glu Leu Arg Ala Leu Glu Gln Glu Lys Pro Gln
965                 970                 975                 980 ctg ctc atc ttc agc aga cgg aaa cca agt gtg atg acc cct act gag       3510
Leu Leu Ile Phe Ser Arg Arg Lys Pro Ser Val Met Thr Pro Thr Glu
                985                 990                 995 ggc ctg gat acg gga gag atg agt aat agc aca tcc tca ctc aag cgg       3558
Gly Leu Asp Thr Gly Glu Met Ser Asn Ser Thr Ser Ser Leu Lys Arg
            1000                1005                1010 cag aga ctc gga tca gag agg gcg gct tcc cat gtt gct cag gct aat       3606
Gln Arg Leu Gly Ser Glu Arg Ala Ala Ser His Val Ala Gln Ala Asn
        1015                1020                1025 ctc aaa ctc ctg gac gtg agc aag atc ttc cca att gct gag att gca       3654
Leu Lys Leu Leu Asp Val Ser Lys Ile Phe Pro Ile Ala Glu Ile Ala
    1030                1035                1040 gag gaa agc tcc cca gag gta gta ccg gtg aac ctc ttg tgc gtg cct       3702
Glu Glu Ser Ser Pro Glu Val Val Pro Val Glu Leu Leu Cys Val Pro
1045                1050                1055                1060 tct cct gcc tct caa ggg gac ctg cat acg aag cct ttg gga act gac       3750
Ser Pro Ala Ser Gln Gly Asp Leu His Thr Lys Pro Leu Gly Thr Asp
                1065                1070                1075 gat gac ttc tgg ggc ccc acg ggg cct gtg gct act gag gta gtt gac       3798
Asp Asp Phe Trp Gly Pro Thr Gly Pro Val Ala Thr Glu Val Val Asp
            1080                1085                1090 aaa gaa aag aac ttg tac cga gtt cac ttc cct gta gct ggc tcc tac       3846
Lys Glu Lys Asn Leu Tyr Arg Val His Phe Pro Val Ala Gly Ser Tyr
        1095                1100                1105 cgc tgg ccc aac acg ggt ctc tgc ttt gtg atg aga gaa gcg gtg acc       3894
Arg Trp Pro Asn Thr Gly Leu Cys Phe Val Met Arg Glu Ala Val Thr
    1110                1115                1120 gtt gag att gaa ttc tgt gtg tgg gac cag ttc ctg ggt gag atc aac       3942
Val Glu Ile Glu Phe Cys Val Trp Asp Gln Phe Leu Gly Glu Ile Asn
1125                1130                1135                1140 cca cag cac agc tgg atg gtg gca ggg cct ctg ctg gac atc aag gct       3990
Pro Gln His Ser Trp Met Val Ala Gly Pro Leu Leu Asp Ile Lys Ala
                1145                1150                1155 gag cct gga gct gtg gaa gct gtg cac ctc cct cac ttt gtg gct ctc       4038
Glu Pro Gly Ala Val Glu Ala Val His Leu Pro His Phe Val Ala Leu
            1160                1165                1170 caa ggg ggc cat gtg gac aca tcc ctg ttc caa atg gcc cac ttt aaa       4086
Gln Gly Gly His Val Asp Thr Ser Leu Phe Gln Met Ala His Phe Lys
        1175                1180                1185 gag gag ggg atg ctc ctg gag aag cca gcc agg gtg gag ctg cat cac       4134
Glu Glu Gly Met Leu Leu Glu Lys Pro Ala Arg Val Glu Leu His His
    1190                1195                1200 ata gtt ctg gaa aac ccc agc ttc tcc ccc ttg gga gtc ctc ctg aaa       4182
Ile Val Leu Glu Asn Pro Ser Phe Ser Pro Leu Gly Val Leu Leu Lys
1205                1210                1215                1220 atg atc cat aat gcc ctg cgc ttc att ccc gtc acc tct gtg gtg ttg       4230
Met Ile His Asn Ala Leu Arg Phe Ile Pro Val Thr Ser Val Val Leu
                1225                1230                1235 ctt tac cac cgc gtc cat cct gag gaa gtc acc ttc cac ctc tac ctg       4278
Leu Tyr His Arg Val His Pro Glu Glu Val Thr Phe His Leu Tyr Leu
            1240                1245                1250 atc cca agt gac tgc tcc att cgg aag gaa ctg gag ctc tgc tat cga       4326
```

```
Ile Pro Ser Asp Cys Ser Ile Arg Lys Glu Leu Glu Leu Cys Tyr Arg
        1255                1260                1265 agc cct gga gaa gac cag ctg ttc tcg gag ttc tac gtt ggc cac ttg    4374
Ser Pro Gly Glu Asp Gln Leu Phe Ser Glu Phe Tyr Val Gly His Leu
    1270                1275                1280 gga tca ggg atc agg ctg caa gtg aaa gac aag aaa gat gag act ctg    4422
Gly Ser Gly Ile Arg Leu Gln Val Lys Asp Lys Lys Asp Glu Thr Leu
1285                1290                1295                1300 gtg tgg gag gcc ttg gtg aaa cca gga gat ctc atg cct gca act act    4470
Val Trp Glu Ala Leu Val Lys Pro Gly Asp Leu Met Pro Ala Thr Thr
            1305                1310                1315 ctg atc cct cca gcc cgc ata gcc gta cct tca cct ctg gat gcc ccg    4518
Leu Ile Pro Pro Ala Arg Ile Ala Val Pro Ser Pro Leu Asp Ala Pro
                1320                1325                1330 cag ttg ctg cac ttt gtg gac cag tat cga gag cag ctg ata gcc cga    4566
Gln Leu Leu His Phe Val Asp Gln Tyr Arg Glu Gln Leu Ile Ala Arg
        1335                1340                1345 gtg aca tcg gtg gag gtt gtc ttg gac aaa ctg cat gga cag gtg ctg    4614
Val Thr Ser Val Glu Val Val Leu Asp Lys Leu His Gly Gln Val Leu
    1350                1355                1360 agc cag gag cag tac gag agg gtg ctg gct gag aac acg agg ccc agc    4662
Ser Gln Glu Gln Tyr Glu Arg Val Leu Ala Glu Asn Thr Arg Pro Ser
1365                1370                1375                1380 cag atg cgg aag ctg ttc agc ttg agc cag tcc tgg gac cgg aag tgc    4710
Gln Met Arg Lys Leu Phe Ser Leu Ser Gln Ser Trp Asp Arg Lys Cys
            1385                1390                1395 aaa gat gga ctc tac caa gcc ctg aag gag acc cat cct cac ctc att    4758
Lys Asp Gly Leu Tyr Gln Ala Leu Lys Glu Thr His Pro His Leu Ile
                1400                1405                1410 atg gaa ctc tgg gag aag ggc agc aaa aag gga ctc ctg cca ctc agc    4806
Met Glu Leu Trp Glu Lys Gly Ser Lys Lys Gly Leu Leu Pro Leu Ser
        1415                1420                1425 agc tgaagtatca acaccagccc ttgacccttg agtcctggct ttggctgacc         4859
Ser cttctttggg tctcagtttc tttctctgca acaagttgc catctggttt gccttccagc   4919
actaaagtaa tggaactttg atgatgcctt tgctgggcat tatgtgtcca tgccagggat  4979
gccacagggg gccccagtcc aggtggccta acagcatctc agggaatgtc catctggagc  5039
tggcaagacc cctgcagacc tcatagagcc tcatctggtg gccacagcag ccaagcctag  5099
agccctccgg atcccatcca ggcgcaaaga ggaataggag ggacatggaa ccatttgcct  5159
ctggctgtgt cacagggtga gccccaaaat tggggttcag cgtgggaggc cacgtggatt  5219
cttggctttg tacaggaaga tctacaagag caagccaaca gagtaaagtg gaaggaagtt  5279
tattcagaaa ataaaggagt atcacagctc ttttagaatt tgtctagcag gctttccagt  5339
ttttaccaga aaacccctat aaattaaaaa tttttttactt aaatttaaga attaaaaaaa 5399 tacaaaaaag aaaaaatgaa aataaaggaa taagaagtta cctac                 5444

<210> SEQ ID NO 2
<211> LENGTH: 1429
<212> TYPE: PRT
<213> ORGANISM: Homo sapiens

<400> SEQUENCE: 2

Met Ala Gly Gly Ala Trp Gly Arg Leu Ala Cys Tyr Leu Glu Phe Leu
1               5                   10                  15

Lys Lys Glu Glu Leu Lys Glu Phe Gln Leu Leu Leu Ala Asn Lys Ala
```

```
                    20                  25                  30
His Ser Arg Ser Ser Gly Glu Thr Pro Ala Gln Pro Glu Lys Thr
         35                  40                  45
Ser Gly Met Glu Val Ala Ser Tyr Leu Val Ala Gln Tyr Gly Glu Gln
     50                  55                  60
Arg Ala Trp Asp Leu Ala Leu His Thr Trp Glu Gln Met Gly Leu Arg
 65                  70                  75                  80
Ser Leu Cys Ala Gln Ala Gln Glu Gly Ala Gly His Ser Pro Ser Phe
                 85                  90                  95
Pro Tyr Ser Pro Ser Glu Pro His Leu Gly Ser Pro Ser Gln Pro Thr
             100                 105                 110
Ser Thr Ala Val Leu Met Pro Trp Ile His Glu Leu Pro Ala Gly Cys
         115                 120                 125
Thr Gln Gly Ser Glu Arg Arg Val Leu Arg Gln Leu Pro Asp Thr Ser
     130                 135                 140
Gly Arg Arg Trp Arg Glu Ile Ser Ala Ser Leu Leu Tyr Gln Ala Leu
145                 150                 155                 160
Pro Ser Ser Pro Asp His Glu Ser Pro Ser Gln Glu Ser Pro Asn Ala
                 165                 170                 175
Pro Thr Ser Thr Ala Val Leu Gly Ser Trp Gly Ser Pro Pro Gln Pro
             180                 185                 190
Ser Leu Ala Pro Arg Glu Gln Glu Ala Pro Gly Thr Gln Trp Pro Leu
         195                 200                 205
Asp Glu Thr Ser Gly Ile Tyr Tyr Thr Glu Ile Arg Glu Arg Glu Arg
     210                 215                 220
Glu Lys Ser Glu Lys Gly Arg Pro Pro Trp Ala Ala Val Gly Thr
225                 230                 235                 240
Pro Pro Gln Ala His Thr Ser Leu Gln Pro His His Pro Trp Glu
                 245                 250                 255
Pro Ser Val Arg Glu Ser Leu Cys Ser Thr Trp Pro Trp Lys Asn Glu
             260                 265                 270
Asp Phe Asn Gln Lys Phe Thr Gln Leu Leu Leu Gln Arg Pro His
         275                 280                 285
Pro Arg Ser Gln Asp Pro Leu Val Lys Arg Ser Trp Pro Asp Tyr Val
     290                 295                 300
Glu Glu Asn Arg Gly His Leu Ile Glu Ile Arg Asp Leu Phe Gly Pro
305                 310                 315                 320
Gly Leu Asp Thr Gln Glu Pro Arg Ile Val Ile Leu Gln Gly Ala Ala
                 325                 330                 335
Gly Ile Gly Lys Ser Thr Leu Ala Arg Gln Val Lys Glu Ala Trp Gly
             340                 345                 350
Arg Gly Gln Leu Tyr Gly Asp Arg Phe Gln His Val Phe Tyr Phe Ser
         355                 360                 365
Cys Arg Glu Leu Ala Gln Ser Lys Val Val Ser Leu Ala Glu Leu Ile
     370                 375                 380
Gly Lys Asp Gly Thr Ala Thr Pro Ala Pro Ile Arg Gln Ile Leu Ser
385                 390                 395                 400
Arg Pro Glu Arg Leu Leu Phe Ile Leu Asp Gly Val Asp Glu Pro Gly
                 405                 410                 415
Trp Val Leu Gln Glu Pro Ser Ser Glu Leu Cys Leu His Trp Ser Gln
             420                 425                 430
Pro Gln Pro Ala Asp Ala Leu Leu Gly Ser Leu Leu Gly Lys Thr Ile
         435                 440                 445
```

-continued

```
Leu Pro Glu Ala Ser Phe Leu Ile Thr Ala Arg Thr Thr Ala Leu Gln
    450                 455                 460
Asn Leu Ile Pro Ser Leu Glu Gln Ala Arg Trp Val Glu Val Leu Gly
465                 470                 475                 480
Phe Ser Glu Ser Ser Arg Lys Glu Tyr Phe Tyr Arg Tyr Phe Thr Asp
                    485                 490                 495
Glu Arg Gln Ala Ile Arg Ala Phe Arg Leu Val Lys Ser Asn Lys Glu
                500                 505                 510
Leu Trp Ala Leu Cys Leu Val Pro Trp Val Ser Trp Leu Ala Cys Thr
            515                 520                 525
Cys Leu Met Gln Gln Met Lys Arg Lys Glu Lys Leu Thr Leu Thr Ser
    530                 535                 540
Lys Thr Thr Thr Thr Leu Cys Leu His Tyr Leu Ala Gln Ala Leu Gln
545                 550                 555                 560
Ala Gln Pro Leu Gly Pro Gln Leu Arg Asp Leu Cys Ser Leu Ala Ala
                    565                 570                 575
Glu Gly Ile Trp Gln Lys Lys Thr Leu Phe Ser Pro Asp Asp Leu Arg
                580                 585                 590
Lys His Gly Leu Asp Gly Ala Ile Ile Ser Thr Phe Leu Lys Met Gly
            595                 600                 605
Ile Leu Gln Glu His Pro Ile Pro Leu Ser Tyr Ser Phe Ile His Leu
    610                 615                 620
Cys Phe Gln Glu Phe Phe Ala Ala Met Ser Tyr Val Leu Glu Asp Glu
625                 630                 635                 640
Lys Gly Arg Gly Lys His Ser Asn Cys Ile Ile Asp Leu Glu Lys Thr
                    645                 650                 655
Leu Glu Ala Tyr Gly Ile His Gly Leu Phe Gly Ala Ser Thr Thr Arg
                660                 665                 670
Phe Leu Leu Gly Leu Leu Ser Asp Glu Gly Glu Arg Glu Met Glu Asn
            675                 680                 685
Ile Phe His Cys Arg Leu Ser Gln Gly Arg Asn Leu Met Gln Trp Val
    690                 695                 700
Pro Ser Leu Gln Leu Leu Leu Gln Pro His Ser Leu Glu Ser Leu His
705                 710                 715                 720
Cys Leu Tyr Glu Thr Arg Asn Lys Thr Phe Leu Thr Gln Val Met Ala
                    725                 730                 735
His Phe Glu Glu Met Gly Met Cys Val Glu Thr Asp Met Glu Leu Leu
                740                 745                 750
Val Cys Thr Phe Cys Ile Lys Phe Ser Arg His Val Lys Lys Leu Gln
            755                 760                 765
Leu Ile Glu Gly Arg Gln His Arg Ser Thr Trp Ser Pro Thr Met Val
    770                 775                 780
Val Leu Phe Arg Trp Val Pro Val Thr Asp Ala Tyr Trp Gln Ile Leu
785                 790                 795                 800
Phe Ser Val Leu Lys Val Thr Arg Asn Leu Lys Glu Leu Asp Leu Ser
                    805                 810                 815
Gly Asn Ser Leu Ser His Ser Ala Val Lys Ser Leu Cys Lys Thr Leu
                820                 825                 830
Arg Arg Pro Arg Cys Leu Leu Glu Thr Leu Arg Leu Ala Gly Cys Gly
            835                 840                 845
Leu Thr Ala Glu Asp Cys Lys Asp Leu Ala Phe Gly Leu Arg Ala Asn
    850                 855                 860
```

```
-continued

Gln Thr Leu Thr Glu Leu Asp Leu Ser Phe Asn Val Leu Thr Asp Ala
865                 870                 875                 880

Gly Ala Lys His Leu Cys Gln Arg Leu Arg Gln Pro Ser Cys Lys Leu
            885                 890                 895

Gln Arg Leu Gln Leu Val Ser Cys Gly Leu Thr Ser Asp Cys Cys Gln
        900                 905                 910

Asp Leu Ala Ser Val Leu Ser Ala Ser Pro Ser Leu Lys Glu Leu Asp
    915                 920                 925

Leu Gln Gln Asn Asn Leu Asp Asp Val Gly Val Arg Leu Leu Cys Glu
930                 935                 940

Gly Leu Arg His Pro Ala Cys Lys Leu Ile Arg Leu Gly Leu Asp Gln
945                 950                 955                 960

Thr Thr Leu Ser Asp Glu Met Arg Gln Glu Leu Arg Ala Leu Glu Gln
            965                 970                 975

Glu Lys Pro Gln Leu Leu Ile Phe Ser Arg Arg Lys Pro Ser Val Met
        980                 985                 990

Thr Pro Thr Glu Gly Leu Asp Thr Gly Glu Met Ser Asn Ser Thr Ser
    995                 1000                1005

Ser Leu Lys Arg Gln Arg Leu Gly Ser Glu Arg Ala Ala Ser His Val
    1010                1015                1020

Ala Gln Ala Asn Leu Lys Leu Leu Asp Val Ser Lys Ile Phe Pro Ile
1025                1030                1035                1040

Ala Glu Ile Ala Glu Glu Ser Ser Pro Glu Val Val Pro Val Glu Leu
            1045                1050                1055

Leu Cys Val Pro Ser Pro Ala Ser Gln Gly Asp Leu His Thr Lys Pro
        1060                1065                1070

Leu Gly Thr Asp Asp Asp Phe Trp Gly Pro Thr Gly Pro Val Ala Thr
    1075                1080                1085

Glu Val Val Asp Lys Glu Lys Asn Leu Tyr Arg Val His Phe Pro Val
    1090                1095                1100

Ala Gly Ser Tyr Arg Trp Pro Asn Thr Gly Leu Cys Phe Val Met Arg
1105                1110                1115                1120

Glu Ala Val Thr Val Glu Ile Glu Phe Cys Val Trp Asp Gln Phe Leu
            1125                1130                1135

Gly Glu Ile Asn Pro Gln His Ser Trp Met Val Ala Gly Pro Leu Leu
        1140                1145                1150

Asp Ile Lys Ala Glu Pro Gly Ala Val Glu Ala Val His Leu Pro His
    1155                1160                1165

Phe Val Ala Leu Gln Gly Gly His Val Asp Thr Ser Leu Phe Gln Met
    1170                1175                1180

Ala His Phe Lys Glu Glu Gly Met Leu Leu Glu Lys Pro Ala Arg Val
1185                1190                1195                1200

Glu Leu His His Ile Val Leu Glu Asn Pro Ser Phe Ser Pro Leu Gly
            1205                1210                1215

Val Leu Leu Lys Met Ile His Asn Ala Leu Arg Phe Ile Pro Val Thr
        1220                1225                1230

Ser Val Val Leu Leu Tyr His Arg Val His Pro Glu Glu Val Thr Phe
    1235                1240                1245

His Leu Tyr Leu Ile Pro Ser Asp Cys Ser Ile Arg Lys Glu Leu Glu
    1250                1255                1260

Leu Cys Tyr Arg Ser Pro Gly Glu Asp Gln Leu Phe Ser Glu Phe Tyr
1265                1270                1275                1280

Val Gly His Leu Gly Ser Gly Ile Arg Leu Gln Val Lys Asp Lys Lys
```

-continued

```
                   1285                1290                1295
Asp Glu Thr Leu Val Trp Glu Ala Leu Val Lys Pro Gly Asp Leu Met
            1300                1305                1310

Pro Ala Thr Thr Leu Ile Pro Pro Ala Arg Ile Ala Val Pro Ser Pro
        1315                1320                1325

Leu Asp Ala Pro Gln Leu Leu His Phe Val Asp Gln Tyr Arg Glu Gln
    1330                1335                1340

Leu Ile Ala Arg Val Thr Ser Val Glu Val Val Leu Asp Lys Leu His
1345                1350                1355                1360

Gly Gln Val Leu Ser Gln Glu Gln Tyr Glu Arg Val Leu Ala Glu Asn
            1365                1370                1375

Thr Arg Pro Ser Gln Met Arg Lys Leu Phe Ser Leu Ser Gln Ser Trp
        1380                1385                1390

Asp Arg Lys Cys Lys Asp Gly Leu Tyr Gln Ala Leu Lys Glu Thr His
    1395                1400                1405

Pro His Leu Ile Met Glu Leu Trp Glu Lys Gly Ser Lys Gly Leu
    1410                1415                1420

Leu Pro Leu Ser Ser
1425

<210> SEQ ID NO 3
<211> LENGTH: 5059
<212> TYPE: DNA
<213> ORGANISM: Homo sapiens
<220> FEATURE:
<221> NAME/KEY: CDS
<222> LOCATION: (314)...(1606)

<400> SEQUENCE: 3
ctggttctca acttcttttg aaataatgtt catagagaag gagggctgtc tgagattcga     60
gggaaacaag ctctcaggac ttccggtcgc catgatggct gtgggcggta aacgcggtta    120
gtgcaagcat ctgggccatc ttcaatggta aaaagatac agtaaagaca taaataccac     180
atttgacaaa tggaaaaaaa ggagtgtcca gaaaagagta gcagcagtga ggaagagctg    240
ccgagacggg tatacaggga ctaccctgt gtttctgaga ccctttgtga catctcacat     300
tttttccaag aag atg atg aga cag agg cag agc cat tat tgt tcc gtg      349
                Met Met Arg Gln Arg Gln Ser His Tyr Cys Ser Val
                 1               5                  10 ctg ttc ctg agt gtc aac tat ctg ggg ggg aca ttc cca gga gac att      397
Leu Phe Leu Ser Val Asn Tyr Leu Gly Gly Thr Phe Pro Gly Asp Ile
         15                  20                  25 tgc tca gaa gag aat caa ata gtt tcc tct tat gct tct aaa gtc tgt      445
Cys Ser Glu Glu Asn Gln Ile Val Ser Ser Tyr Ala Ser Lys Val Cys
 30                  35                  40 ttt gag atc gaa gaa gat tat aaa aat cgt cag ttt ctg ggg cct gaa      493
Phe Glu Ile Glu Glu Asp Tyr Lys Asn Arg Gln Phe Leu Gly Pro Glu
 45                  50                  55                  60 gga aat gtg gat gtt gag ttg att gat aag agc aca aac aga tac agc      541
Gly Asn Val Asp Val Glu Leu Ile Asp Lys Ser Thr Asn Arg Tyr Ser
                 65                  70                  75 gtt tgg ttc ccc act gct ggc tgg tat ctg tgg tca gcc aca ggc ctc      589
Val Trp Phe Pro Thr Ala Gly Trp Tyr Leu Trp Ser Ala Thr Gly Leu
         80                  85                  90 ggc ttc ctg gta agg gat gag gtc aca gtg acg att gcg ttt ggt tcc      637
Gly Phe Leu Val Arg Asp Glu Val Thr Val Thr Ile Ala Phe Gly Ser
     95                  100                 105
```

-continued

| | |
|---|---|
| tgg agt cag cac ctg gcc ctg gac ctg cag cac cat gaa cag tgg ctg<br>Trp Ser Gln His Leu Ala Leu Asp Leu Gln His His Glu Gln Trp Leu<br>110               115                    120 | 685 |
| gtg ggc ggc ccc ttg ttt gat gtc act gca gag cca gag gag gct gtc<br>Val Gly Gly Pro Leu Phe Asp Val Thr Ala Glu Pro Glu Glu Ala Val<br>125               130                    135                   140 | 733 |
| gcc gaa atc cac ctc ccc cac ttc atc tcc ctc caa ggt gag gtg gac<br>Ala Glu Ile His Leu Pro His Phe Ile Ser Leu Gln Gly Glu Val Asp<br>              145                    150                   155 | 781 |
| gtc tcc tgg ttt ctc gtt gcc cat ttt aag aat gaa ggg atg gtc ctg<br>Val Ser Trp Phe Leu Val Ala His Phe Lys Asn Glu Gly Met Val Leu<br>           160                    165                   170 | 829 |
| gag cat cca gcc cgg gtg gag cct ttc tat gct gtc ctg gaa agc ccc<br>Glu His Pro Ala Arg Val Glu Pro Phe Tyr Ala Val Leu Glu Ser Pro<br>175               180                    185 | 877 |
| agc ttc tct ctg atg ggc atc ctg ctg cgg atc gcc agt ggg act cgc<br>Ser Phe Ser Leu Met Gly Ile Leu Leu Arg Ile Ala Ser Gly Thr Arg<br>      190                   195                   200 | 925 |
| ctc tcc atc ccc atc act tcc aac aca ttg atc tat tat cac ccc cac<br>Leu Ser Ile Pro Ile Thr Ser Asn Thr Leu Ile Tyr Tyr His Pro His<br>205               210                    215                   220 | 973 |
| ccc gaa gat att aag ttc cac ttg tac ctt gtc ccc agc gac gcc ttg<br>Pro Glu Asp Ile Lys Phe His Leu Tyr Leu Val Pro Ser Asp Ala Leu<br>              225                    230                   235 | 1021 |
| cta aca aag gcg ata gat gat gag gaa gat cgc ttc cat ggt gtg cgc<br>Leu Thr Lys Ala Ile Asp Asp Glu Glu Asp Arg Phe His Gly Val Arg<br>           240                    245                   250 | 1069 |
| ctg cag act tcg ccc cca atg gaa ccc ctg aac ttt ggt tcc agt tat<br>Leu Gln Thr Ser Pro Pro Met Glu Pro Leu Asn Phe Gly Ser Ser Tyr<br>              255                    260                   265 | 1117 |
| att gtg tct aat tct gct aac ctg aaa gta atg ccc aag gag ttg aaa<br>Ile Val Ser Asn Ser Ala Asn Leu Lys Val Met Pro Lys Glu Leu Lys<br>270               275                    280 | 1165 |
| ttg tcc tac agg agc cct gga gaa att cag cac ttc tca aaa ttc tat<br>Leu Ser Tyr Arg Ser Pro Gly Glu Ile Gln His Phe Ser Lys Phe Tyr<br>285               290                    295                   300 | 1213 |
| gct ggg cag atg aag gaa ccc att caa ctt gag att act gaa aaa aga<br>Ala Gly Gln Met Lys Glu Pro Ile Gln Leu Glu Ile Thr Glu Lys Arg<br>              305                    310                   315 | 1261 |
| cat ggg act ttg gtg tgg gat act gag gtg aag cca gtg gat ctc cag<br>His Gly Thr Leu Val Trp Asp Thr Glu Val Lys Pro Val Asp Leu Gln<br>           320                    325                   330 | 1309 |
| ctt gta gct gca tca gcc cct cct cct ttc tca ggt gca gcc ttt gtg<br>Leu Val Ala Ala Ser Ala Pro Pro Pro Phe Ser Gly Ala Ala Phe Val<br>              335                    340                   345 | 1357 |
| aag gag aac cac cgg caa ctc caa gcc agg atg ggg gac ctg aaa ggg<br>Lys Glu Asn His Arg Gln Leu Gln Ala Arg Met Gly Asp Leu Lys Gly<br>350               355                    360 | 1405 |
| gtg ctc gat gat ctc cag gac aat gag gtt ctt act gag aat gag aag<br>Val Leu Asp Asp Leu Gln Asp Asn Glu Val Leu Thr Glu Asn Glu Lys<br>365               370                    375                   380 | 1453 |
| gag ctg gtg gag cag gaa aag aca cgg cag agc aag aat gag gcc ttg<br>Glu Leu Val Glu Gln Glu Lys Thr Arg Gln Ser Lys Asn Glu Ala Leu<br>              385                    390                   395 | 1501 |
| ctg agc atg gtg gag aag aaa ggg gac ctg gcc ctg gac gtg ctc ttc<br>Leu Ser Met Val Glu Lys Lys Gly Asp Leu Ala Leu Asp Val Leu Phe<br>           400                    405                   410 | 1549 |
| aga agc att agt gaa agg gac cct tac ctc gtg tcc tat ctt aga cag<br>Arg Ser Ile Ser Glu Arg Asp Pro Tyr Leu Val Ser Tyr Leu Arg Gln<br>              415                    420                   425 | 1597 |

-continued

```
cag aat ttg taaaatgagt cagttaggta gtctggaaga gagaatccag        1646
Gln Asn Leu
    430 cgttctcatt ggaaatggat aaacagaaat gtgatcattg atttcagtgt tcaagacaga        1706 agaagactgg gtaacatcta tcacacaggc tttcaggaca gacttgtaac ctggcatgta        1766 cctattgact gtatcctcat gcattttcct caagaatgtc tgaagaaggt agtaatattc        1826 cttttaaatt ttttccaacc attgcttgat atatcactat tttatccatt gacatgattc        1886 ttgaagaccc aggataaagg acatccggat aggtgtgttt atgaaggatg gggcctggaa        1946 aggcaacttt tcctgattaa tgtgaaaaat aattcctatg acactccgt ttgaagtatc         2006 accttctcat aactaaaagc agaaaagcta acaaaagctt ctcagctgag gacactcaag        2066 gcatacatga tgacagtctt tttttttttt gtatgttagg actttaacac tttatctatg        2126 gctactgtta ttagaacaat gtaaatgtat ttgctgaaag agagcacaaa aatgggagaa        2186 aatgcaaaca tgagcagaaa atattttccc actggtgtgt agcctgctac aaggagttgt        2246 tgggttaaat gttcatggtc aactccaagg aatactgaga tgaaatgtgg taaatcaact        2306 ccacagaacc accaaaaaga aaatgagggt aattcagctt attctgagac agacattcct        2366 ggcaatgtac catacaaaaa ataagccaac tctgacattt ggattctacc atagactctg        2426 tcattttgta gccatttcag ctgtcttttg attaatgttt tcgtggcaca catatttcca        2486 tccttttatg tttaatctgt ttaaaacaag ttcctagtag acaccatctg gttgagtcag        2546 ttttttttat ggtgtatttt gaacccattc tgatagtctc ttttaactgg aagatttcaa        2606 ttacttacgt taatgtaatt attaatatgt taggatttat cctcagtcag ccagtttgtt        2666 atgtcttttc tattctactg ttatcacatt tgtaccactt aaagtggaat ctaggcactt        2726 tatcaccatt tagatcctat tacctttttct catctaggat atagttatct tctacataat       2786 cttttctgtat cttaaaaccc atcaataaat tattatatat tttctacttt taatcactca       2846 gaagatttaa aaaactcatg agaagagtaa tctgttatgt ttttccagat atttaccatt       2906 tctgttgctc ttccttcatt attttccaaa tttcgttctg caaatttcca cttcttctga       2966 tagacgtttt ttagttcttt tagagtggtt ctgataggta cagattctct tatttttgc        3026 ttcctctgag gacatctttt tctcaccttc attctcagtg atgtttttg cttgtagtat         3086 ttttagttga cattgttttc tgttcagcag tttccttta gcttccgtat ttcctgatga         3146 gaaatctgca gtcattcaaa ttgttgtttc cctgtatgta gtgtgtcatt tttctgtcag        3206 atttcaaggt atttatcttt agttttagc catttcatta tgttggggat gagtttcctt         3266 gttttattcc ctttggaatt tgctccaatt cataaatttg cagttttatg tcttttacca        3326 aacttagagg ttttcagcct aatttctaaa atactttt attagcctga ttttcatctt          3386 tataggaaat agtttaagtg atgacaagtt ccaatagctt atatgcccag aaggccttca        3446 aaataagaat tttgaaagaa tacagaaaac aaactttat atccttctca tgtcttctac         3506 tgtaaaattc atatgctttg ctactctaaa cctagtttga aatcaacagt cttgagaata        3566 gatgaaaatt ttgatgaata gtggaattct tttaaatgga aacctcttac atgtgatttt       3626 ccttgccatc tagaaataaa ccatagtatt tatgttgaat caatcaatat tatattttgt        3686 tttttcctc ctcttctgag actcttattg tggaaatgtt agacttttat gttttcctaa        3746 atgtccctga tattctactt atttagaaca tcttttcatt ttttccatta ttctgattgg        3806 gtaatttta tttgtctatt ttcaaatttg ctggagtgtt cacctgttgt tgtctgtgtc         3866
```

-continued

```
gtcccactga gtgcattcac caccttttaa attttggtca ctgtatgtat cagttctaaa     3926
atttccattt tgttctctat attttaaatt tcttggctta tattctattt tcctgcaaat     3986
gtgtcagcat ttgcttgttt gagctttttt tttttcaaga cagggtctca actctgttac     4046
ccaggctgga gtgcagtggt gcgatctcag ctcactgcaa cctctgcctc ctggttcaag     4106
cgattattgt gcctcagcct cctgagtagc tgggattaca ggcatgcacc accacagccc     4166
agctaatttt ttgtattttt agtagagaca gagttttgct atgttggcca ggctggtttt     4226
gaactcctgg cctcaagtga tccacccacc tcagcctccc aaagtgctgg gattacaggc     4286
cactacacct ggcacatttg agtatttttt tttttttttt tttttgaga tggagtctcg     4346 ctctgtcatc taggctggag tgcagtggtg tgatctcagc tcactgcagc ctctgtctcc     4406
cgggctcaag cgattctctt gcctcagcct cctgagtagc taggactaca ggtgcatgcc     4466
aacacgcccg gctaattttt ttaaaaaata ttttagtag agacagggtt tcaccatttt     4526
ggccaggatg gtctcgatct cctgacctca tgatccaccc gcctcggcct tccaaagtgc     4586
tgggattaca ggcatgagcc accgtgcctg gcctcatttg agtattttta taatgtctct     4646
tttaaagtct ttgtcagata attccactgt acatgttatt cagtgtttgg tgtccactga     4706
gttgtcattt gccagacaag tggagatttt tgcagctcat ccttgtattc tcagtagttc     4766
cgatatgtac cctcgacatg tgaatgttat cttatgagac tctgttttat ttgtatccaa     4826
cagaagatgt ttattattta tttggctttc tgtgaactga ggtcttaata tcagctcatt     4886
ttaaaagtct ttgcagtggt attcggatct atcctgtgtg tgcctatgag attgggtgca     4946
gtgtatcctg ttagctccat tctcagggcg tttgaatgtg aattaggacc agcgcaatga     5006
atgctcaagt tggggttggg cgttagaatt cataaaagtc tttatatgct cag           5059
```

<210> SEQ ID NO 4
<211> LENGTH: 431
<212> TYPE: PRT
<213> ORGANISM: Homo sapiens

<400> SEQUENCE: 4

```
Met Met Arg Gln Arg Gln Ser His Tyr Cys Ser Val Leu Phe Leu Ser
 1               5                  10                  15

Val Asn Tyr Leu Gly Gly Thr Phe Pro Gly Asp Ile Cys Ser Glu Glu
            20                  25                  30

Asn Gln Ile Val Ser Ser Tyr Ala Ser Lys Val Cys Phe Glu Ile Glu
        35                  40                  45

Glu Asp Tyr Lys Asn Arg Gln Phe Leu Gly Pro Glu Gly Asn Val Asp
    50                  55                  60

Val Glu Leu Ile Asp Lys Ser Thr Asn Arg Tyr Ser Val Trp Phe Pro
65                  70                  75                  80

Thr Ala Gly Trp Tyr Leu Trp Ser Ala Thr Gly Leu Gly Phe Leu Val
                85                  90                  95

Arg Asp Glu Val Thr Val Thr Ile Ala Phe Gly Ser Trp Ser Gln His
            100                 105                 110

Leu Ala Leu Asp Leu Gln His His Glu Gln Trp Leu Val Gly Gly Pro
        115                 120                 125

Leu Phe Asp Val Thr Ala Glu Pro Glu Glu Ala Val Ala Glu Ile His
    130                 135                 140

Leu Pro His Phe Ile Ser Leu Gln Gly Glu Val Asp Val Ser Trp Phe
145                 150                 155                 160

Leu Val Ala His Phe Lys Asn Glu Gly Met Val Leu Glu His Pro Ala
```

```
                    165                 170                 175
Arg Val Glu Pro Phe Tyr Ala Val Leu Glu Ser Pro Ser Phe Ser Leu
                180                 185                 190

Met Gly Ile Leu Leu Arg Ile Ala Ser Gly Thr Arg Leu Ser Ile Pro
            195                 200                 205

Ile Thr Ser Asn Thr Leu Ile Tyr Tyr His Pro His Pro Glu Asp Ile
        210                 215                 220

Lys Phe His Leu Tyr Leu Val Pro Ser Asp Ala Leu Leu Thr Lys Ala
225                 230                 235                 240

Ile Asp Asp Glu Glu Asp Arg Phe His Gly Val Arg Leu Gln Thr Ser
                245                 250                 255

Pro Pro Met Glu Pro Leu Asn Phe Gly Ser Ser Tyr Ile Val Ser Asn
            260                 265                 270

Ser Ala Asn Leu Lys Val Met Pro Lys Glu Leu Lys Leu Ser Tyr Arg
        275                 280                 285

Ser Pro Gly Glu Ile Gln His Phe Ser Lys Phe Tyr Ala Gly Gln Met
290                 295                 300

Lys Glu Pro Ile Gln Leu Glu Ile Thr Glu Lys Arg His Gly Thr Leu
305                 310                 315                 320

Val Trp Asp Thr Glu Val Lys Pro Val Asp Leu Gln Leu Val Ala Ala
                325                 330                 335

Ser Ala Pro Pro Pro Phe Ser Gly Ala Ala Phe Val Lys Glu Asn His
            340                 345                 350

Arg Gln Leu Gln Ala Arg Met Gly Asp Leu Lys Gly Val Leu Asp Asp
        355                 360                 365

Leu Gln Asp Asn Glu Val Leu Thr Glu Asn Glu Lys Glu Leu Val Glu
    370                 375                 380

Gln Glu Lys Thr Arg Gln Ser Lys Asn Glu Ala Leu Leu Ser Met Val
385                 390                 395                 400

Glu Lys Lys Gly Asp Leu Ala Leu Asp Val Leu Phe Arg Ser Ile Ser
                405                 410                 415

Glu Arg Asp Pro Tyr Leu Val Ser Tyr Leu Arg Gln Gln Asn Leu
            420                 425                 430

<210> SEQ ID NO 5
<211> LENGTH: 4287
<212> TYPE: DNA
<213> ORGANISM: Homo sapiens

<400> SEQUENCE: 5 tggctggcg  gagcctgggg  ccgcctggcc  tgttacttgg  agttcctgaa  gaaggaggag      60
ctgaaggagt  tccagcttct  gctcgccaat  aaagcgcact  ccaggagctc  ttcgggtgag    120 acaccgctc  agccagagaa  gacgagtggc  atggaggtgg  cctcgtacct  ggtggctcag    180
tatggggagc  agcgggcctg  ggacctagcc  ctccatacct  gggagcagat  ggggctgagg    240
tcactgtgcg  cccaagccca  ggaaggggca  ggccactctc  cctcattccc  ctacagccca    300
agtgaacccc  acctggggtc  tcccagccaa  cccacctcca  ccgcagtgct  aatgccctgg    360
atccatgaat  tgccggcggg  gtgcacccag  ggctcagaga  gaagggtttt  gagacagctg    420
cctgacacat  ctggacgccg  ctggagagaa  atctctgcct  cactcctcta  ccaagctctt    480
ccaagctccc  cagaccatga  gtctccaagc  caggagtcac  ccaacgcccc  cacatccaca    540
gcagtgctgg  ggagctgggg  atccccacct  cagcccagcc  tagcacccag  agagcaggag    600
```

-continued

```
gctcctggga cccaatggcc tctggatgaa acgtcaggaa tttactacac agaaatcaga    660
gaaagagaga gagagaaatc agagaaaggc aggcccccat gggcagcggt ggtaggaacg    720
cccccacagg cgcacaccag cctacagccc caccaccacc catgggagcc ttctgtgaga    780
gagagcctct gttccacatg gccctggaaa atgaggatt ttaaccaaaa attcacacag     840
ctgctacttc tacaaagacc tcaccccaga agccaagatc ccctggtcaa gagaagctgg    900
cctgattatg tggaggagaa tcgaggacat ttaattgaga tcagagactt atttggccca    960
ggcctggata cccaagaacc tcgcatagtc atactgcagg gggctgctgg aattgggaag   1020
tcaacactgg ccaggcaggt gaaggaagcc tgggggagag ccagctgta tggggaccgc    1080 ttccagcatg tcttctactt cagctgcaga gagctggccc agtccaaggt ggtgagtctc   1140
gctgagctca tcggaaaaga tgggacagcc actccggctc ccattagaca gatcctgtct   1200
aggccagagc ggctgctctt catcctcgat ggtgtagatg agccaggatg ggtcttgcag   1260
gagccgagtt ctgagctctg tctgcactgg agccagccac agccggcgga tgcactgctg   1320
ggcagtttgc tggggaaaac tatacttccc gaggcatcct tcctgatcac ggctcggacc   1380
acagctctgc agaacctcat tccttctttg gagcaggcac gttgggtaga ggtcctgggg   1440
ttctctgagt ccagcaggaa ggaatatttc tacagatatt tcacagatga aggcaagca    1500 attagagcct ttaggttggt caaatcaaac aaagagctct gggccctgtg tcttgtgccc   1560
tgggtgtcct ggctggcctg cacttgcctg atgcagcaga tgaagcggaa ggaaaaactc   1620
acactgactt ccaagaccac cacaaccctc tgtctacatt accttgccca ggctctccaa   1680
gctcagccat tgggacccca gctcagagac ctctgctctc tggctgctga gggcatctgg   1740
caaaaaaaga cccttttcag tccagatgac ctcaggaagc atgggttaga tggggccatc   1800
atctccacct tcttgaagat gggtattctt caagagcacc ccatccctct gagctacagc   1860
ttcattcacc tctgttttcca agagttcttt gcagcaatgt cctatgtctt ggaggatgag   1920
aaggggagag gtaaacattc taattgcatc atagatttgg aaaagacgct agaagcatat   1980
ggaatacatg gcctgtttgg ggcatcaacc acacgtttcc tattgggcct gttaagtgat   2040
gagggggaga gagagatgga gaacatcttt cactgccggc tgtctcaggg gaggaacctg   2100
atgcagtggg tcccgtccct gcagctgctg ctgcagccac actctctgga gtccctccac   2160
tgcttgtacg agactcggaa caaaacgttc ctgacacaag tgatggccca tttcgaagaa   2220
atgggcatgt gtgtagaaac agacatggag ctcttagtgt gcactttctg cattaaattc   2280
agccgccacg tgaagaagct tcagctgatt gagggcaggc agcacagatc aacatggagc   2340
cccaccatgg tagtcctgtt caggtgggtc ccagtcacag atgcctattg gcagattctc   2400
ttctccgtcc tcaaggtcac cagaaacctg aaggagctgg acctaagtgg aaactcgctg   2460
agccactctg cagtgaagag tcttttgtaag accctgagac gccctcgctg cctcctggag   2520
accctgcggt tggctggctg tggcctcaca gctgaggact gcaaggacct tgcctttggg   2580
ctgagagcca accagaccct gaccgagctg acctgagct tcaatgtgct cacggatgct    2640
ggagccaaac acctttgcca gagactgaga cagccgagct gcaagctaca gcgactgcag   2700
ctggtcagct gtggcctcac gtctgactgc tgccaggacc tggcctctgt gcttagtgcc   2760
agccccagcc tgaaggagct agacctgcag cagaacaacc tggatgacgt tggcgtgcga   2820
ctgctctgtg aggggctcag gcatcctgcc tgcaaactca tacgcctggg gctggaccag   2880
acaactctga gtgatgagat gaggcaggaa ctgagggccc tggagcagga gaaacctcag   2940
ctgctcatct tcagcagacg gaaaccaagt gtgatgaccc ctactgaggg cctggatacg   3000
```

```
ggagagatga gtaatagcac atcctcactc aagcggcaga gactcggatc agagagggcg    3060
gcttcccatg ttgctcaggc taatctcaaa ctcctggacg tgagcaagat cttcccaatt    3120
gctgagattg cagaggaaag ctccccagag gtagtaccgg tggaactctt gtgcgtgcct    3180
tctcctgcct ctcaagggga cctgcatacg aagcctttgg ggactgacga tgacttctgg    3240
ggccccacgg ggcctgtggc tactgaggta gttgacaaag aaaagaactt gtaccgagtt    3300
cacttccctg tagctggctc ctaccgctgg cccaacacgg gtctctgctt tgtgatgaga    3360
gaagcggtga ccgttgagat tgaattctgt gtgtgggacc agttcctggg tgagatcaac    3420
ccacagcaca gctggatggt ggcagggcct ctgctggaca tcaaggctga gcctggagct    3480
gtggaagctg tgcacctccc tcactttgtg gctctccaag ggggccatgt ggacacatcc    3540
ctgttccaaa tggcccactt taaagaggag gggatgctcc tggagaagcc agccagggtg    3600
gagctgcatc acatagttct ggaaaacccc agcttctccc ccttgggagt cctcctgaaa    3660
atgatccata atgccctgcg cttcattccc gtcacctctg tggtgttgct ttaccaccgc    3720
gtccatcctg aggaagtcac cttccacctc tacctgatcc caagtgactg ctccattcgg    3780
aaggaactgg agctctgcta tcgaagccct ggagaagacc agctgttctc ggagttctac    3840
gttggccact tgggatcagg atcaggctg caagtgaaag acaagaaaga tgagactctg    3900
gtgtgggagg ccttggtgaa accaggagat ctcatgcctg caactactct gatccctcca    3960
gcccgcatag ccgtaccttc acctctggat gccccgcagt tgctgcactt tgtggaccag    4020
tatcgagagc agctgatagc ccgagtgaca tcggtggagg ttgtcttgga caaactgcat    4080
ggacaggtgc tgagccagga gcagtacgag agggtgctgg ctgagaacac gaggcccagc    4140
cagatgcgga agctgttcag cttgagccag tcctgggacc ggaagtgcaa agatggactc    4200
taccaagccc tgaaggagac ccatcctcac ctcattatgg aactctggga agggcagc     4260
aaaaagggac tcctgccact cagcagc                                       4287

<210> SEQ ID NO 6
<211> LENGTH: 1293
<212> TYPE: DNA
<213> ORGANISM: Homo sapiens

<400> SEQUENCE: 6
atgatgagac agaggcagag ccattattgt tccgtgctgt tcctgagtgt caactatctg     60
gggggacat tcccaggaga catttgctca gaagagaatc aaatagtttc ctcttatgct    120
tctaaagtct gttttgagat cgaagaagat tataaaaatc gtcagtttct ggggcctgaa    180
ggaaatgtgg atgttgagtt gattgataag agcacaaaca gatacagcgt ttggttcccc    240
actgctggct ggtatctgtg gtcagccaca ggcctcggct tcctggtaag ggatgaggtc    300
acagtgacga ttgcgtttgg ttcctggagt cagcacctgg ccctggacct gcagcaccat    360
gaacagtggc tggtgggcgg ccccttgttt gatgtcactg cagagccaga ggaggctgtc    420
gccgaaatcc acctccccca cttcatctcc ctccaaggtg aggtggacgt ctcctggttt    480
ctcgttgccc attttaagaa tgaagggatg gtcctggagc atccagcccg ggtggagcct    540
ttctatgctg tcctggaaag ccccagcttc tctctgatgg gcatcctgct gcggatcgcc    600
agtgggactc gcctctccat ccccatcact tccaacacat tgatctatta tcaccccac    660
cccgaagata ttaagttcca cttgtaccct gtccccagcg acgccttgct aacaaaggcg    720
atagatgatg aggaagatcg cttccatggt gtgcgcctgc agacttcgcc cccaatggaa    780
```

-continued

```
ccccctgaact ttggttccag ttatattgtg tctaattctg ctaacctgaa agtaatgccc    840
aaggagttga aattgtccta caggagccct ggagaaattc agcacttctc aaaattctat    900
gctgggcaga tgaaggaacc cattcaactt gagattactg aaaaaagaca tgggactttg    960
gtgtgggata ctgaggtgaa gccagtggat ctccagcttg tagctgcatc agcccctcct   1020
cctttctcag gtgcagcctt tgtgaaggag aaccaccggc aactccaagc caggatgggg   1080
gacctgaaag gggtgctcga tgatctccag gacaatgagg ttcttactga aatgagaag    1140 gagctggtgg agcaggaaaa gacacggcag agcaagaatg aggccttgct gagcatggtg   1200
gagaagaaag gggacctggc cctggacgtg ctcttcagaa gcattagtga aagggaccct   1260
tacctcgtgt cctatcttag acagcagaat ttg                                1293
```

<210> SEQ ID NO 7
<211> LENGTH: 740
<212> TYPE: DNA
<213> ORGANISM: Homo sapiens
<220> FEATURE:
<221> NAME/KEY: CDS
<222> LOCATION: (54)...(638)

<400> SEQUENCE: 7

```
cgcgtccggc tgcagcgggg tgagcggcgg cagcggccgg ggatcctgga gcc atg        56
                                                           Met
                                                             1 ggg cgc gcg cgc gac gcc atc ctg gat gcg ctg gag aac ctg acc gcc     104
Gly Arg Ala Arg Asp Ala Ile Leu Asp Ala Leu Glu Asn Leu Thr Ala
            5                  10                  15 gag gag ctc aag aag ttc aag ctg aag ctg ctg tcg gtg ccg ctg cgc     152
Glu Glu Leu Lys Lys Phe Lys Leu Lys Leu Leu Ser Val Pro Leu Arg
         20                  25                  30 gag ggc tac ggg cgc atc ccg cgg ggc gcg ctg ctg tcc atg gac gcc     200
Glu Gly Tyr Gly Arg Ile Pro Arg Gly Ala Leu Leu Ser Met Asp Ala
     35                  40                  45 ttg gac ctc acc gac aag ctg gtc agc ttc tac ctg gag acc tac ggc     248
Leu Asp Leu Thr Asp Lys Leu Val Ser Phe Tyr Leu Glu Thr Tyr Gly
 50                  55                  60                  65 gcc gag ctc acc gct aac gtg ctg cgc gac atg ggc ctg cag gag atg     296
Ala Glu Leu Thr Ala Asn Val Leu Arg Asp Met Gly Leu Gln Glu Met
                 70                  75                  80 gcc ggg cag ctg cag gcg gcc acg cac cag ggc tct gga gcc gcg cca     344
Ala Gly Gln Leu Gln Ala Ala Thr His Gln Gly Ser Gly Ala Ala Pro
             85                  90                  95 gct ggg atc cag gcc cct cct cag tcg gca gcc aag cca ggc ctg cac     392
Ala Gly Ile Gln Ala Pro Pro Gln Ser Ala Ala Lys Pro Gly Leu His
        100                 105                 110 ttt ata gac cag cac cgg gct gcg ctt atc gcg agg gtc aca aac gtt     440
Phe Ile Asp Gln His Arg Ala Ala Leu Ile Ala Arg Val Thr Asn Val
    115                 120                 125 gag tgg ctg ctg gat gct ctg tac ggg aag gtc ctg acg gat gag cag     488
Glu Trp Leu Leu Asp Ala Leu Tyr Gly Lys Val Leu Thr Asp Glu Gln
130                 135                 140                 145 tac cag gca gtg cgg gcc gag ccc acc aac cca agc aag atg cgg aag     536
Tyr Gln Ala Val Arg Ala Glu Pro Thr Asn Pro Ser Lys Met Arg Lys
                150                 155                 160 ctc ttc agt ttc aca cca gcc tgg aac tgg acc tgc aag gac ttg ctc     584
Leu Phe Ser Phe Thr Pro Ala Trp Asn Trp Thr Cys Lys Asp Leu Leu
            165                 170                 175 ctc cag gcc cta agg gag tcc cag tcc tac ctg gtg gag gac ctg gag     632
Leu Gln Ala Leu Arg Glu Ser Gln Ser Tyr Leu Val Glu Asp Leu Glu
```

```
                180               185               190
cgg agc tgaggctcct tcccagcaac actccggtca gccctggca atcccaccaa        688
Arg Ser
    195 atcatcctga atctgatctt tttatacaca atatacgaaa agccagcttg aa            740

<210> SEQ ID NO 8
<211> LENGTH: 195
<212> TYPE: PRT
<213> ORGANISM: Homo sapiens

<400> SEQUENCE: 8

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
    195

<210> SEQ ID NO 9
<211> LENGTH: 585
<212> TYPE: DNA
<213> ORGANISM: Homo sapiens

<400> SEQUENCE: 9
atggggcgcg cgcgcgacgc catcctggat gcgctggaga acctgaccgc cgaggagctc        60
aagaagttca agctgaagct gctgtcggtg ccgctgcgcg agggctacgg cgcatcccg       120 cggggcgcgc tgctgtccat ggacgccttg gacctcaccg acaagctggt cagcttctac       180
ctggagacct acggcgccga gctcaccgct aacgtgctgc gcgacatggg cctgcaggag       240
atggccgggc agctgcaggc ggccacgcac cagggctctg gagccgcgcc agctgggatc       300
caggcccctc ctcagtcggc agccaagcca ggcctgcact ttatagacca gcaccgggct       360
gcgcttatcg cgagggtcac aaacgttgag tggctgctgg atgctctgta cgggaaggtc       420
ctgacggatg agcagtacca ggcagtgcgg gccgagccca ccaacccaag caagatgcgg       480
```

-continued

```
aagctcttca gtttcacacc agcctggaac tggacctgca aggacttgct cctccaggcc      540
ctaagggagt cccagtccta cctggtggag gacctggagc ggagc                     585

<210> SEQ ID NO 10
<211> LENGTH: 740
<212> TYPE: DNA
<213> ORGANISM: Homo sapiens

<400> SEQUENCE: 10
ttcaagctgg cttttcgtat attgtgtata aaaagatcag attcaggatg atttggtggg      60
attgccaggg gctgaccgga gtgttgctgg gaaggagcct cagctccgct ccaggtcctc     120
caccaggtag gactgggact cccttagggc ctggaggagc aagtccttgc aggtccagtt     180
ccaggctggt gtgaaactga agagcttccg catcttgctt gggttggtgg gctcggcccg     240
cactgcctgg tactgctcat ccgtcaggac cttcccgtac agagcatcca gcagccactc     300
aacgtttgtg accctcgcga taagcgcagc ccggtgctgg tctataaagt gcaggcctgg     360
cttggctgcc gactgaggag gggcctggat cccagctggc gcggctccag agccctggtg     420
cgtggccgcc tgcagctgcc cggccatctc ctgcaggccc atgtcgcgca gcacgttagc     480
ggtgagctcg gcgccgtagg tctccaggta gaagctgacc agcttgtcgg tgaggtccaa     540
ggcgtccatg gacagcagcg cgccccgcgg gatgcgcccg tagccctcgc gcagcggcac     600
cgacagcagc ttcagcttga acttcttgag ctcctcggcg gtcaggttct ccagcgcatc     660
caggatggcg tcgcgcgcgc gccccatggc tccaggatcc ccggccgctg ccgccgctca     720
ccccgctgca gccggacgcg                                                 740
```

What is claimed is:

1. A method for identifying a compound which modulates the interaction between CARD-7 and CARD-5, the method comprising:
   a) contacting, in the presence of a test compound, a first polypeptide comprising amino acids 1335–1429 of SEQ ID NO:2 with a second polypeptide comprising amino acids 111–181 of SEQ 8;
   b) measuring the binding of the first polypeptide to the second polypeptide in the presence of the test compound; and
   c) identifying the test compound as a compound which modulates the interaction between CARD-7 and CARD-5 when the binding of the first polypeptide to the second polypeptide is increased or decreased in the presence of the test compound compared the binding of the first polypeptide to the second polypeptide in the absence of the test compound.

2. The method of claim 1 wherein the first polypeptide is immobilized on a solid support.

3. The method of claim 1 wherein the second polypeptide is immobilized on a solid support.

4. The method of claim 1 wherein the test compound is a peptide.

5. The method of claim 1 wherein the test compound is a peptide analog.

6. The method of claim 2 wherein the first polypeptide is immobilized by binding to an antibody that is bound to the solid support.

7. The method of claim 3 wherein the second polypeptide is immobilized by binding to an antibody that is bound to the solid support.

8. The method of claim 1 wherein the first polypeptide is detectably labeled.

9. The method of claim 1 wherein the second polypeptide is detectably labeled.

10. The method of claim 1 further comprising measuring the binding of the first polypeptide to the second polypeptide in the absence of the test compound.

11. The method of claim 1, wherein the first polypeptide comprises the amino acid sequence of SEQ ID NO:2.

12. The method of claim 1, wherein the second polypeptide comprises the amino acid sequence of SEQ ID NO:8.

13. The method of claim 1, wherein the first polypeptide is a fusion protein.

* * * * *